(12) United States Patent
Eastham et al.

(10) Patent No.: US 8,604,236 B2
(45) Date of Patent: Dec. 10, 2013

(54) CATALYST SYSTEM

(75) Inventors: Ronald Graham Eastham, Co Durham (GB); Neil Tindale, Cleveland (GB)

(73) Assignee: Lucite International UK Limited, Hampshire (GB)

( * ) Notice: Subject to any disclaimer, the term of this patent is extended or adjusted under 35 U.S.C. 154(b) by 337 days.

(21) Appl. No.: 11/990,272

(22) PCT Filed: Aug. 4, 2006

(86) PCT No.: PCT/GB2006/002915
§ 371 (c)(1),
(2), (4) Date: Mar. 10, 2009

(87) PCT Pub. No.: WO2007/020379
PCT Pub. Date: Feb. 22, 2007

(65) Prior Publication Data
US 2009/0216041 A1 Aug. 27, 2009

(30) Foreign Application Priority Data
Aug. 12, 2005 (GB) .................................. 0516556.8

(51) Int. Cl.
*C07C 67/38* (2006.01)
(52) U.S. Cl.
USPC ........................................................ 560/233
(58) Field of Classification Search
None
See application file for complete search history.

(56) References Cited

U.S. PATENT DOCUMENTS

| | | |
|---|---|---|
| 3,131,204 A | 4/1964 | Sisler et al. |
| 3,564,020 A | 2/1971 | Fenton |
| 4,245,115 A | 1/1981 | Butter |
| 4,377,708 A | 3/1983 | Morris |
| 4,500,727 A | 2/1985 | Kitamura et al. |
| 4,504,684 A | 3/1985 | Fox et al. |
| 4,517,061 A | 5/1985 | Fauvarque |
| 4,786,443 A | 11/1988 | Drent et al. |
| 4,818,810 A | 4/1989 | Drent |
| 4,835,250 A | 5/1989 | Drent |
| 4,868,282 A | 9/1989 | Van Broekhoven et al. |
| 4,880,903 A | 11/1989 | Van Broekhoven et al. |

(Continued)

FOREIGN PATENT DOCUMENTS

| | | |
|---|---|---|
| AU | 2003259322 A1 | 2/2004 |
| CA | 2498293 A1 | 3/2004 |

(Continued)

OTHER PUBLICATIONS

Wang et al., "Polymer-Bound Bidentate-Phosphine-Pallalium Complex as a Catalyst in the Heck Arylation", J. Org. Chem, vol. 59, No. 18, 1994, pp. 5358-5364.

(Continued)

*Primary Examiner* — Karl J Puttlitz
(74) *Attorney, Agent, or Firm* — Venable LLP; Keith G. Haddaway; Lars H. Genieser

(57) ABSTRACT

A continuous carbonylation process for high turnover carbonylation, and a carbonylation reaction medium and product stream thereof. The process comprises carbonylating an ethlenically unsaturated compound with carbon monoxide in the presence of a source of hydroxyl groups and a catalyst system. The catalyst system comprising: (a) a bidentate phosphine, arsine or stibine ligand; and (b) a catalytic metal selected from a group VIB or group VIIIB metal or a compound thereof. The catalytically active concentration of said catalytic metal, measured as the ACCF (product $Kg \cdot hr^{-1} \cdot Dm^{-3}$), is maintained at less than 0.5.

10 Claims, 1 Drawing Sheet

(56) References Cited

U.S. PATENT DOCUMENTS

| | | |
|---|---|---|
| 4,900,413 A | 2/1990 | Sakakura et al. |
| 4,950,703 A | 8/1990 | Smutny |
| 4,960,926 A | 10/1990 | Drent |
| 4,960,949 A | 10/1990 | Devon et al. |
| 5,028,576 A | 7/1991 | Drent et al. |
| 5,099,062 A | 3/1992 | Drent et al. |
| 5,103,043 A | 4/1992 | Drent et al. |
| 5,149,868 A | 9/1992 | Drent |
| 5,158,921 A | 10/1992 | Drent et al. |
| 5,166,116 A | 11/1992 | Drent et al. |
| 5,177,253 A | 1/1993 | Drent et al. |
| 5,179,225 A | 1/1993 | Drent et al. |
| 5,189,003 A | 2/1993 | Klusener et al. |
| 5,210,280 A | 5/1993 | Drent |
| 5,245,098 A | 9/1993 | Summers et al. |
| 5,246,558 A | 9/1993 | Chevigne et al. |
| 5,258,546 A | 11/1993 | Klusener et al. |
| 5,350,876 A | 9/1994 | Drent et al. |
| 5,369,074 A | 11/1994 | Drent |
| 5,436,356 A | 7/1995 | Drent et al. |
| 5,563,308 A | 10/1996 | Spindler et al. |
| 5,710,344 A | 1/1998 | Breikss et al. |
| 5,719,313 A | 2/1998 | Drent et al. |
| 5,760,264 A | 6/1998 | Brieden |
| 5,773,661 A | 6/1998 | Unruh et al. |
| 5,783,715 A | 7/1998 | Pugin |
| 5,962,732 A | 10/1999 | Burke |
| 6,015,919 A | 1/2000 | Pugin |
| 6,156,934 A | 12/2000 | Suykerbuyk et al. |
| 6,169,192 B1 | 1/2001 | Pugin et al. |
| 6,191,284 B1 | 2/2001 | Knochel et al. |
| 6,232,262 B1 | 5/2001 | Sielcken et al. |
| 6,258,979 B1 | 7/2001 | Kagan et al. |
| 6,284,919 B1 | 9/2001 | Pearson et al. |
| 6,284,925 B1 | 9/2001 | Knochel et al. |
| 6,307,065 B1 | 10/2001 | Tjaden et al. |
| 6,335,471 B1 | 1/2002 | Eastham et al. |
| 6,337,406 B1 | 1/2002 | Zhang |
| 6,348,621 B1 | 2/2002 | Wang et al. |
| 6,391,818 B1 | 5/2002 | Bonsel et al. |
| 6,462,095 B1 | 10/2002 | Bonsel et al. |
| 6,476,255 B1 | 11/2002 | Hadden et al. |
| 6,521,769 B1 | 2/2003 | Zhang |
| 6,706,912 B2 | 3/2004 | Drent et al. |
| 6,723,882 B2 | 4/2004 | Slany et al. |
| 6,737,542 B1 | 5/2004 | Drent et al. |
| 6,743,911 B2 | 6/2004 | Drent et al. |
| 6,753,450 B2 | 6/2004 | Ahlers et al. |
| 6,844,463 B2 | 1/2005 | Slany et al. |
| 6,916,954 B2 | 7/2005 | Schafer et al. |
| 6,982,357 B2 | 1/2006 | Crabtree et al. |
| 6,984,668 B1 | 1/2006 | Eastham et al. |
| 7,026,473 B2 | 4/2006 | Drent et al. |
| 7,129,367 B2 | 10/2006 | Suzuki et al. |
| 7,148,176 B2 | 12/2006 | Beller et al. |
| 7,265,240 B2 * | 9/2007 | Eastham et al. ............ 560/175 |
| 7,371,705 B2 | 5/2008 | Eastham et al. |
| 2001/0044556 A1 | 11/2001 | Drent et al. |
| 2001/0051745 A1 | 12/2001 | Pearson et al. |
| 2002/0016484 A1 | 2/2002 | Drent et al. |
| 2002/0045748 A1 | 4/2002 | Drent et al. |
| 2003/0191339 A1 | 10/2003 | Schfer et al. |
| 2004/0110989 A1 | 6/2004 | Slany et al. |
| 2004/0115475 A1 | 6/2004 | Hashimoto |
| 2004/0162440 A1 | 8/2004 | Bunel et al. |
| 2005/0090694 A1 | 4/2005 | Drent et al. |
| 2006/0106259 A1 | 5/2006 | Eastham et al. |
| 2006/0122435 A1 | 6/2006 | Eastham et al. |
| 2006/0128985 A1 * | 6/2006 | Eastham et al. ............ 560/179 |
| 2006/0235241 A1 | 10/2006 | Drent et al. |
| 2006/0252935 A1 | 11/2006 | Eastham et al. |
| 2008/0086015 A1 | 4/2008 | Eastham |
| 2008/0269459 A1 | 10/2008 | Drent et al. |
| 2008/0269520 A1 | 10/2008 | Drent et al. |
| 2009/0216041 A1 | 8/2009 | Eastham et al. |
| 2009/0234126 A1 | 9/2009 | Hartwig et al. |
| 2009/0312561 A1 | 12/2009 | Eastham et al. |
| 2010/0030036 A1 | 2/2010 | Mottram et al. |
| 2010/0197958 A1 | 8/2010 | Eastham et al. |
| 2010/0324332 A1 | 12/2010 | Carrington-Smith et al. |

FOREIGN PATENT DOCUMENTS

| | | |
|---|---|---|
| CN | 1478071 A | 2/2004 |
| CN | 101137611 A | 3/2008 |
| CN | 101142162 A | 3/2008 |
| DE | 19745904 A1 | 4/1999 |
| DE | 19754304 A1 | 6/1999 |
| DE | 10023470 A1 | 11/2001 |
| DE | 10037961 A1 | 2/2002 |
| EP | 0 055 875 A1 | 7/1982 |
| EP | 0 106 379 A1 | 4/1984 |
| EP | 121965 A2 | 10/1984 |
| EP | 0144118 | 6/1985 |
| EP | 181014 A1 | 5/1986 |
| EP | 213671 A1 | 3/1987 |
| EP | 0 227 160 A2 | 7/1987 |
| EP | 0 235 864 A1 | 9/1987 |
| EP | 0 274 795 A2 | 7/1988 |
| EP | 0 282 142 A1 | 9/1988 |
| EP | 0 305 089 A1 | 3/1989 |
| EP | 0375573 A1 | 6/1990 |
| EP | 0 386 833 A1 | 9/1990 |
| EP | 0 441 447 A1 | 8/1991 |
| EP | 0 489 472 A2 | 6/1992 |
| EP | 0 495 547 A2 | 7/1992 |
| EP | 0 495 548 A2 | 7/1992 |
| EP | 0495347 A1 | 7/1992 |
| EP | 0495348 A1 | 7/1992 |
| EP | 0 499 329 A1 | 8/1992 |
| EP | 0 577 205 A2 | 1/1994 |
| EP | 0683764 A1 | 11/1995 |
| EP | 0 728 733 A1 | 8/1996 |
| EP | 0879642 A2 | 11/1998 |
| EP | 1330309 A1 | 7/2003 |
| FR | 2034147 A5 | 12/1970 |
| GB | 2006208 A | 5/1979 |
| JP | 06-065148 A | 3/1994 |
| JP | 08134218 A | 5/1996 |
| JP | 10 339929 A | 12/1998 |
| JP | 2001-517218 A | 10/2001 |
| JP | 2003-528849 A | 9/2003 |
| JP | 2004-515487 A | 5/2004 |
| JP | 2004-515537 A | 5/2004 |
| JP | 2009-533409 A | 9/2009 |
| KR | 2000-0076427 | 12/2000 |
| KR | 10-0851423 B1 | 8/2008 |
| TW | 524801 B | 3/2003 |
| TW | 552257 B | 9/2003 |
| TW | 200416212 | 9/2004 |
| TW | 200404773 | 4/2010 |
| WO | WO 96/19434 A | 6/1996 |
| WO | WO-9708124 A1 | 3/1997 |
| WO | WO-98/41495 A1 | 9/1998 |
| WO | WO 98/41495 A1 | 9/1998 |
| WO | WO-98/45040 | 10/1998 |
| WO | WO-9842717 | 10/1998 |
| WO | WO 99/47528 A | 9/1999 |
| WO | WO-00/56695 A1 | 9/2000 |
| WO | WO 01/10551 A1 | 2/2001 |
| WO | WO-01/28972 A1 | 4/2001 |
| WO | WO-01/65583 A1 | 9/2001 |
| WO | WO-01/68583 | 9/2001 |
| WO | WO-0168583 A2 | 9/2001 |
| WO | WO-0170659 | 9/2001 |
| WO | WO-01/72697 | 10/2001 |
| WO | WO-01/85662 A2 | 11/2001 |
| WO | WO-0187899 A1 | 11/2001 |
| WO | WO-0212161 | 2/2002 |
| WO | WO-02/46143 A1 | 6/2002 |
| WO | WO-02/48094 A1 | 6/2002 |
| WO | WO-03/040159 | 5/2003 |
| WO | WO 03/070370 A | 8/2003 |
| WO | WO-03070370 A1 | 8/2003 |

(56) References Cited

FOREIGN PATENT DOCUMENTS

| WO | WO 2004/014552 A | 2/2004 |
|---|---|---|
| WO | WO 2004/014834 A | 2/2004 |
| WO | WO 2004/024322 A2 | 3/2004 |
| WO | WO-2004/028689 A2 | 4/2004 |
| WO | WO 2004/050599 A | 6/2004 |
| WO | WO-200450599 A1 | 6/2004 |
| WO | WO-2004/072088 A2 | 8/2004 |
| WO | WO-2004/103948 | 12/2004 |
| WO | WO-2004/103948 A1 | 12/2004 |
| WO | WO 2005/003070 A | 1/2005 |
| WO | WO 2005/079981 A1 | 9/2005 |
| WO | WO-2005/082830 | 9/2005 |
| WO | WO-200582830 A1 | 9/2005 |
| WO | WO-2005118519 A1 | 12/2005 |
| WO | WO-2006/062467 A1 | 6/2006 |
| WO | WO-2006/084892 A2 | 8/2006 |
| WO | WO-2007/020379 A1 | 2/2007 |
| WO | WO-2007109365 A2 | 9/2007 |
| WO | WO-2007/119079 A1 | 10/2007 |
| WO | WO-2007119079 A1 | 10/2007 |
| WO | WO-2008/075108 A1 | 6/2008 |
| WO | WO-2008145976 A1 | 12/2008 |
| WO | WO-2009010782 A1 | 1/2009 |

OTHER PUBLICATIONS

Hofmann et al., "Bis(Di-T-Butylphosphino)Methane Complexes of Rhodium: Homogeneous Alkyne Hydrosilylation by Catalyst-Dependent Alkyne Insertion Into Rh—Si or Rh—H Bonds. Molecular Structures of the Dimer [(dtbpm) RHcL]$_2$ and of the Silyl Complex (dtbpm) Rh[Si(OEt)$^3$](PMe$_3$)", Journal of Organometallic Chemistry, vol. 490, 1995, pp. 51-70.

Lindner et al., "Catalytic Activity of Cationic Diphospalladium (II) Complexes in the Alkene/Co Copolymerization in Organic Solvents and Water in Dependence on the Length of the Alkyl Chain at the Phosphine Ligands", Journal of Organometallic Chemistry, vol. 602, 2000, pp. 173-187.

Richmond et al., "Preparation of New Catalysts by the Immobilization of Palladium(II) Species Onto Silica: An Investigation of Their Catalytic Activity for the Cyclization of Aminoalkynes", J. Am Chem. Soc., vol. 123, 2001, pp. 10521-10525.

Tamao et al., "Alkyl Group Isomerization in the Cross-Coupling Reaction of Secondary Alkyl Grignard Reagents With Organic Halides in the Presence of Nickel-Phosphine Complexes as Catalysts", Journal of the American Chemical Society, vol. 94, 1972, pp. 9268-9269.

Jones et al, "Rhodium-Catalyzed Activation and Functionalization of the C—C Bond of Biphenylene", Organometallics, vol. 20, 2001, pp. 5745-5750.

"Highly active [Pd(AcO)$_2$(dppp(] catalyst for the CO—C$_2$H$_4$ copolymerization in H$_2$O—CH$_3$COOH solvent [dppp = 1,3-bis(diphenylphosphino)propane]" Andrea Vavasori et al., Journal of Molecular Cat. A. Chem., vol. 204-205, 2003, pp. 295-303.

"Hydroesterification of styrene using an in situ formed Pd(OTs)$_2$(PPh$_3$)$_2$ complex catalyst", A. Seayad et al., Journal of Molecular Cat. A. Chem., vol. 151, 2000, pp. 47-59.

"Carbon monoxide-ethylene copolymerization catalyzed by a Pd(AcO)$_2$/dpppTsOH[1] system: the promoting effect of water and of the acid", Journal of Molecular Cat. A. Chem., vol. 110, 1996, pp. 13-23.

Kirk Othmer Encyclopaedia of Chemical Terminology, vol. 9, 4th Ed., p. 783, Hydrolysis of Organic Esters, pp. 783-85 and 87, John Wiley & Sons, Jan. 1994.

Masters, Christopher, "Homogeneous Transition Metal Catalysis," p. 4-21, Chapman and Hall, Feb. 1981.

Lide et al., Handbook of Chem and Phys., 76th Ed., CRC Press, 1995, ps. 8-141 6-155 to 6-177; 15-16 to 15-25.

Clegg, W. et al: "Highly active and selective catalysts for the production of methl propanoate via the methoxycarbonylation of ethene" Chem. Commun., 1999, pp. 1877-1878.

Knight et al: "Remarkable Differences in Catalyst Activity and Selectivity fo rthe production of Methyl Propanoate versus CO-Ethylene Copolymer by a Series of palladium Complexes of Related C$_4$-Bridged Diphosphines" Organometallics 2000, 19 4957-4967.

Rucklidge et al.: "Methoxycarbonylation f vinyl acetate catalysed by palladium comlexes of bis )ditertiarybutylphosphinomethyl) benzene and related ligands" Chem. Commun., 2005, pp. 1176-1178.

Brunkan et al. "Effect of chiral cavities associated with molecularly imprinted platinum centers on the selectivity of ligand-exchange reactions at platinum", Journal of American Chemical Society, No. 22, pp. 6217-6225, (2000).

Brunkan et al. "Unorthodox C,O binding mode of Me$_2$BINOL in Pt(II) complexes", Journal of American Chemical Society, No. 120, pp. 11002-11003, (1998).

Andrews et al. "Regioselective complexation of unprotected carbohydrates by Platinum(II); Synthesis, structure, complexation equilibria, and hydrogen-bonding in carbonate-derived bis(phosphine)platinum(II) diolate and alditolate complexes", Journal of American Chemical Society, No. 116, pp. 5730-5740, (1994).

Hartwig, et al. "Structure and reactions of oxametallacyclobutanes and oxametallacyclobutenes of ruthenium", Organometallics, vol. 10, No. 9, pp. 3344-3362 (1991).

Konno et al. "Preparation and spectroscopic characteristics of geometrical isomers of bis[1,2-bis(dimethylphosphino)ethane]cobalt(III) complexes with thiolate ligands", The Chemical Society of Japan, No. 62, pp. 3475-3478, (1989).

Cecconi et al. "Palladium complexes with the tripodal phosphine tris(2-diphenylphosphinoethyl)amine. Synthesis and structure of trigonal, tetrahedral, trigonal bipyramidal, and square planar complexes", J. Chem. Soc. Dalton Trans., issue 1, pp. xvii-xx. (1989).

Miskowski et al. "Preparation and spectroscopic properties of Cobalt(III) complexes containing phosphine ligands. The electronic structural description of side-bonded dioxygen", Journal of American Chemical Society, vol. 98, No. 9, pp. 2477-2483, (1976).

Hayward et al. "Some reactions of peroxobis (triphenylphosphine)platinum(II) and analogs with carbon dioxide, carbon disulfide, and other unsaturated molecules", Journal of American Chemical Society, vol. 92, issue 20, pp. 5873-5878, (1970).

Osman, Serindag "Synthesis of some platinum(II) diphosphine complexes of the type [PtX2(P-P)] (X2 = CO3; X = CH3COO, CF3COO, NCO)", Synth. React. lnorg. Met.-Org. Chem., vol. 27. No. 1, pp. 69-76, (1997).

Andrews et al. "Syntheses, spectra and structures of (diphosphine)platinum(II) carbonate complexes" Inorganic Chemistry, No. 35, pp. 5478-5483, (1996).

Latif et al. "Square planar platinum(II) complexes, crystal structures of cis-bis(triphenylphosphine) hydro(triphenylstannyl) platinum(II) and cis-bis(triphenylphosphine) hydro(triphenylsilyl) platinum(II)", Journal of Organometallic Chemistry, No. 474, pp. 217-221, (1994).

Becker et al. "Synthesis and characterization of chiral diphosphine platinum(II) VANOL and VAPOL complexes", Organometallics, No. 22, pp. 3245-3249, (2003).

Becker et al. "Imprinting chiral information into rigidified dendrimers", Organometallics, No. 22, pp. 4984-4998, (2003).

Peng et al. "Chiral rodlike platinum complexes, double helical chains and potential asymmetric hydrogenation ligand based on "linear" building blocks: 1,8,9,16-tetrahydroxytetraphenylene and 1,8,9,16-tetrakis(diphenylphosphino)tetraphenylene" Journal of American Chemical Society, No. 127, pp. 9603-9611, (2005).

Wen et al. "Synthesis, resolution, and applications of 1,16-dihydroxytetraphenylene as a novel building block in molecular recognition and assembly", Journal of Organic Chemistry, No. 68, pp. 8918-8931, (2003).

Mikami et al. "Molecular design of DABNTf as a highly efficient resolving reagent for racemic Pd complex with tropos biphenylphosphine (BIPHEP) ligand: circular dichroism (CD) spectra of enantiopure BIPHEP-Pd complex", Chirality, No. 15, pp. 105-107, (2003).

Tudor et al. "Diasteroisomer interconversion in chiral BiphepPtX2 complexes", Organometallics, No. 19, pp. 4376-4384, (2000).

(56) References Cited

OTHER PUBLICATIONS

Bellabarba et al., "Synthesis, X-ray characterization and reactions of a trigonal planar palladium()) carbonyl complex", Chemical Communications, No. 15, pp. 1916-1917, (2003).
Clegg et al., "Synthesis and reactivity of palladium hydrido-solvento complexes, including a key intermediate in the catalytic methoxycarbonylation of ethane to methypropanoate", Journal of the Chemical Society, Dalton Transactions, No. 17, pp. 3300-3308 (2002).
Clegg et al., "Characterisation and dynamics of [Pd(L-L)H(solv)]+, [Pd(L-L(CH2CH3)]+ and [Pd(L-L)(C(0)Et)(THF)]+ (L-L = 1,2-(CH2PBut2)2C6H4): key intermediates in the catalytic methoxycarbonylation of ethane to methylpropanoate", Organometallics, vol. 21, No. 9, pp. 1832-1840 (2002).
Edelbach et al., "Catalytic hydrogenolysis of biphenylene with platinum, palladium, and nickelphosphine complexes", Organometallics, vol. 17, No. 22, pp. 4784-4794 (1998).
Kim et al., "Synthesis and theoretical study of palladium (II) complexes with aminophosphines as 7-membered chelate rings", Bulletin of the Korean Chemical Society, vol. 18, No. 11, pp. 1162-1166 (1997).
Reddy et al., "Unexpected cross-metathesis between Si—C and Si—Si bonds", Chemical Communications, No. 16, pp. 1865-1866 (1996).
Uchimaru et al., "Ring-opening polymerization of 1,1,2,2-tetramethyl-1,2-disilacyclopentane via palladium complex-catalysed Si—Si bond metathesis", Chemistry Letters, No. 2, p. 164 (1995).
Portnoy et al., "Reactions of electron-rich arylpalladium complexes with olefins. Origin of the chelate effect in vinylation catalysis", Organometallics, vol. 13, No. 9, pp. 3465-3479 (1994).
Wurst et al., "Synthesis and structure of the platinum (0) compounds [(dipb)Pt]2(COD) and (dipb)3Pt2 and of the cluster Hg6[Pt(dipb)]4 (dipb = (iPr)2P(CH2)4P(i-Pr)2)", Zeitschrift Für Anorganische Und Allgemeine Chemie, vol. 395, pp. 239-250 (1991).
Tanaka et al., "Synthesis of ketones via carbonylation of organic halides. II. Palladium-catalysed carbonylation of organic halides with terminal acetylenes in the presence of amines. Novel acetylenic ketone synthesis", Nippon Kagaku Kaishi, No. 3, pp. 537-546 (1985).
Molander et al., "Synthesis and application of chiral cyclopropane-based ligands in palladium-catalyzed allylic alkylation", Journal of Organic Chemistry, vol. 69, No. 23, pp. 8062-8069 (2004).
Brauer et al., "Reactions of coordinated ligands. XIV. Synthesis of a tetradentate phosphorus macrocycle in a palladium (II) template", Chemische Berichte, vol. 119, No. 1, pp. 349-365 (1986).
Dias et al., "Synthesis and characterization of .eta.5-monocyclopentadienyl (p-nitrobenzonitrile)ruthenium(II) salts: second harmonic generation powder efficiencies", Journal of Organometallic Chemistry, vol. 475, No. 1-2, pp. 241-245 (1994).
Pugh, R. I. et al. "Tandem isomerisation-carbonylation catalysis: highly active palladium(II) catalysts for the selective methoxycarbonylation of internal alkenes to linear esters", Chemical Communications—CHEMCOM, Royal Society of Chemistry, GB, No. 16, (Aug. 21, 2001), pp. 1476-1477.
Cullen et al, "Structure of the Hydrogenation Catalyst [(PP)Rh(NBD)]ClO4, (PP) = ( 5-[(CH3)3C]2PC5H4)2Fe, and Some Comparative Rate Studies," Organometallics, vol. 2, pp. 714-719, 1983.
Abbenhuis et al., "Successful Application of a "Forgotten" Phosphine in Asymmetric Catalysis: A 9-Phosphabicyclo[3.3.1]non-9-yl Ferrocene Derivative as a Chiral Ligand," Organometallics, vol. 14, pp. 759-766, 1995.
Related U.S. Appl. No. 10/524,023, filed Nov. 17, 2005, Eastham et al.
Olah, George A., et al., "AlCl3-Catalyzed Dichlorophosphorylation of Saturated Hydrocarbons with PCl3 in Methylene Chloride Solution," *J. Org. Chem.*, 1990, 55, 1224-1227.
Wei-Yong Yu, et al., "Preparation of Polymer-Protected Pt/Co Bimetallic Colloid and its Catalytic Properties in Selective Hydrogenation of Cinnamaldehyde to Cinnamyl Alcohol," Polymers FOR Advanced Technologies, GB, John Wiley and Sons, Chichester, Aug. 1, 1996, 719-722, vol. 7, No. 8.
Office Action issued by the USPTO for U.S. Appl. No. 10/589,971, filed Jul. 27, 2010.
Office Action issued by the USPTO in U.S. Appl. No. 12/518,320, filed Dec. 8, 2010.
Oblad et al., Catalysis and Catalysts. In McKetta ed, *Encyclopedia of Chemical Processing and Design*, pp. 420-490, 1978.
Hartley, Supported Metal Complexes: A New Generation of Catalysts, Section 1.3, pp. 1, 9, 1985.
Armor, "Perspective: Do you really have a better catalyst?," Applied Catalysis A: General, vol. 282, pp. 1-4, 2005.
Hagen, "Industrial Catalysis: A Practical Approach," pp. v-xvii and 1-6, 2006.
Office Action for U.S. Appl. No. 11/990,272, issued by the USPTO on Jul. 12, 2011.
Office Action for U.S. Appl. No. 10/589,971, issued by the USPTO on Mar. 22, 2011.
Office Action for U.S. Appl. No. 12/084,575, issued by the USPTO on Aug. 29, 2011.
Doherty et al., "Selectivity for the methoxycarbonylation of ethylene versus CO-ethylene copolymerization with catalysts based on C4-bridged bidentate phosphines and phospholes," Journal of Organometallic Chemistry, vol. 640, pp. 182-196, 2001.
Dörwald, Side Reactions in Organic Synthesis: A Guide to Successful Synthesis Design, Weinheim—Wiley-VCH, pp. ix, 1-16, 2005.
Office Action for European Application No. 07848735.2, issued by the EPO on Sep. 9, 2011.
First Examination Report issued in Indian Application No. 841/MUMNP/2009 dated Nov. 29, 2012.
Notice of Allowance issued in U.S. Appl. No. 12/297,023 dated Dec. 26, 2012.
Notice of Allowance issued in U.S. Appl. No. 12/297,023 dated Feb. 21, 2013.
Office Action issued in Canadian Application No. 2,618,574 dated Dec. 7, 2012.
Office Action issued in Canadian Application No. 2,626,107 dated Nov. 23, 2012.
Office Action issued in Chinese Application No. 200580011699.0 dated Jan. 14, 2013.
Office Action issued in European Application No. 09 772 854.7 dated Oct. 5, 2012.
Office Action issued in Japanese Application No. 2008-540675 dated Nov. 13, 2012.
Office Action issued in Japanese Application No. 2009-538795 dated Feb. 19, 2013.
Office Action issued in Taiwanese Application No. 095128759 dated Jan. 3, 2013.
Office Action issued in Taiwanese Application No. 096113047 dated Jan. 22, 2013.
Office Action issued in U.S. Appl. No. 13/002,406 dated Mar. 15, 2013.
Office Action issued in Chinese Application No. 200780044657.6 dated Mar. 20, 2013.
Office Action issued in Malaysian Application No. PI20092250 dated Mar. 29, 2013.
Office Action issued in Taiwanese Application No. 096145458 dated Mar. 8, 2013.
Office Action issued in Korean Application No. 10-2008-7006106 dated Apr. 24, 2013.
Office Action issued in Chinese Application No. 200980125824.9 dated Feb. 22, 2013.
Office Action issued in European Application No. 09 772 854.7 dated Apr. 23, 2013.
Office Action issued in Eurasian Application No. 201170142, 2013.
Office Action issued in Mexican Application No. MX/a/2008/001974 dated Mar. 11, 2013.
Office Action for Taiwanese Application No. 095141340 issued by the Intellectual Property Office of Taiwan and received on Apr. 12, 2013.

(56) References Cited

OTHER PUBLICATIONS

Examination Report issued from the State Intellectual Property Office of P.R. China issued in Application No. GCC/P/2007/9585 dated Jan. 20, 2012.
Notice of Reason for Rejection issued from the Japanese Office Action in Japanese Application No. 2006-553662 dated Sep. 25, 2012.
Notice of Reason for Rejection issued from the Japanese Office Action in Japanese Application No. 2008-525618 dated Sep. 25, 2012.
Notice of Reasons for Rejection issued from the Japanese Patent Office in Japanese Application No. 2009-504833 dated Jul. 31, 2012.
Notice of Reexamination issued from the Patent Reexamination Board of State Intellectual Property Office of P.R. China in Chinese Application No. 200580011699.0 dated Jul. 30, 2012.
Office Action issued from the Eurasian Patent Organization issued in Application No. 200970528/28 dated Aug. 15, 2012.
Office Action for Australian Application No. 2006314268, issued by the Australian Patent Office on Nov. 11, 2010.
Office Action for European Application No. 07824927.3, issued by the EPO on Mar. 30, 2011.
Office Action for GCC Application No. GCC/P/2007/8136 issued by the State Intellectual Property Office of the P.R. China on Nov. 5, 2010.
Office Action for Chinese Application No. 200580011699.0 issued by the State Intellectual Property Office of the P.R. China on Jun. 23, 2011.
Office Action for Japanese Application based on International Application No. PCT/GB2005/000569 issued by the Patent Office of Japan on Jun. 21, 2011.
Office Action for U.S. Appl. No. 12/297,023, issued by the USPTO on Sep. 27, 2011.
Office Action for U.S. Appl. No. 12/518,320, issued by the USPTO on Dec. 6, 2011.
Office Action for Taiwanese Application No. 094104929 issued by the Intellectual Property Office of Taiwan on Sep. 21, 2011.
Office Action for U.S. Appl. No. 12/084,575, issued by the USPTO on Mar. 19, 2012.
Office Action for U.S. Appl. No. 12/297,023, issued by the USPTO on Apr. 12, 2012.
Office Action for U.S. Appl. No. 12/517,215, issued by the USPTO on Feb. 27, 2012.
Andrews et al., "Syntheses, Spectra, and Structures of (Diphosphine)platinum(II) Carbonate Complexes," Inorganic Chemistry, vol. 35, No. 19, pp. 5478-5483, 1996.
Office Action issued in Korean Patent Office on Jan. 12, 2012, English translation.
Argouarch, et al., "Synthesis of Some Ferrocene-Based 1,3(phosphanes) with Planar Chirality as the Sole Source of Chirality", European Journal of Organic Chemistry, 2000, vol. 16 pp. 2885-2891.
Examination Report issued by the State Intellectual Property Office of the P.R. China in Application No. GCC/P/2007/8136 dated Nov. 5, 2010.
Examiner's First Report issued in Australian Application No. 2007327051 dated May 9, 2012.
Godard, et al., "Systematic Study of the Asymmetric Methoxycarbonylation of Styrene Catalyzed by Palladium Systems Containing Chiral Ferrocenyl Diphosphine Ligands", Helvetica Chimica Acta, 2006 vol. 89(8) pp. 1610-1622.
Gray et al., "The Di-t-Butylphosphinyl Directed *ortho* Metalation Group, Synthesis of Hindered Dialkylarylphosphines," Synlett Letters, vol. 4, pp. 422-424 (1998).
International Preliminary Report on Patentability issued in Application No. PCT/GB2010/052093 dated Jun. 28, 2012.
International Search Report issued in International Application No. PCT/GB2009/050780 dated Oct. 15, 2009.
International Search Report issued in International Application No. PCT/GB2010/052093 dated Apr. 8, 2011.

International Search Report issued in International Application No. PCT/GB2010/052214 dated Mar. 30, 2011.
Japanese Notice of Reasons for Rejection issued in Application No. 2008-525618 dated Apr. 3, 2012.
Japanese Notice of Reasons for Rejection issued in Application No. 2008-540675 dated May 22, 2012.
Kraatz et al., "The reactions of tridentate cationic palladium (II) complexes with olefins and nucleophiles," The Journal of Organometallic Chemistry, vol. 488, No. 1, pp. 223-232 (1995).
Ooka et al., "Highly active and selective palladium catalyst for hydroesterification of styrene and vinyl acetate promoted by polymeric sulfonic acids," Chemical Communications, pp. 1173-1175 (2005).
Rucklidge, et al., "Methoxycarbonylation of vinyl acetate catalysed by palladium complexes of bis(ditertiarybutylphosphinomethyl) benzene and related ligands", Chemical Communications, 2005, vol. 9 pp. 1176-1178.
Russian Office Action issued in Application No. 201170142/28 dated Apr. 20, 2012.
United Kingdom Search Report issued in Application No. GB 1000078.4 dated May 6, 2010.
United Kingdom Search Report issued in Application No. GB0812297.0 dated Jun. 17, 2009.
United Kingdom Search Report issued in Application No. GB0921876.9 dated Oct. 29, 2010.
Wang, et al., "Synthesis and Use in Asymmetric Hydrogenations of Solely Planar Chiral 1,2-Disubstituted and 1,2,3-Trisubstituted Ferrocenyl Diphosphines: A Comparative Study", Organometallics, 2007, vol. 26, pp. 3530-3540.
Written Opinion of the International Searching Authority issued in International Application No. PCT/GB2009/050780 dated Oct. 15, 2009.
Written Opinion of the International Searching Authority issued in International Application No. PCT/GB2010/052093 dated Apr. 8, 2011.
Written Opinion of the International Searching Authority issued in International Application No. PCT/GB2010/052214 dated Mar. 30, 2011.
Tolman, "Phosphorous Ligand Exchange Equilibria on Zerovalent Nickel. A Dominant Role for Steric Effects," Journal of the American Chemical Society, vol. 92, No. 10, pp. 2956-2965.
Tolman, "Steric Effects of Phosphorous Ligands in Organometallic Chemistry and Homogeneous Catalysis," Chemical Reviews, vol. 77, No. 3, pp. 313-348.
Grimmer, et al., "Zirconium *bis*-cyclopentadienyl compounds: An investigation into the influence of substituent effects on the ethene polymerisation behaviour of $(CpR)_2ZrCl_2$/MAO catalysts," Journal of Molecular Catalysis A: Chemical, vol. 188, No. 1-2, pp. 105-113, 2002.
Machine Translation of JP 08-134218, May 28, 1996.
Office Action for U.S. Appl. No. 11/597,787, issued by the USPTO on Oct. 8, 2008.
Office Action for U.S. Appl. No. 11/597,787, issued by the USPTO on Oct. 8, 2009.
Office Action for U.S. Appl. No. 11/597,787, issued by the USPTO on May 20, 2009.
Office Action for U.S. Appl. No. 10/561,912, issued by the USPTO on Aug. 25, 2008.
Office Action for U.S. Appl. No. 10/561,912, issued by the USPTO on Sep. 2, 2009.
Office Action for U.S. Appl. No. 10/561,912, issued by the USPTO on Jan. 14, 2008.
Office Action for U.S. Appl. No. 10/561,912, issued by the USPTO on Feb. 11, 2009.
Office Action for U.S. Appl. No. 10/536,801, issued by the USPTO on Apr. 8, 2008.
Office Action for U.S. Appl. No. 10/536,801, issued by the USPTO on Jan. 7, 2010.
Office Action for U.S. Appl. No. 10/536,801, issued by the USPTO on Jun. 17, 2009.
Kiss, "Palladium-catalyzed Reppe Carbonylation," Chem. Rev. 2001, 101(11): 3435 (Abstract Only).

(56) References Cited

OTHER PUBLICATIONS

Office Action issued in Indian Application No. 1366/DELNP/2003 dated Jul. 4, 2013.
Office Action issued in Mexican Application No. MX/a/2010/014404 dated Jun. 25, 2013.
Office Action issued in U.S. Appl. No. 10/589,971 dated Aug. 8, 2013.
Office Action issued in U.S. Appl. No. 13/002,406 dated Aug. 19, 2013.
White et al., "Basic Energy Sciences Advisory Committee Subpanel Workshop Report," Opportunities for Catalysis in the 21st Century, 2002, pp. 1-47.
Written Opinion of the Intellectual Property Office of Singapore issued in Application No. 201204384-0 dated Jul. 5, 2013.
Letter Reporting Office Action issued in Australian Application No. 2009265367 dated Aug. 20, 2013.
Office Action issued in Canadian Application No. 2,626,107 dated Aug. 8, 2013.
Office Action issued in Canadian Application No. 2,671,409 dated Aug. 23, 2013.
Office Action issued in Chinese Application No. 200780044657.6 dated Sep. 23, 2013.
Office Action issued in Eurasian Application No. 200801345 dated Jul. 27, 2013.
Office Action issued in Eurasian Application No. 201170142/28 dated Aug. 23, 2013.
Office Action issued in Eurasian Application No. 201290605 dated Aug. 22, 2013.
Office Action issued in Indian Application No. 3292/DELNP/2008 dated Sep. 20, 2013.
Office Action issued in Malaysian Application No. PI2011000006 dated Sep. 30, 2013.
Letter Reporting Office Action issued in Mexican Application No. MX/a/2009/005568 dated Sep. 12, 2013.
Office Action issued in Singapore Application No. SE 2013 01311V dated Aug. 9, 2013.

* cited by examiner

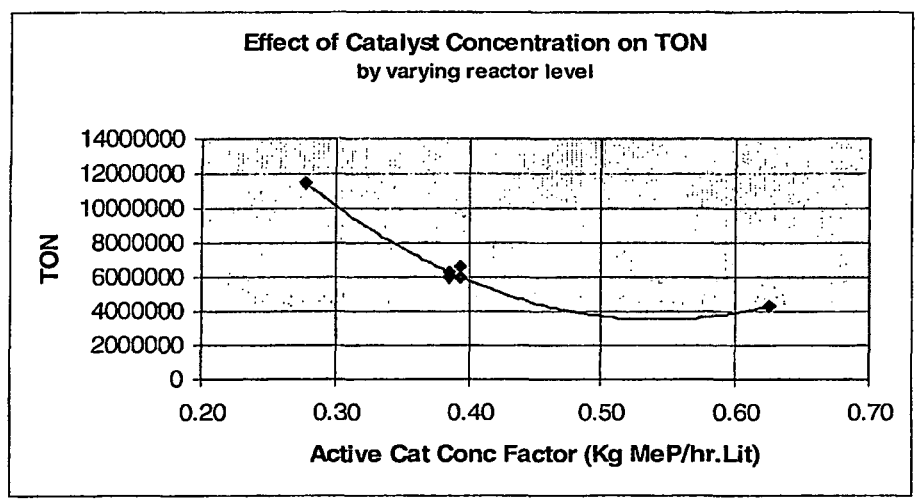

CATALYST SYSTEM

The present invention relates to a process for the carbonylation of ethylenically unsaturated compounds, a novel carbonylation reaction medium and a process for the carbonylation of ethylenically unsaturated compounds using a novel carbonylation reaction medium.

The carbonylation of ethylenically unsaturated compounds using carbon monoxide in the presence of an alcohol or water and a catalyst system comprising a Group VIII metal, eg. palladium, and a phosphine ligand eg. an alkyl phosphine cycloalkyl phosphine, aryl phosphine, pyridyl phosphine or bidentate phosphine, has been described in numerous European patents and patent applications, eg. EP-A-0055875, EP-A-04489472, EP-A-0106379, EP-A-0235864, EP-A-0274795, EP-A-0499329, EP-A-0386833, EP-A-0441447, EP-A-0489472, EP-A-0282142, EP-A-0227160, EP-A-0495547 and EP-A-0495548. In particular, EP-A-0227160, EP-A-0495547 and EP-A-0495548 disclose that bidentate phosphine ligands provide catalyst systems which enable higher reaction rates to be achieved.

A greater improvement to such bidentate phosphine ligands is provided in WO 96/19434 which discloses a bridging group in the form of an optionally substituted aryl moiety, linked to the said phosphorous atoms via available adjacent carbon atoms on the said aryl moiety. Such a ligand is more stable and leads to reaction rates which are significantly higher than those previously disclosed and produces little or no impurities for the carbonylation of ethylene. Each phosphorous atom in the said ligand is also linked to two tertiary carbon atoms.

However, conventional metal-catalysed reactions, such as those described in WO 96/19434 tend to suffer from the drawback that the catalyst tends to de-activate over the course of a period of continuous operation as the palladium compound is reduced to palladium metal, thus contributing an important factor in the economic viability of the process. WO 01/10551 addressed this problem via the use of stabilising compounds such as polymeric dispersants in the reaction medium, thus improving the recovery of metal which has been lost from the catalyst system. Interestingly, however, none of the examples actually relate to a continuous process and, therefore, little knowledge of the effect on recovery of metal or other factors can be obtained from the disclosure.

Although catalyst systems have been developed which exhibit reasonable stability during the carbonylation process and permit relatively high reaction rates to be achieved, there still exists a need for improved catalyst activity. Suitably, the present invention aims to provide, inter alia, an improved continuous process for carbonylation of ethylenically unsaturated compounds and a carbonylation reaction medium for such continuous processes for carbonylating ethylenically unsaturated compounds. In particular, improvements to bidentate phosphine ligand containing catalyst systems are sought.

Palladium and other precious metals in Group VIB or Group VIIIB are expensive commodities and as mentioned above the rate of use of this commodity contributes to the economic viability of carbonylation processes using such metals. One expression of the efficiency of the use of the catalytic metal is turnover number (TON) which is defined as Moles of Carbonylation Product/Moles of Catalytic Metal. A high TON number indicates a more efficient and cost effective process. In the past efforts have concentrated on high rates of production of carbonylation product to maximise yield in this respect.

Catalyst activity per unit volume of reaction medium can be expressed in terms of the production of carbonylation product per unit time from a unit volume of reaction medium, and is measured in units of product $kg \cdot hr^{-1} \cdot dm^{-3}$. This measure is known as the active catalyst concentration factor (ACCF).

According to a first aspect of the present invention there is provided a continuous carbonylation process for high turnover carbonylation comprising carbonylating an ethylenically unsaturated compound with carbon monoxide in the presence of a source of hydroxyl groups and a catalyst system comprising (a) a bidentate phosphine, arsine or stibine ligand, and (b) a catalytic metal selected from a group VIB or group VIIIB metal or a compound thereof wherein the catalytically active concentration of said catalytic metal, measured as the ACCF (product $Kg \cdot hr^{-1} \cdot dm^{-3}$) is held at less than 0.5.

By continuous herein is meant that the respective concentrations of ethylenically unsaturated compound, carbon monoxide, the source of hydroxyl groups and, preferably, the catalyst system are held substantially constant during the process.

According to a second aspect of the present invention there is provided a carbonylation reaction medium and product stream thereof for a continuous carbonylation process comprising in the reaction medium an ethylenically unsaturated compound, carbon monoxide, a source of hydroxyl groups and a catalyst system comprising:—
  (a) a bidentate phosphine, arsine or stibene ligand, and
  (b) a catalytic metal selected from a group VIB or group VIIIB metal or a compound thereof wherein the catalytically active concentration of said catalytic metal in said medium, measured as the ACCF (product $kg \cdot hr^{-1} \cdot dm^{-3}$), is maintained at less than 0.5.

For the avoidance of doubt, the ACCF of the carbonylation reaction medium for a continuous process is generally measured in the product stream.

Preferred features of the invention will be apparent from the dependent claims, and the description which follows.

Preferably, the ACCF is less than 0.4, more preferably, less than 0.35, most preferably, less than 0.30.

Typically, the ACCF range is 0.005 to 0.49, more typically 0.01 to 0.39, most typically, 0.05 to 0.34. Especially preferred is an ACCF of 0.1 to 0.29 $kg \cdot dm^{-3} \cdot hr^{-1}$.

Typically, the low ACCF of the present invention is held or maintained by suitable dilution of the carbonylation reaction medium. Preferably, dilution is effected with one of the components of the reaction medium other than the catalyst metal, more preferably, by means of an additional solvent, carbonylation product or hydroxyl group containing compound. The carbonylation product, when capable of acting as a solvent is particularly preferred.

Preferably, the catalyst system also includes as a further component (c) an acid.

By "acid", we mean an acid or salt thereof, and references to acid should be construed accordingly.

Suitably, all of components a), b) and c) (when present) of the catalyst system can be added in situ to the reaction vessel wherein the carbonylation is to take place. Alternatively, the components a), b) and c) (when present) can be added sequentially in any order to form the catalyst system, or in some specified order, either directly into the vessel or outside the vessel and then added to the vessel. For instance, the acid component c) (when present) may first be added to the bidentate ligand component a), to form a protonated ligand, and then the protonated ligand can be added to the metal or compound thereof (component b)) to form the catalyst system. Alternatively, the ligand component a) and metal or compound thereof (component b)) can be mixed to form a chelated metal compound, and the acid (component c)) is then optionally added. Alternatively, when the acid component c) is to be used, any two components can be reacted together to form an intermediate moiety which is then either added to the reaction vessel and the third component added, or is first reacted with the third component and then added to the reaction vessel. However, in the continuous process it is preferred that the components a), b) and c) are all added independently of each other at a continuous rate.

The present invention is also directed to a catalyst system as defined above wherein the relative molar concentrations of both the bidentate ligand and the acid are at levels in excess of those previously envisaged, leading to surprising and unexpected advantages when using the catalyst system in the carbonylation of ethylenically unsaturated compounds, and the alleviation or at least reduction of at least some of the disadvantages of the prior art systems. In any case, the use of a catalyst system of the present invention leads at least to a more stable system, with improved turnover numbers in carbonylation reactions of ethylenically unsaturated compounds.

The amount of bidentate ligand used can vary within wide limits. Preferably, the bidentate ligand is present in an amount such that the ratio of the number of moles of the bidentate ligand present to the number of moles of the Group VIB or VIIIB metal present is from 1 to 50 eg. 1 to 10 and particularly from 1 to 5 mol per mol of metal. More preferably, the mol:mol range of compounds of formula I to Group VIIIB metal is in the range of 1:1 to 3:1, most preferably in the range of 1:1 to 1.25:1. Conveniently, the possibility of applying these low molar ratios is advantageous, as it avoids the use of an excess of the compound of formula I and hence minimises the consumption of these usually expensive compounds. Suitably, the catalysts of the invention are prepared in a separate step preceding their use in-situ in the carbonylation reaction of an ethlenically unsaturated compound.

However, in an excess acid system the ligand may be present in the catalyst system, or precursor thereto, in excess so that the ratio of said ligand to the said metal (i.e. component a) to component b)) is at least a 2:1 molar ratio. Preferably, the ratio of said ligand to the said metal in such systems is greater than a 2:1 molar ratio, more preferably in the range 2:1 to 1000:1, even more preferably in the range 2.5:1 to 1000:1, yet more preferably in the range 3:1 to 1000:1, even more preferably in the range 5:1 to 750:1, more preferably in the range 7:1 to 1000:1, especially in the range 8:1 to 900:1, still more preferably in the range 10:1 to 500:1, yet still more preferably in the range 20:1 to 400:1, even more preferably in the range 50:1 to 250:1, most preferably in the range in excess of 50:1, for example 51:1 and upwards, more specifically 51:1 to 250:1 or even to 1000:1. Alternatively, the said ratio can be in the range 15:1 to 45:1, preferably 20:1 to 40:1, more preferably 25:1 to 35:1.

As stated above, acid may be present and this may be in excess in the catalyst system, or precursor thereto, preferably, in such quantity that the ratio of said acid to the said ligand (i.e. component c) to component a)) is at least a 2:1 molar ratio. Preferably, the ratio of said acid to the said ligand in such excess acid systems is greater than a 2:1 molar ratio, more preferably in the range 2:1 to 100:1, even more preferably in the range 4:1 to 100:1, yet more preferably in the range 5:1 to 95:1, still more preferably in the range greater than 5:1 to 95:1, yet more preferably in the range greater than 5:1 to 75:1, more preferably in the range 10:1 to 50:1, even more preferably in the range 20:1 to 40:1, still more preferably in the range greater than 20:1 to 40:1 (e.g. 25:1 to 40:1, or 25:1 to less than 30:1), more preferably in excess of 30:1, suitably with any of the upper limits provided hereinbefore (e.g. 30:1 to 40:1), or 50:1, etc.), or more preferably in excess of 35:1, yet more preferably in excess of 37:1, suitably either with any of the upper limits provided hereinbefore. Each of the ranges in this paragraph can be used in conjunction with each of the ligand to metal ratio ranges disclosed hereinabove, i.e. ratios of component a) to component b).

The advantages in working within the ligand to metal, and acid to ligand ratios, set out above in an excess acid system are manifest in that the stability of the catalyst system is further improved over that surprisingly provided by the low ACCF, as evidenced by further increases in the turnover number (TON) of the metal. By improving the stability of the catalyst system, the usage of metal in the carbonylation reaction scheme is kept to a minimum.

In effect, the level of acid should be such that for the particular bidentate ligand employed, the level of acid should be such that phosphine, arsine or stibine is fully protonated. Hence, to show the improved effects, the level of ligand should be above some minimum level, as given by the ligand:metal molar ratio, and the level of acid should be above some minimum level with respect to the level of ligand present to encourage protonation, as given by the acid:ligand molar ratio.

Preferably, the acid is present in the catalyst system, or precursor thereto, in such quantity that the molar ratio of said acid to said metal (i.e. component c) to component b)) in the excess acid system is at least 4:1, more preferably from 4:1 to 100000:1, even more preferably 10:1 to 75000:1, yet more preferably 20:1 to 50000:1, yet still more preferably 25:1 to 50000:1, yet still more preferably 30:1 to 50000:1, yet even more preferably 40:1 to 40000:1, still more preferably 100:1 to 25000:1, more preferably 120:1 to 25000:1, more preferably 140:1 to 25000:1, yet still more preferably 200:1 to 25000:1, most preferably 550:1 to 20000:1, or greater than 2000:1 to 20000:1. Alternatively, the said ratio can be in the range 125:1 to 485:1, more preferably 150:1 to 450:1, even more preferably 175:1 to 425:1, yet even more preferably 200:1 to 400:1, most preferably 225:1 to 375:1. Each of these ranges in this paragraph can be used in conjunction with each of the ligand to metal ratio ranges disclosed hereinabove, i.e. ratios of component a) to component b), and/or each of the acid to ligand ratio ranges disclosed hereinabove, i.e. ratios of component c) to component a).

For the avoidance of any doubt, all of the aforementioned ratios and ratio ranges apply to all of the ligand embodiments set out in more detail hereinafter. However, it should also be borne in mind that the presence of acid is optional and not essential to the present invention. Accordingly, the possibility of excess acid in the system is also optional and not essential to the present invention.

The advantages of the ACCF aspects of the invention, set out above are manifest in that the stability of the catalyst system is improved, as evidenced by increases in the turnover number (TON) of the metal. By improving the stability of the catalyst system, the usage of metal in the carbonylation reaction scheme is kept to a minimum.

In one embodiment of the present invention, the bidentate phosphine ligand is of general formula (I)

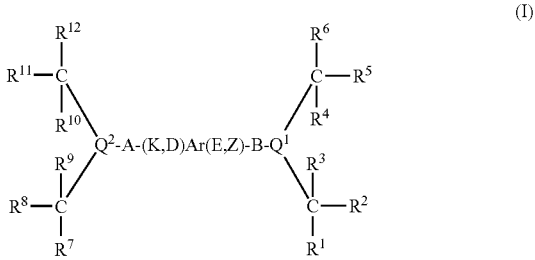

(I)

wherein:
Ar is a bridging group comprising an optionally substituted aryl moiety to which the phosphorus atoms are linked on available adjacent carbon atoms;
A and B each independently represent lower alkylene;
K, D, E and z are substituents of the aryl moiety (Ar) and each independently represent hydrogen, lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$, $C(O)SR^{27}$, or $-J-Q^3(CR^{13}(R^{14})(R^{15})CR^{16}(R^{17})(R^{18})$ where J represents lower alkylene; or two adjacent groups selected from K, Z, D and E together with the carbon atoms of the aryl ring to which they are attached form a further phenyl ring, which is optionally substituted by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{27}$;
$R^{13}$ to $R^{18}$ each independently represent hydrogen, lower alkyl, aryl, or Het, preferably each independently represent lower alkyl, aryl, or Het;
$R^{19}$ to $R^{27}$ each independently represent hydrogen, lower alkyl, aryl or Het;
$R^1$ to $R^{12}$ each independently represent hydrogen, lower alkyl, aryl, or Het, preferably each independently represent lower alkyl, aryl, or Het;
$Q^1$, $Q^2$ and $Q^3$ (when present) each independently represent phosphorous, arsenic or antimony and in the latter two cases references to phosphine or phosphorous above are amended accordingly, with preferably both $Q^1$ and $Q^2$ representing phosphorus, more preferably all of $Q^1$, $Q^2$ and $Q^3$ (when present) representing phosphorus.

Suitably, the bidentate phosphines of the invention should preferably be capable of bidentate coordination to the Group VIB or Group VIIIB metal or compound thereof, more preferably to the preferred palladium.

Preferably, when K, D, E or Z represent $-J-Q^3(CR^{13}(R^{14})(R^{15}))CR^{16}(R^{17})(R^{18})$, the respective K, D, E or Z is on the aryl carbon adjacent the aryl carbon to which A or B is connected or, if not so adjacent, is adjacent a remaining K, D, E or Z group which itself represents $-J-Q^3(CR^{13}(R^{14})(R^{15}))CR^{16}(R^{17})(R^{18})$.

Specific but non-limiting examples of bidentate ligands within this embodiment include the following: 1,2-bis-(di-tert-butylphosphinomethyl)benzene, 1,2-bis-(di-tert-pentylphosphinomethyl)benzene, 1,2-bis-(di-tert-butylphosphinomethyl)naphthalene. Nevertheless, the skilled person in the art would appreciate that other bidentate ligands can be envisaged without departing from the scope of the invention.

The term "Ar" or "aryl" when used herein, includes five-to-ten-membered, preferably, six-to-ten membered carbocyclic aromatic groups, such as phenyl and naphthyl, which groups are optionally substituted with, in addition to K, D, E or Z, one or more substituents selected from aryl, lower alkyl (which alkyl group may itself be optionally substituted or terminated as defined below), Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$ or $C(S)NR^{25}R^{26}$ wherein $R^{19}$ to $R^{27}$ each independently represent hydrogen, aryl or lower alkyl (which alkyl group may itself be optionally substituted or terminated as defined below). Furthermore, the aryl moiety may be a fused polycyclic group, e.g. naphthalene, biphenylene or indene.

By the term "a metal of Group VIB or Group VIIIB" in a compound of formula I we include metals such as Cr, Mo, W, Fe, Co, Ni, Ru, Rh, Os, Ir, Pt and Pd. Preferably, the metals are selected from Ni, Pt and Pd. More preferably, the metal is Pd. For the avoidance of doubt, references to Group VIB or VIIIB metals herein should be taken to include Groups 6, 8, 9 and 10 in the modern periodic table nomenclature.

The term "Het", when used herein, includes four-to-twelve-membered, preferably four-to-ten-membered ring systems, which rings contain one or more heteroatoms selected from nitrogen, oxygen, sulphur and mixtures thereof, and which rings may contain one or more double bonds or be non-aromatic, partly aromatic or wholly aromatic in character. The ring systems may be monocyclic, bicyclic or fused. Each "Het" group identified herein is optionally substituted by one or more substituents selected from halo, cyano, nitro, oxo, lower alkyl (which alkyl group may itself be optionally substituted or terminated as defined below) $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$ or $C(S)NR^{25}R^{26}$ wherein $R^{19}$ to $R^{27}$ each independently represent hydrogen, aryl or lower alkyl (which alkyl group itself may be optionally substituted or terminated as defined below). The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

The term "lower alkyl" when used herein, means $C_1$ to $C_{10}$ alkyl and includes methyl, ethyl, propyl, butyl, pentyl, hexyl and heptyl groups. Unless otherwise specified, alkyl groups may, when there is a sufficient number of carbon atoms, be linear or branched, be saturated or unsaturated, be cyclic, acyclic or part cyclic/acyclic, and/or be substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, aryl or Het, wherein $R^{19}$ to $R^{27}$ each independently represent hydrogen, aryl or lower alkyl, and/or be interrupted by one or more oxygen or sulphur atoms, or by silano or dialkylsilicon groups.

Lower alkyl groups or alkyl groups which $R^1$, $R^2$, $R^3$, $R^4$, $R^5$, $R^6$, $R^7$, $R^8$, $R^9$, $R^{10}$, $R^{11}R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, K, D, E and Z may represent and with which aryl and Het may be substituted, may, when there is a sufficient number of carbon atoms, be linear or branched, be saturated or unsaturated, be cyclic, acyclic or part cyclic/acyclic, and/or be interrupted by one or more of oxygen or sulphur atoms, or by silano or dialkylsilicon groups, and/or be substituted by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, aryl or Het wherein $R^{19}$ to $R^{27}$ each independently represent hydrogen, aryl or lower alkyl.

Similarly, the term "lower alkylene" which A, B and J (when present) represent in a compound of formula I, when used herein, includes $C_1$ to $C_{10}$ groups which are bonded to other moieties at least at two places on the group and is otherwise defined in the same way as "lower alkyl".

Halo groups with which the above-mentioned groups may be substituted or terminated include fluoro, chloro, bromo and iodo.

Where a compound of a formula herein contains an alkenyl group, cis (E) and trans (z) isomerism may also occur. The present invention includes the individual stereoisomers of the compounds of any of the formulas defined herein and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound one of the formulas or a suitable salt or derivative thereof. An individual enantiomer of a compound of one of the formulas may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

All stereoisomers are included within the scope of the process of the invention.

It will be appreciated by those skilled in the art that the compounds of formula I may function as ligands that coordinate with the Group VIB or Group VIIIB metal or compound thereof in the formation of the catalyst system of the invention. Typically, the Group VIB or Group VIIIB metal or compound thereof coordinates to the one or more phosphorous, arsenic and/or antimony atoms of the compound of formula I.

Preferably, $R^1$ to $R^{18}$ each independently represent lower alkyl or aryl. More preferably, $R^1$ to $R^{18}$ each independently represent $C_1$ to $C_6$ alkyl, $C_1$-$C_6$ alkyl phenyl (wherein the phenyl group is optionally substituted as defined herein) or phenyl (wherein the phenyl group is optionally substituted as defined herein). Even more preferably, $R^1$ to $R^{18}$ each independently represent $C_1$ to $C_6$ alkyl, which is optionally substituted as defined herein. Most preferably, $R^1$ to $R^{18}$ each represent non-substituted $C_1$ to $C_6$ alkyl such as methyl, ethyl, n-propyl, iso-propyl, n-butyl, iso-butyl, tert-butyl, pentyl, hexyl and cyclohexyl.

Alternatively, or additionally, each of the groups $R^1$ to $R^3$, $R^4$ to $R^6$, $R^7$ to $R^9$, $R^{10}$ to $R^{12}$, $R^{13}$ to $R^{15}$ or $R^{16}$ to $R^{18}$ together independently may form cyclic structures such as 1-norbornyl or 1-norbornadienyl. Further examples of composite groups include cyclic structures formed between $R^1$-$R^{18}$. Alternatively, one or more of the groups may represent a solid phase to which the ligand is attached.

In a particularly preferred embodiment of the present invention $R^1$, $R^4$, $R^7$, $R^{10}$, $R^{13}$ and $R^{16}$ each represent the same lower alkyl, aryl or Het moiety as defined herein, $R^2$, $R^5$, $R^8$, $R^{11}$, $R^{14}$ and $R^{17}$ each represent the same lower alkyl, aryl or Het moiety as defined herein, and $R^3$, $R^6$, $R^9$, $R^{12}$, $R^{15}$ and $R^{18}$ each represent the same lower alkyl, aryl or Het moiety as defined herein. More preferably $R^1$, $R^4$, $R^7$, $R^{10}$, $R^{13}$ and $R^{16}$ each represent the same $C_1$-$C_6$ alkyl, particularly non-substituted $C_1$-$C_6$ alkyl, such as methyl, ethyl, n-propyl, iso-propyl, n-butyl, iso-butyl, tert-butyl, pentyl, hexyl or cyclohexyl; $R^2$, $R^5$, $R^8$, $R^{11}$, $R^{14}$ and $R^{17}$ each independently represent the same $C_1$-$C_6$ alkyl as defined above; and $R^3$, $R^6$, $R^9$, $R^{12}$, $R^{15}$ and $R^{18}$ each represent the same $C_1$-$C_6$ alkyl as defined above. For example: $R^1$, $R^4$, $R^7$, $R^{10}$, $R^{13}$ and $R^{16}$ each represent methyl; $R^2$, $R^5$, $R^8$, $R^{11}$, $R^{14}$ and $R^{17}$ each represent ethyl; and, $R^3$, $R^6$, $R^9$, $R^{12}$, $R^{15}$ and $R^{18}$ each represent n-butyl or n-pentyl.

In an especially preferred embodiment of the present invention each $R^1$ to $R^{18}$ group represents the same lower alkyl, aryl, or Het moiety as defined herein. Preferably, each $R^1$ to $R^{18}$ represents the same $C_1$ to $C_6$ alkyl group, particularly non-substituted $C_1$-$C_6$ alkyl, such as methyl, ethyl, n-propyl, iso-propyl, n-butyl, iso-butyl, tert-butyl, pentyl, hexyl and cyclohexyl. Most preferably each $R^1$ to $R^{18}$ represents methyl.

In the compound of formula I, preferably each $Q^1$, $Q^2$ and $Q^3$ (when present) are the same. Most preferably, each $Q^1$, $Q^2$ and $Q^3$ (when present) represents phosphorous.

Preferably, in the compound of formula I, A, B and J (when present) each independently represent $C_1$ to $C_6$ alkylene which is optionally substituted as defined herein, for example with lower alkyl groups. Preferably, the lower alkylene groups which A, B and J (when present) represent are non-substituted. A particular preferred lower alkylene which A, B and J may independently represent is —$CH_2$— or —$C_2H_4$—. Most preferably, each of A, B and J (when present) represent the same lower alkylene as defined herein, particularly —$CH_2$—.

Preferably, in the compound of formula I when K, D, E or Z does not represent -J-$Q^3(CR^{13}(R^{14})(R^{15}))CR^{16}(R^{17})(R^{18})$, K, D, E or Z represents hydrogen, lower alkyl, phenyl or lower alkylphenyl. More preferably, K, D, E or Z represent hydrogen, phenyl, $C_1$-$C_6$ alkylphenyl or $C_1$-$C_6$ alkyl, such as methyl, ethyl, propyl, butyl, pentyl and hexyl. Most preferably, K, D, E or Z represents hydrogen.

Preferably, in the compound of formula I when K, D, E and Z together with the carbon atoms of the aryl ring to which they are attached do not form a phenyl ring, K, D, E and Z each independently represent hydrogen, lower alkyl, phenyl or lower alkylphenyl. More preferably, K, D, E and Z each independently represent hydrogen, phenyl, $C_1$-$C_6$ alkylphenyl or $C_1$-$C_6$ alkyl, such as methyl, ethyl, propyl, butyl, pentyl and hexyl. Even more preferably, K, D, E and Z represent the same substituent. Most preferably, they represent hydrogen.

Preferably, in the compound of formula I when K, D, E or Z does not represent -J-$Q^3(CR^{13}(R^{14})(R^{15}))CR^{16}(R^{17})(R^{18})$ and K, D, E and Z together with the carbon atoms of the aryl ring to which they are attached do not form a phenyl ring, each of K, D, E and Z represent the same group selected from hydrogen, lower alkyl, aryl, or Het as defined herein; particularly hydrogen or $C_1$-$C_6$ alkyl (more particularly unsubstituted $C_1$-$C_6$ alkyl), especially hydrogen.

Preferably, in the compound of formula I when two of K, D, E and Z together with the carbon atoms of the aryl ring to which they are attached form a phenyl ring, then the phenyl ring is optionally substituted with one or more substituents selected from aryl, lower alkyl (which alkyl group may itself be optionally substituted or terminated as defined below), Het, halo, cyano, nitro, $OR^{19}$, $OC(O)R^{20}$, $C(O)R^{21}$, $C(O)OR^{22}$, $NR^{23}R^{24}$, $(O)NR^{25}R^{26}$, $SR^{27}$, $C(O)SR^{27}$ or $C(S)NR^{25}R^{26}$ wherein $R^{19}$ to $R^{27}$ each independently represent hydrogen or lower alkyl (which alkyl group may itself be optionally substituted or terminated as defined herein). More preferably, the phenyl ring is not substituted by any substituents i.e. it bears hydrogen atoms only.

Preferred compounds of formula I include those wherein: A and B each independently represent unsubstituted $C_1$ to $C_6$ alkylene; K, D, Z and E each independently represent hydrogen, $C_1$-$C_6$ alkyl, phenyl, $C_1$-$C_6$ alkylphenyl or -J-$Q^3(CR^{13}(R^{14})(R^{15}))CR^{16}(R^{17})(R^{18})$ where J represents unsubstituted $C_1$ to $C_6$ alkylene; or two of K, D, Z and E together with the carbon atoms of the aryl ring to which they are attached form a phenyl ring which is optionally substituted by one or more substituents selected from lower alkyl, phenyl or lower alkylphenyl.
$R^1$ to $R^{18}$ each independently represent $C_1$ to $C_6$ alkyl, phenyl or $C_1$ to $C_6$ alkylphenyl.

Further preferred compounds of formula I include those wherein:
A and B both represent —$CH_2$— or $C_2H_4$, particularly $CH_2$;
K, D, Z and E each independently represent hydrogen, $C_1$-$C_6$ alkyl phenyl or $C_1$-$C_6$ alkyl or -J-$Q^3(CR^{13}(R^{14})(R^{15}))CR^{16}(R^{17})(R^{18})$ where J is the same as A; or two of K, D, E and Z together with the carbon atoms of the aryl ring to which they are attached form an unsubstituted phenyl ring;
$R^1$ to $R^{18}$ each independently represent $C_1$ to $C_6$ alkyl;

Still further preferred compounds of formula I include those wherein:
$R^1$ to $R^{18}$ are the same and each represents $C_1$ to $C_6$ alkyl, particularly methyl.

Still further preferred compounds of formula I include those wherein:
K, D, Z and E are each independently selected from the group consisting of hydrogen or $C_1$ to $C_6$ alkyl, particularly where each of K, D, Z and E represent the same group, especially where each of K, D, Z and E represent hydrogen; or
K represents —$CH_2$-$Q^3(CR^{13}(R^{14})(R^{15}))CR^{16}(R^{17})(R^{18})$ and D, Z and E are each independently selected from the group consisting of hydrogen or $C_1$ to $C_6$ alkyl, particularly where both D and E represent the same group, especially where D, Z and E represent hydrogen.

Especially preferred specific compounds of formula I include those wherein:
each $R^1$ to $R^{12}$ is the same and represents methyl;
A and B are the same and represent —$CH_2$—;
K, D, Z and E are the same and represent hydrogen.

In a still further embodiment, at least one $(CR^xR^yR^z)$ group attached to $Q^1$ and/or $Q^2$, i.e. $CR^1R^2R^3$, $CR^4R^5R^6$, $CR^7R^8R^9$, or $CR^{10}R^{11}R^{12}$, may instead be represented by the group (Ad) wherein:
Ad each independently represent an optionally substituted adamantyl or congressyl radical bonded to the phosphorous atom via any one of its tertiary carbon atoms, the said optional substitution being by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{22}$, $C(O)NR^{25}R^{26}$, $C(S)R^{25}R^{26}$, $SR^{27}$ or $C(O)SR^{27}$; or both $(CR^xR^yR^z)$ groups attached to either or both $Q^1$ and/or $Q^2$, or $Q^3$ (if present), form an optionally substituted 2-phospha-tricyclo[3.3.1.1{3,7}]decyl group (also termed a 2-phospha-adamantyl group (2-PA-group)) or derivative thereof as more particularly defined hereinafter, or form a ring system of formula

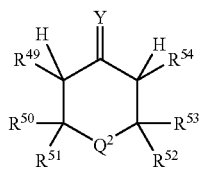

wherein
$R^{49}$, and $R^{54}$, each independently represent hydrogen, lower alkyl or aryl;
$R^{50}$ to $R^{53}$, when present, each independently represent hydrogen, lower alkyl, aryl or Het; and
Y represents oxygen, sulfur or N—$R^{55}$; and $R^{55}$, when present, represents hydrogen, lower alkyl or aryl.

In this embodiment, formula I may be represented as:

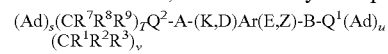

wherein Ar, A, B, K, D, E and Z, $Q^1$, $Q^2$, and $Q^3$, and $R^1$ to $R^{27}$ are as defined hereinbefore except that K, D, E and Z may represent -J-$Q^3(Ad)_w(CR^{13}(R^{14})(R^{15})_x$ instead of -J-$Q^3(CR^{13}(R^{14})(R^{15}))CR^{16}(R^{17})(R^{18})$ and Ad is as defined above,
S & U=0, 1 or 2 provided that S+U≥1;
T & V=0, 1 or 2 provided that T+V≤3;
W & X=0, 1 or 2.

In addition to the preferred embodiments for $R^1$ to $R^{18}$, $Q^1$ to $Q^3$, A, B, J (when present), K, D, E or Z, $R^{19}$ to $R^{27}$, noted hereinbefore, all of which equally apply to the present embodiment where at least one (Ad) group is present, the following also applies.

Further preferred compounds of formula I include those wherein:
A and B both represent —$CH_2$— or $C_2H_4$—, particularly —$CH_2$—;
K, D, Z and E each independently represent hydrogen, $C_1$-$C_6$ alkyl phenyl or $C_1$-$C_6$ alkyl or -J-$Q^3$ $(Ad)_w(CR^{13}(R^{14})(R^{15}))_x$ where J is the same as A; or two of K, D, E and Z together with the carbon atoms of the aryl ring to which they are attached form an unsubstituted phenyl ring;
$R^1$ to $R^3$, $R^7$ to $R^9$, and $R^{13}$ to $R^{15}$ (when present) each independently represent $C_1$ to $C_6$ alkyl, and the total number of (Ad) groups attached to $Q^1$ and $Q^2$ is ≥3, i.e. S+U≥3, and W and X=0, 1 or 2.

Still further preferred compounds of formula I include those wherein:
$R^1$ to $R^3$, $R^7$ to $R^9$ and $R^{13}$ to $R^{15}$ (when present) are the same and each represents $C_1$ to $C_6$ alkyl, particularly methyl, and the total number of (Ad) groups attached to $Q^1$ and $Q^2$ is ≥3, i.e. S+U≥3.

Still further preferred compounds of formula I include those wherein:
K, D, Z and E are each independently selected from the group consisting of hydrogen or $C_1$ to $C_6$ alkyl, particularly where each of K, D, Z and E represent the same group, especially where each of K, D, Z and E represent hydrogen; or
K represents —$CH_2$-$Q^3(Ad)_w(CR^{13}(R^{14})(R^{15}))$ and D, Z and E are each independently selected from the group consisting of hydrogen or $C_1$ to $C_6$ alkyl, particularly where both D and E represent the same group, especially where D, Z and E represent hydrogen, wherein W and X=0, 1 or 2.

Especially preferred specific compounds of formula I include those wherein:
each $R^1$ to $R^3$, and $R^7$ to $R^9$ is the same and represents methyl or the total number of (Ad) groups attached to $Q^1$ and $Q^2$ is 2, i.e. S+U=2;
A and B are the same and represent —$CH_2$—;
K, D, Z and E are the same and represent hydrogen.

Especially preferred specific compounds of formula I include those wherein Ad is joined to $Q_1$ or $Q_2$ at the same position in each case. Preferably S≥1 and U≥1, more preferably, S=2 and U≥1 or vice versa, most preferably S & U=2, wherein S is the number of (Ad) groups attached to $Q^2$ and U is the number of (Ad) groups attached to $Q^1$.

Specific but non-limiting examples of bidentate ligands within this embodiment include the following: 1,2 bis(diadamantylphosphinomethyl)benzene, 1,2 bis(di-3,5-dimethyladamantylphosphinomethyl)benzene, 1,2 bis(di-5-tert-butyladamantylphosphinomethyl)benzene, 1,2 bis(1-adamantyl, tert-butyl-phosphinomethyl)benzene, 1-(diadamantylphosphinomethyl)-2-(di-tert-butylphosphinomethyl)benzene, 1-(di-tert-butylphosphinomethyl)-2-(dicongressylphosphinomethyl)benzene, 1-(di-tert-butylphosphinomethyl)-2-

(phospha-adamantyl-P-methyl)benzene, 1-(diadamantylphosphinomethyl)-2-(phospha-adamantyl-P-methyl)benzene, 1-(tert-butyladamantylphosphinomethyl)-2-(diadamantylphosphinomethyl)benzene and 1-[(P-(2,2,6,6-tetra-methylphosphinan-4-one)phosphinomethyl)]-2-(phospha-adamantyl-P-methyl)benzene, wherein "phospha-adamantyl" is selected from 2-phospha-1,3,5,7-tetramethyl-6,9,10-trioxadamantyl, 2-phospha-1,3,5-trimethyl-6,9,10 trioxadamantyl, 2-phospha-1,3,5,7-tetra(trifluoromethyl)-6,9,10-trioxadamantyl or 2-phospha-1,3,5-tri(trifluoromethyl)-6,9,10-trioxadamantyl. Nevertheless, the skilled person in the art would appreciate that other bidentate ligands can be envisaged without departing from the scope of the invention.

In a yet further embodiment, the bidentate phosphine ligand is of general formula (III).

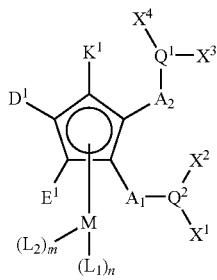

(III)

wherein:
$A_1$ and $A_2$, and $A_3$, $A_4$ and $A_5$ (when present), each independently represent lower alkylene;
$K^1$ is selected from the group consisting of hydrogen, lower alkyl, aryl, Het, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$C(S)(R^{27})R^{28}$, —$SR^{29}$, —$C(O)SR^{30}$, —$CF_3$ or -$A_3$-$Q^3$($X^5$)$X^6$;
$D^1$ is selected from the group consisting of hydrogen, lower alkyl, aryl, Het, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$C(S)(R^{27})R^{28}$, —$SR^{29}$, —$C(O)SR^{30}$, —$CF_3$ or -$A_4$-$Q^4$($X^7$)$X^8$;
$E^1$ is selected from the group consisting of hydrogen, lower alkyl, aryl, Het, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{23})R^{26}$, —$C(S)(R^{27})R^{28}$, —$SR^{29}$, —$C(O)SR^{30}$, —$CF_3$ or -$A_5$-$Q^5$($X^9$)$X^{10}$;
or both $D^1$ and $E^1$ together with the carbon atoms of the cyclopentadienyl ring to which they are attached form an optionally substituted phenyl ring:
$X^1$ represents $CR^1(R^2)(R^3)$, congressyl or adamantyl, $X^2$ represents $CR^4(R^5)(R^6)$ congressyl or adamantyl, or $X^1$ and $X^2$ together with $Q^2$ to which they are attached form an optionally substituted 2-phospha-tricyclo[3.3.1.1{3,7}]decyl group or derivative thereof, or $X^1$ and $X^2$ together with $Q^2$ to which they are attached form a ring system of formula IIIa

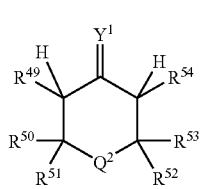

(IIIa)

$X^3$ represents $CR^7(R^8)(R^9)$, congressyl or adamantyl, $X^4$ represents $CR^{10}(R^{11})(R^{12})$, congressyl or adamantyl, or $X^3$ and $X^4$ together with $Q^1$ to which they are attached form an optionally substituted 2-phospha-tricyclo[3.3.1.1{3,7}]decyl group or derivative thereof, or $X^3$ and $X^4$ together with $Q^1$ to which they are attached form a ring system of formula IIIb

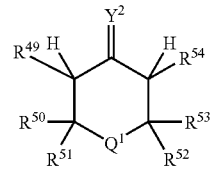

(IIIb)

$X^5$ represents $CR^{13}(R^{14})(R^{15})$, congressyl or adamantyl, $X^6$ represents $CR^{16}(R^{17})(R^{18})$, congressyl or adamantyl, or $X^5$ and $X^6$ together with $Q^3$ to which they are attached form an optionally substituted 2-phospha-tricyclo[3.3.1.1{3,7}]decyl group or derivative thereof, or $X^5$ and $X^6$ together with $Q^3$ to which they are attached form a ring system of formula IIIc

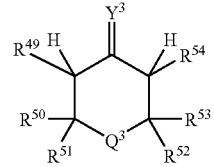

(IIIc)

$X^7$ represents $CR^{31}(R^{32})(R^{33})$, congressyl or adamantyl, $X^8$ represents $CR^{34}(R^{35})(R^{36})$, congressyl or adamantyl, or $X^7$ and $X^8$ together with $Q^4$ to which they are attached form an optionally substituted 2-phospha-tricyclo[3.3.1.1{3,7}]decyl group or derivative thereof, or $X^7$ and $X^8$ together with $Q^4$ to which they are attached form a ring system of formula IIId

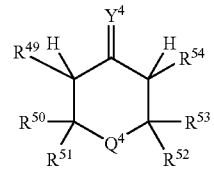

(IIId)

$X^9$ represents $CR^{37}(R^{38})(R^{39})$, congressyl or adamantyl, $X^{10}$ represents $CR^{40}(R^{41})(R^{42})$, congressyl or adamantyl, or $X^9$ and $X^{10}$ together with $Q^5$ to which they are attached form an optionally substituted 2-phospha-tricyclo[3.3.1.1.{3,7}]decyl group or derivative thereof, or $X^9$ and $X^{10}$ together with $Q^5$ to which they are attached form a ring system of formula IIIe

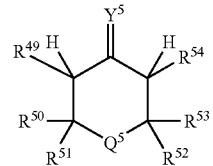

(IIIe)

and in this yet further embodiment,
$Q^1$ and $Q^2$, and $Q^3$, $Q^4$ and $Q^5$ (when present), each independently represent phosphorus, arsenic or antimony;

M represents a Group VIB or VIIIB metal or metal cation thereof;

$L_1$ represents an optionally substituted cyclopentadienyl, indenyl or aryl group;

$L_2$ represents one or more ligands each of which are independently selected from hydrogen, lower alkyl, alkylaryl, halo, CO, $P(R^{43})(R^{44})R^{45}$ or $N(R^{46})(R^{47})R^{48}$;

$R^1$ to $R^{18}$ and $R^{31}$ to $R^{42}$, when present, each independently represent hydrogen, lower alkyl, aryl, halo or Het;

$R^{19}$ to $R^{30}$ and $R^{43}$ to $R^{48}$, when present, each independently represent hydrogen, lower alkyl, aryl or Het;

$R^{49}$, $R^{54}$ and $R^{55}$, when present, each independently represent hydrogen, lower alkyl or aryl;

$R^{50}$ to $R^{53}$, when present, each independently represent hydrogen, lower alkyl, aryl or Het;

$Y^1$, $Y^2$, $Y^3$, $Y^4$ and $Y^5$, when present, each independently represent oxygen, sulfur or N—$R^{55}$;

n=0 or 1;

and m=0 to 5;

provided that when n=1 then m equals 0, and when n equals 0 then m does not equal 0.

Preferably in a compound of formula III when both $K^1$ represents -$A_3$-$Q^3(X^5)X^6$ and $E^1$ represents -$A_5$-$Q^5(X^9)X^{10}$, then $D^1$ represents -$A_4$-$Q^4(X^7)X^8$.

Preferably, in this embodiment, $R^1$ to $R^{18}$ and $R^{31}$ to $R^{42}$, when present, each independently represent hydrogen, optionally substituted $C_1$ to $C_6$ alkyl, $C_1$-$C_6$ alkyl phenyl (wherein the phenyl group is optionally substituted as defined herein), trifluoromethyl or phenyl (wherein the phenyl group is optionally substituted as defined herein). Even more preferably, $R^1$ to $R^{18}$ and $R^{31}$ to $R^{42}$, when present, each independently represent hydrogen, $C_1$ to $C_6$ alkyl, which is optionally substituted as defined herein, trifluoromethyl or optionally substituted phenyl. Even more preferably, $R^1$ to $R^{18}$ and $R^{31}$ to $R^{42}$, when present each independently represent hydrogen, non-substituted $C_1$ to $C_6$ alkyl or phenyl which is optionally substituted with one or more substituents selected from non-substituted $C_1$ to $C_6$ alkyl or $OR^{19}$ where $R^{19}$ represents hydrogen or unsubstituted $C_1$ to $C_6$ alkyl. More preferably, $R^1$ to $R^{18}$ and $R^{31}$ to $R^{42}$, when present, each independently represent hydrogen or non-substituted $C_1$ to $C_6$ alkyl such as methyl, ethyl, n-propyl, iso-propyl, n-butyl, iso-butyl, tert-butyl, pentyl, hexyl and cyclohexyl, especially methyl. Most preferably, $R^1$ to $R^{18}$ and $R^{31}$ to $R^{42}$ when present, each independently represent non-substituted $C_1$ to $C_6$ alkyl such as methyl, ethyl, n-propyl, iso-propyl, n-butyl, iso-butyl, tert-butyl, pentyl, hexyl and cyclohexyl, especially methyl.

Alternatively, or additionally, one or more of the groups $R^1$ to $R^3$, $R^4$ to $R^6$, $R^7$ to $R^9$, $R^{10}$ to $R^{12}$, $R^{13}$ to $R^{15}$, $R^{16}$ to $R^{18}$, $R^{31}$ to $R^{33}$, $R^{34}$ to $R^{36}$, $R^{37}$ to $R^{39}$ or $R^{40}$ to $R^{42}$ (when present) together with the carbon atom to which they are attached independently may form cyclic alkyl structures such as 1-norbornyl or 1-norbornadienyl.

Alternatively, or additionally, one or more of the groups $R^1$ and $R^2$, $R^4$ and $R^5$, $R^7$ and $R^8$, $R^{10}$ and $R^{11}$, $R^{13}$ and $R^{14}$, $R^{16}$ and $R^{17}$, $R^{31}$ and $R^{32}$, $R^{34}$ and $R^{35}$, $R^{37}$ and $R^{38}$ or $R^{40}$ and $R^{41}$ (when present) together with the carbon atom to which they are attached independently may form a cyclic alkyl structures, preferably a $C_5$ to $C_7$ cyclic alkyl structure such as cyclohexyl and cyclopentyl, and $R^3$, $R^6$, $R^9$, $R^{12}$, $R^{15}$, $R^{18}$ $R^{33}$, $R^{36}$, $R^{39}$ and $R^{42}$ (when present) each independently represent hydrogen, lower alkyl, trifluoromethyl or aryl as defined above, particularly non-substituted $C_1$ to $C_6$ alkyl and hydrogen, especially non-substituted $C_1$ to $C_6$ alkyl.

In an especially preferred embodiment, each of $R^1$ to $R^{18}$ and $R^{31}$ to $R^{42}$, when present, do not represent hydrogen.

Suitably, such an arrangement means $Q^1$, $Q^2$, $Q^3$, $Q^4$ and $Q^5$ are bonded to a carbon atom of $X^1$ to $X^{10}$, respectively, which bears no hydrogen atoms.

Preferably, $R^1$, $R^4$, $R^7$, $R^{10}$, $R^{13}$, $R^{16}$ $R^{31}$, $R^{34}$, $R^{37}$ and $R^{40}$ (when present), each represent the same substituent as defined herein; $R^2$, $R^5$, $R^8$, $R^{11}$, $R^{14}$, $R^{17}$, $R^{32}$, $R^{35}$, $R^{38}$ and $R^{41}$ (when present), each represent the same substituent as defined herein; and $R^3$, $R^6$, $R^9$, $R^{12}$, $R^{15}$, $R^{18}$, $R^{33}$, $R^{36}$, $R^{39}$ and $R^{42}$ (when present), each represent the same substituent as defined herein. More preferably $R^1$, $R^4$, $R^7$, $R^{10}$, $R^{13}$, $R^{16}$, $R^{31}$, $R^{34}$, $R^{37}$ and $R^{40}$ (when present) each represent the same $C_1$-$C_6$ alkyl, particularly non-substituted $C_1$-$C_6$ alkyl, such as methyl, ethyl, n-propyl, iso-propyl, n-butyl, iso-butyl, tert-butyl, pentyl, hexyl or cyclohexyl, or trifluoromethyl; $R^2$, $R^5$, $R^8$, $R^{11}$, $R^{14}$, $R^{17}$, $R^{32}$, $R^{35}$, $R^{38}$ and $R^{41}$ (when present), each independently represent the same $C_1$-$C_6$ alkyl as defined above, or trifluoromethyl; and $R^3$, $R^6$, $R^9$, $R^{12}$, $R^{15}$, $R^{18}$, $R^{33}$, $R^{36}$, $R^{39}$ and $R^{42}$ (when present), each independently represent the same $C_1$-$C_6$ alkyl as defined above, or trifluoromethyl. For example: $R^1$, $R^4$, $R^7$, $R^{10}$, $R^{13}$ and $R^{16}$ (when present) each represent methyl; $R^2$, $R^5$, $R^8$, $R^{11}$, $R^{14}$ and $R^{17}$ each represent ethyl (when present); and, $R^3$, $R^6$, $R^9$, $R^{12}$, $R^{15}$ and $R^{18}$ (when present) each represent n-butyl or n-pentyl.

In an especially preferred embodiment each $R^1$ to $R^{18}$ and $R^{31}$ to $R^{42}$ group (when present) represents the same substituent as defined herein. Preferably, each $R^1$ to $R^{18}$ and $R^{31}$ to $R^{42}$ group represents the same $C_1$ to $C_6$ alkyl group, particularly non-substituted $C_1$-$C_6$ alkyl, such as methyl, ethyl, n-propyl, iso-propyl, n-butyl, iso-butyl, tert-butyl, pentyl, hexyl and cyclohexyl, or trifluoromethyl. Most preferably, each $R^1$ to $R^{18}$ and $R^{31}$ to $R^{42}$ group represents non-substituted $C_1$-$C_6$ alkyl, particularly methyl.

The term adamantyl when used herein means an adamantyl group which may be bonded to $Q^1$, $Q^2$, $Q^3$, $Q^4$ and $Q^5$, respectively, in position 1 or 2. Tricyclo[3.3.1.1.{3,7}]decyl is the systematic name for an adamantyl group, suitably $Q^1$, $Q^2$, $Q^3$, $Q^4$ and $Q^5$, respectively, may be bonded to the 1 position or 2 position of one or two tricyclo[3.3.1.1.{3,7}]decyl groups. Preferably, $Q^1$ and $Q^2$, and $Q^3$, $Q^4$ and $Q^5$, when present, is bonded to a tertiary carbon of one or more adamantyl groups. Suitably, when the adamantyl group represents unsubstituted adamantyl, $Q^1$ and $Q^2$, and $Q^3$, $Q^4$ and $Q^5$ when present are preferably bonded to the 1 position of one or more tricyclo[3.3.1.1{3,7}]decyl groups i.e. the carbon atom of the adamantyl group bears no hydrogen atom.

The adamantyl group may optionally comprise, besides hydrogen atoms, one or more substituents selected from lower alkyl, —$OR^{19}$, —$OC(O)R^{20}$, halo, nitro, —$C(O)R^{21}$, —$C(O)OR^{22}$, cyano, aryl, —$N(R^{23})R^{24}$, —$C(O)N(R^{25})R^{26}$, —$C(S)(R^{27})R^{28}$, —$CF_3$, —$P(R^{56})R^{57}$, —$PO(R^{58})(R^{59})$, —$PO_3H_2$, —$PO(OR^{60})(OR^{61})$, or —$SO_3R^{62}$, wherein $R^{19}$, $R^{20}$, $R^{21}$, $R^{22}$, $R^{23}$, $R^{24}$, $R^{25}$, $R^{26}$, $R^{27}$, $R^{28}$, lower alkyl, cyano and aryl are as defined herein and $R^{56}$ to $R^{62}$ each independently represent hydrogen, lower alkyl, aryl or Het.

Suitably, when the adamantyl group is substituted with one or more substituents as defined above, highly preferred substituents include unsubstituted $C_1$ to $C_8$ alkyl, —$OR^{19}$, —$OC(O)R^{20}$, phenyl, —$C(O)OR^{22}$, fluoro, —$SO_3H$, —$N(R^{23})R^{24}$, —$P(R^{56})R^{57}$, —$C(O)N(R^{25})R^{26}$ and —$PO(R^{58})(R^{59})$, —$CF_3$, wherein $R^{19}$ represents hydrogen, unsubstituted $C_1$-$C_8$ alkyl or phenyl, $R^{20}$, $R^{22}$, $R^{23}$, $R^{24}$, $R^{25}$, $R^{26}$ each independently represent hydrogen or unsubstituted $C_1$-$C_8$ alkyl, $R^{56}$ to $R^{53}$, $R^{56}$ each independently represent unsubstituted $C_1$-$C_8$ alkyl or phenyl.

Suitably, the adamantyl group may comprise, besides hydrogen atoms, up to 10 substituents as defined above, preferably up to 5 substituents as defined above, more preferably up to 3 substituents as defined above. Suitably, when the adamantyl group comprises, besides hydrogen atoms, one or more substituents as defined herein, preferably each substituent is identical. Preferred substituents are unsubstituted $C_1$-$C_8$ alkyl and trifluoromethyl, particularly unsubstituted $C_1$-$C_8$ alkyl such as methyl. A highly preferred adamantyl group comprises hydrogen atoms only i.e. the adamantyl group is not substituted.

Preferably, when more than one adamantyl group is present in a compound of formula III, each adamantyl group is identical.

By the term 2-phospha-tricyclo[3.3.1.1.{3,7}]decyl group we mean a 2-phospha-adamantyl group formed by the combination of $X^1$ and $X^2$ together with $Q^2$ to which they are attached, a 2-phospha-adamantyl group formed by the combination of $X^3$ and $X^4$ together with $Q^1$ to which they are attached, a 2-phospha-adamantyl group formed by the combination of $X^5$ and $X^6$ together with $Q^3$ to which they are attached, a 2-phospha-adamantyl group formed by the combination of $X^7$ and $X^8$ together with $Q^4$ to which they are attached and a 2-phospha-adamantyl group formed by the combination of $X^9$ and $X^{10}$ together with $Q^5$ to which they are attached, wherein $Q^1$, $Q^2$, $Q^3$, $Q^4$ and $Q^5$ is in the 2 position of the adamantyl group of which it forms an integral part and each of $Q^1$, $Q^2$, $Q^3$, $Q^4$ and $Q^5$ represents phosphorus.

The 2-phospha-tricyclo[3.3.1.1.{3,7}]decyl group (referred to as 2-phospha-adamantyl group herein) may optionally comprise, beside hydrogen atoms, one or more substituents. Suitable substituents include those substituents as defined herein in respect of the adamantyl group. Highly preferred substituents include lower alkyl, particularly unsubstituted $C_1$-$C_8$ alkyl, especially methyl, trifluoromethyl, —$OR^{19}$ wherein $R^{19}$ is as defined herein particularly unsubstituted $C_1$-$C_8$ alkyl or aryl, and 4-dodecylphenyl. When the 2-phospha-adamantyl group includes more than one substituent, preferably each substituent is identical.

Preferably, the 2-phospha-adamantyl group is substituted on one or more of the 1, 3, 5 or 7 positions with a substituent as defined herein. More preferably, the 2-phospha-adamantyl group is substituted on each of the 1, 3 and 5 positions. Suitably, such an arrangement means the phosphorous atom of the 2-phospha-adamantyl group is bonded to carbon atoms in the adamantyl skeleton having no hydrogen atoms. Most preferably, the 2-phospha-adamantyl group is substituted on each of the 1, 3, 5 and 7 positions. When the 2-phospha-adamantyl group includes more than 1 substituent preferably each substituent is identical. Especially preferred substituents are unsubstituted $C_1$-$C_8$ alkyl and trifluoromethyl, particularly unsubstituted $C_1$-$C_8$ alkyl such as methyl. Preferably, the 2-phospha-adamantyl group includes additional heteroatoms, other than the 2-phosphorous atom, in the 2-phospha-adamantyl skeleton. Suitable additional heteroatoms include oxygen and sulphur atoms, especially oxygen atoms. More preferably, the 2-phospha-adamantyl group includes one or more additional heteroatoms in the 6, 9 and 10 positions. Even more preferably, the 2-phospha-adamantyl group includes an additional heteroatom in each of the 6, 9 and 10 positions. Most preferably, when the 2-phospha-adamantyl group includes two or more additional heteroatoms in the 2-phospha-adamantyl skeleton, each of the additional heteroatoms are identical. An especially preferred 2-phospha-adamantyl group, which may optionally be substituted with one or more substituents as defined herein, includes an oxygen atom in each of the 6, 9 and 10 positions of the 2-phospha-adamantyl skeleton.

Highly preferred 2-phospha-adamantyl groups as defined herein include 2-phospha-1,3,5,7-tetramethyl-6,9,10-trioxadamantyl group, 2-phospha-1,3,5-trimethyl-6,9,10-trioxadamantyl group, 2-phospha-1,3,5,7-tetra(trifluoromethyl)-6,9, 10-trioxadamantyl group, and 2-phospha-1,3,5-tri (trifluoromethyl)-6,9,10-trioxadamantyl group. Most preferably, the 2-phospha-adamantyl is selected from 2-phospha-1,3,5,7-tetramethyl-6,9,10-trioxadamantyl group or 2-phospa-1,3,5-trimethyl-6,9,10-trioxadamantyl group.

Preferably, when more than one 2-phospha-adamantyl group is present in a compound of formula III, each 2-phospha-adamantyl group is identical.

The above definition of the term "2-phospha-tricyclo [3.3.1.1.{3,7}]decyl group" applies equally to the group when it is present in formula I but wherein $X'''$ in formula III, i.e. $X^1$, $X^2$, $X^3$ ... $X^{10}$, is denoted $CR^xR^yR^z$, i.e. $CR^1R^2 R^3$, ... $CR^{16}R^{17}R^{18}$, in formula I.

The term congressyl when used herein means a congressyl group (also known as diamantyl group) which may be bonded to $Q^1$, $Q^2$, $Q^3$, $Q^4$ and $Q^5$ respectively. Preferably, $Q^1$ and $Q^2$, and $Q^3$, $Q^4$ and $Q^5$, when present, are bonded to one of the tertiary carbon atoms of the congressyl groups. Suitably, when the congressyl group is unsubstituted, $Q^1$ and $Q^2$, and $Q^3$, $Q^4$ and $Q^5$ when present, are preferably bonded to the 1-position of one or more congressyl groups.

The congressyl group may optionally comprise, beside hydrogen atoms, one or more substituents. Suitable substituents include those substituents as defined herein in respect of the adamantyl group. Highly preferred substituents include unsubstituted $C_1$-$C_6$ alkyl groups, particularly methyl, and trifluoromethyl. Most preferably, the congressyl group is unsubstituted and comprises hydrogen atoms only.

Preferably, when more than one congressyl group is present in a compound of formula III, each congressyl group is identical.

Preferably, where one or more ring systems of formula IIIa, IIIb, IIIc, IIId or IIIe are present in a compound of formula III, $R^{50}$ to $R^{53}$ each independently represent lower alkyl, aryl or Het, which groups are optionally substituted and/or terminated as defined herein. Such an arrangement means $Q^2$, $Q^1$, $Q^3$, $Q^4$ and $Q^5$ of the ring system of formula IIIa to IIIe, respectively, is not bonded to a carbon atom bearing a hydrogen atom. Even more preferably, $R^{50}$ to $R^{53}$ each independently represent optionally substituted $C_1$-$C_6$ alkyl, preferably non-substituted $C_1$-$C_6$ alkyl, phenyl optionally substituted with non-substituted $C_1$-$C_6$ alkyl or $OR^{19}$ where $R^{19}$ represents non-substituted $C_1$-$C_6$ alkyl, or trifluoromethyl. Even more preferably $R^{50}$ to $R^{53}$ each represent the same group as defined herein, particularly non-substituted $C_1$-$C_6$ alkyl, especially methyl.

Preferably, where one or more ring system of formula IIIa to IIIe are present in a compound of formula III, $R^{49}$ and $R^{54}$ each independently represent optionally substituted $C_1$-$C_6$ alkyl, preferably non-substituted $C_1$-$C_6$ alkyl, phenyl optionally substituted with non-substituted $C_1$-$C_6$ alkyl or $OR^{19}$ where $R^{19}$ represents non-substituted $C_1$-$C_6$ alkyl, trifluoromethyl or hydrogen. More preferably, $R^{49}$ and $R^{54}$ represent the same group as defined herein, especially hydrogen.

Preferably, where one or more ring systems of formula IIIa to IIIe are present in a compound of formula III, $Y^1$ to $Y^5$ are identical. Most preferably, each of $Y^1$ to $Y^5$ represents oxygen. Preferably, where more than one ring system of formula IIIa to IIIe is present in a compound of formula III, each such ring system is identical.

Preferred embodiments of the present invention include those wherein:
$X^1$ represents $CR^1(R^2)(R^3)$, $X^2$ represents $CR^4(R^5)(R^6)$, $X^3$ represents $CR^7(R^8)(R^9)$ and $X^4$ represents $CR^{10}(R^{11})(R^{12})$;

$X^1$ represents $CR^1(R^2)(R^3)$, $X^2$ represents adamantyl, $X^3$ represents $CR^7(R^8)(R^9)$ and $X^4$ represents adamantyl;
$X^1$ represents $CR^1(R^2)(R^3)$, $X^2$ represents congressyl, $X^3$ represents $CR^7(R^8)(R^9)$ and $X^4$ represents congressyl;
$X^1$ represents $CR^1(R^2)(R^3)$, $X^2$ represents $CR^4(R^5)(R^6)$, and $X^3$ and $X^4$ together with $Q^1$ to which they are attached form a ring system of formula IIIb or a 2-phospha-adamantyl group;
$X^1$ represents $CR^1(R^2)(R^3)$, $X^2$ represents adamantyl, $X^3$ and $X^4$ together with $Q^1$ to which they are attached form a ring system of formula IIIb or a 2-phospha-adamantyl group;
$X^1$ represents $CR^1(R^2)(R^3)$, $X^2$ represents congressyl, $X^3$ and $X^4$ together with $Q^1$ to which they are attached form a ring system of formula IIIb or a 2-phospha-adamantyl group;
$X^1$ to $X^4$ each independently represent adamantyl;
$X^1$ to $X^4$ each independently represent congressyl;
$X^1$ and $X^2$ each independently represent adamantyl and $X^3$ and $X^4$ each independently represent congressyl;
$X^1$ and $X^3$ independently represent adamantyl and $X^2$ and $X^4$ independently represent congressyl;
$X^1$ and $X^2$ independently represent adamantyl, $X^3$ represents $CR^7(R^8)(R^9)$ and $X^4$ represents $CR^{10}(R^{11})(R^{12})$;
$X^1$ and $X^2$ independently represent congressyl, $X^3$ represents $CR^7(R^8)(R^9)$ and $X^4$ represents $CR^{10}(R^{11})(R^{12})$;
$X^1$ and $X^2$ independently represent adamantyl, and $X^3$ and $X^4$ together with $Q^1$ to which they are attached form a ring system of formula IIIb or a 2-phospha-adamantyl group;
$X^1$ and $X^2$ independently represent congressyl, and $X^3$ and $X^4$ together with $Q^1$ to which they are attached form a ring system of formula IIIb or a 2-phospha-adamantyl group;
$X^1$ and $X^2$ together with $Q^2$ to which they are attached form a ring system of formula IIIa, and $X^3$ and $X^4$ together with $Q^1$ to which they are attached form a ring system of formula IIIb;
$X^1$ and $X^2$ together with $Q^2$ to which they are attached form a 2-phospha-adamantyl group, and $X^3$ and $X^4$ together with $Q^1$ to which they are attached form a 2-phospha-adamantyl group;

Highly preferred embodiments of the present invention include those wherein:
$X^1$ represents $CR^1(R^2)(R^3)$, $X^2$ represents $CR^4(R^5)(R^6)$, $X^3$ represents $CR^7(R^8)(R^9)$ and $X^4$ represents $CR^{10}(R^{11})(R^{12})$;
$X^1$ represents $CR^1(R^2)(R^3)$, $X^2$ represents adamantyl, $X^3$ represents $CR^7(R^8)(R^9)$ and $X^4$ represents adamantyl;
$X^1$ represents $CR^1(R^2)(R^3)$, $X^2$ represents congressyl, $X^3$ represents $CR^7(R^8)(R^9)$ and $X^4$ represents congressyl;
$X^1$ to $X^4$ each independently represent adamantyl;
$X^1$ to $X^4$ each independently represent congressyl;
$X^1$ and $X^2$ together with $Q^2$ to which they are attached form a ring system of formula IIIa, and $X^3$ and $X^4$ together with $Q^1$ to which they are attached form a ring system of formula IIIb;
$X^1$ and $X^2$ together with $Q^2$ to which they are attached form a 2-phospha-adamantyl group, and $X^3$ and $X^4$ together with $Q^1$ to which they are attached form a 2-phospha-adamantyl group;

Preferably in a compound of formula III, $X^1$ is identical to $X^3$ and $X^2$ is identical to $X^4$. More preferably, $X^1$ is identical to $X^3$ and $X^5$, $X^7$ and $X^9$ when present, and $X^2$ is identical to $X^4$ and $X^6$, $X^8$ and $X^{10}$ when present. Even more preferably, $X^1$ to $X^4$ are identical. Most preferably, $X^1$ to $X^4$ are identical to each of $X^6$ to $X^{10}$ when present.

Preferably, in the compound of formula III, $X^1$ and $X^2$ represent identical substituents, $X^3$ and $X^4$ represent identical substituents, $X^5$ and $X^6$ (when present) represent identical substituents, $X^7$ and $X^8$ (when present) represent identical substituents, and $X^9$ and $X^{10}$ (when present) represent identical substituents.

Preferably, in a compound of formula III, $K^1$ represents $-A_3-Q^3(X^5)X^6$, hydrogen, lower alkyl, $—CF_3$, phenyl or lower alkyl phenyl. More preferably, $K^1$ represents $-A_3-Q^3(X^5)X^6$, hydrogen, unsubstituted $C_1-C_6$ alkyl, unsubstituted phenyl, trifluoromethyl or $C_1-C_6$ alkyl phenyl.

In a particular preferred embodiment $K^1$ in a compound of formula III represents hydrogen.

In an alternative embodiment where $K^1$ does not represent hydrogen, $K^1$ represents $-A_3-Q^3(X^5)X^6$. Preferably, $X^5$ is identical to $X^3$ or $X^1$, and $X^6$ is identical to $X^2$ or $X^4$. More preferably, $X^5$ is identical to both $X^3$ and $X^1$, and $X^6$ is identical to both $X^2$ and $X^4$. Even more preferably, $-A_3-Q^3(X^5)X^6$ is identical to either $-A_1-Q^2(X^1)X^2$ or $-A_2-Q^1(X^3)X^4$. Most preferably, $-A_3-Q^3(X^5)X^6$ is identical to both $-A_1-Q^2(X^1)X^2$ and $-A_2-Q^1(X^3)X^4$.

Most preferably, $K^1$ represents hydrogen in a compound of formula III.

Preferably, in the compound of formula III, $D^1$ represents $-A_4-Q^4(X^7)X^8$, hydrogen, lower alkyl, $CF_3$, phenyl or lower alkylphenyl, and $E^1$ represents $-A_5-Q^5(X^9)X^{10}$, hydrogen, lower alkyl, $CF_3$, phenyl or lower alkylphenyl, or $D^1$ and $E^1$ together with the carbons of the cyclopentadienyl ring to which they are attached form an optionally substituted phenyl ring. More preferably, $D^1$ represents $-A_4-Q^4(X^7)X^8$, hydrogen, phenyl, $C_1-C_6$ alkylphenyl, unsubstituted $C_1-C_6$ alkyl, such as methyl, ethyl, propyl, butyl, pentyl and hexyl, or $CF_3$; $E^1$ represents $-A_5-Q^5(X^9)X^{10}$, hydrogen, phenyl, $C_1-C_6$ alkylphenyl, unsubstituted $C_1-C_6$ alkyl such as methyl, ethyl, propyl, butyl, pentyl and hexyl, or $—CF_3$; or both $D^1$ and $E^1$ together with the carbon atoms of the cyclopentadienyl ring to which they are attached form a phenyl ring which is optionally substituted with one or more groups selected from phenyl, $C_1-C_6$ alkylphenyl, unsubstituted $C_1-C_6$ alkyl or $—CF_3$.

Suitably, when $D^1$ and $E^1$ together with the carbon atoms of the cyclopentadienyl ring to which they are attached form an optionally substituted phenyl ring, the metal M or cation thereof is attached to an indenyl ring system.

In a particular preferred embodiment, $D^1$ in a compound of formula III, represents hydrogen.

In an alternative embodiment where $D^1$ does not represent hydrogen, $D^1$ represents $-A-Q^4(X^7)X^8$. Preferably $X^8$ is identical to $X^4$ or $X^2$, and $X^7$ is identical to $X^1$ or $X^3$. More preferably, $X^8$ is identical to both $X^4$ and $X^2$, and $X^7$ is identical to $X^1$ and $X^3$. Even more preferably, $-A_4-Q^4(X^7)X^8$ is identical to either $-A_1-Q^2(X^1)X^2$ or $-A_2-Q^1(X^3)X^4$. Most preferably, $-A_4-Q^4(X^7)X^8$ is identical to both $-A_2-Q^1(X^3)X^4$, and $-A_3-Q^3(X^5)X^6$ if present.

In a particular preferred embodiment, $E^1$ in a compound of formula III represents hydrogen.

In an alternative embodiment where $E^1$ does not represent hydrogen, $E^1$ represents $-A_5-Q^5(X^9)X^{10}$. Preferably $X^{10}$ is identical to $X^4$ or $X^2$, and $X^9$ is identical to $X^1$ or $X^3$. More preferably, $X^{10}$ is identical to both $X^4$ and $X^2$, and $X^9$ is identical to $X^1$ and $X^3$. Even more preferably, $-A_5-Q^5(X^9)X^{10}$ is identical to either $-A_1-Q^2(X^1)X^2$ or $-A_2-Q^1(X^3)X^4$. Most preferably, $-A_5-Q^5(X^9)X^{10}$ is identical to both $-A_1-Q^2(X^1)X^2$ and $-A_2-Q^1(X^3)X^4$, and $-A_3-Q^3(X^5)X^6$ and $-A-Q^4(X^8$ if present.

Preferably, in the compound of formula III, when $D^1$ and $E^1$ together with the carbon atoms of the cyclopentadienyl ring to which they are attached do not form an optionally substituted phenyl ring, each of $K^1$, $D^1$ and $E^1$ represent an identical substituent.

In an alternative preferred embodiment, $D^1$ and $E^1$ together with the carbons of the cyclopentadienyl ring to which they are attached form an unsubstituted phenyl ring.

Highly preferred embodiments of compounds of formula III include those wherein:

$K^1$, $D^1$ and $E^1$ are identical substituents as defined herein, particularly where $K^1$, $D^1$ and $E^1$ represent hydrogen;

$K^1$ represents hydrogen, and $D^1$ and $E^1$ together with the carbons of the cyclopentadienyl ring to which they are attached form an unsubstituted phenyl ring;

$K^1$ represents $-A_3-Q^3(X^5)X^6$ as defined herein and both $D^1$ and $E^1$ represent H;

$K^1$ represents $-A_3-Q^3(X^5)X^6$ as defined herein and $D^1$ and $E^1$ together with the carbon atoms of the cyclopentadienyl ring to which they are attached form an unsubstituted phenyl ring;

$K^1$ represents $-A_3-Q^3(X^5)X^6$, $D^1$ represents $-A_4-Q^4(X^7)X^8$ and $E^1$ represents $-A_5-Q^5(X^9)X^{10}$.

Especially preferred compounds of formula III include those where both $D^1$ and $E^1$ represent hydrogen or $D^1$ and $E^1$ together with the carbon atoms of the cyclopentadienyl ring to which they are attached form an unsubstituted phenyl ring, particularly those compounds where both $D^1$ and $E^1$ represent hydrogen.

Preferably, in the compound of formula III, $A_1$ and $A_2$, and $A_3$, $A_4$ and $A_5$ (when present), each independently represent $C_1$ to $C_6$ alkylene which is optionally substituted as defined herein, for example with lower alkyl groups. Suitably, $A_1$ and $A_2$, and $A_3$, $A_4$ and $A_5$ (when present) may include a chiral carbon atom. Preferably, the lower alkylene groups which $A_1$ to $A_5$ may represent are non-substituted. A particular preferred lower alkylene, which $A_1$ to $A_5$ may independently represent, is —CH$_2$— or —C$_2$H$_4$—. Most preferably, each of $A_1$ and $A_2$, and $A_3$, $A_4$ and $A_5$ (when present), represent the same lower alkylene as defined herein, particularly —CH$_2$—.

In the compound of formula III, preferably each $Q^1$ and $Q^2$, and $Q^3$, $Q^4$ and $Q^5$ (when present) are the same. Most preferably, each $Q^1$ and $Q^2$, and $Q^3$, $Q^4$ and $Q^5$ (when present), represents phosphorus.

It will be appreciated by those skilled in the art that the compounds of formula III may function as ligands that coordinate with the Group VIB or Group VIIIB metal or compound thereof in the formation of the catalyst system of the invention. Typically, the Group VIB or Group VIIIB metal or compound thereof coordinates to the one or more phosphorus, arsenic and/or antimony atoms of the compound of formula III. It will be appreciated that the compounds of formula III may be referred to broadly as "metallocenes".

Suitably, when n=1 and $L_1$ represents an optionally substituted cyclopentadienyl or indenyl group, the compounds of formula III may contain either two cyclopentadienyl rings, two indenyl rings or one indenyl and one cyclopentadienyl ring (each of which ring systems may optionally be substituted as described herein). Such compounds may be referred to as "sandwich compounds" as the metal M or metal cation thereof is sandwiched by the two ring systems. The respective cyclopentadienyl and/or indenyl ring systems may be substantially coplanar with respect to each other or they may be tilted with respect to each other (commonly referred to as bent metallocenes).

Alternatively, when n=1 and $L_1$ represents aryl, the compounds of the invention may contain either one cyclopentadienyl or one indenyl ring (each of which ring systems may optionally be substituted as described herein) and one aryl ring which is optionally substituted as defined herein. Suitably, when n=1 and $L_1$ represents aryl then the metal M of the compounds of formula III as defined herein is typically in the form of the metal cation.

In a particularly preferred embodiment of the present invention, in a compound of formula III, n=1, $L_1$ is as defined herein and m=0.

Preferably, when n=1 in the compound of formula III, $L_1$ represents cyclopentadienyl, indenyl or aryl ring each of which rings are optionally substituted by one or more substituents selected from hydrogen, lower alkyl, halo, cyano, nitro, —OR$^{19}$, —OC(O)R$^{20}$, —C(O)R$^{21}$, —C(O)OR$^{22}$, —N(R$^{23}$)R$^{24}$, —C(O)N(R$^{25}$)R$^{26}$, —C(S) (R$^{27}$)R$^{28}$, —SR$^{29}$, —C(O)SR$^{30}$, —CF$_3$ or ferrocenyl (by which we mean the cyclopentadienyl, indenyl or aryl ring which $L_1$ may represent is bonded directly to the cyclopentadienyl ring of the ferrocenyl group), wherein R$^{19}$ to R$^{30}$ is as defined herein. More preferably, if the cyclopentadienyl, indenyl or aryl ring which $L_1$ may represent is substituted it is preferably substituted with one or more substituents selected from unsubstituted C$_1$-C$_6$ alkyl, halo, cyano, —OR$^{19}$, —OC(O)R$^{20}$, C(O)R$^{21}$, —C(O)OR$^{22}$, —N(R$^{23}$)R$^{24}$ where R$^{19}$, R$^{20}$, R$^{21}$, R$^{22}$, R$^{23}$ and R$^{24}$ each independently represent hydrogen or C$_1$-C$_6$ alkyl. Even more preferably, if the cyclopentadienyl, indenyl or aryl ring which $L_1$ may represent is substituted, it is preferably substituted with one or more substituents selected from unsubstituted C$_1$-C$_6$ alkyl.

Preferably, when n=1, $L_1$, represents cyclopentadienyl, indenyl, phenyl or napthyl optionally substituted as defined herein. Preferably, the cyclopentadienyl, indenyl, phenyl or napthyl groups are unsubstituted. More preferably, $L_1$ represents cyclopentadienyl, indenyl or phenyl, each of which rings are unsubstituted. Most preferably, $L_1$ represents unsubstituted cyclopentadienyl.

Alternatively, when n=0, the compounds of the invention contain only one cyclopentadienyl or indenyl ring (each of which ring systems may optionally be substituted as described herein). Such compounds may be referred to as "half sandwich compounds". Preferably, when n=0 then m represents 1 to 5 so that the metal M of the compounds of formula III has an 18 electron count. In other words, when metal M of the compounds of formula III is iron, the total number of electrons contributed by the ligands $L_2$ is typically five.

In a particularly preferred alternative embodiment of the present invention, in a compound of formula III, n=0, $L_2$ is as defined herein and m=3 or 4, particularly 3.

Preferably, when n is equal to zero and m is not equal to zero in a compound of formula III, $L_2$ represents one or more ligands each of which are independently selected from lower alkyl, halo, —CO, —P(R$^{43}$)(R$^{44}$)R$^{45}$ or —N(R$^{46}$)(R$^{47}$)R$^{48}$. More preferably, $L_2$ represents one or more ligands each of which are independently selected from unsubstituted C$_1$ to C$_4$ alkyl, halo, particularly chloro, —CO, —P(R$^{43}$)(R$^{44}$)R$^{45}$ or —N(R$^{46}$)(R$^{47}$)R$^{48}$, wherein R$^{43}$ to R$^{48}$ are independently selected from hydrogen, unsubstituted C$_1$ to C$_6$ alkyl or aryl, such as phenyl.

Suitably, the metal M or metal cation thereof in the compounds of formula III is typically bonded to the cyclopentadienyl ring(s), the cyclopentadienyl moiety of the indenyl ring(s) if present, the aryl ring if present, and/or the ligands $L_2$ if present. Typically, the cyclopentadienyl ring or the cyclopentadienyl moiety of the indenyl ring exhibits a pentahapto bonding mode with the metal; however other bonding modes between the cyclopentadienyl ring or cyclopentadienyl moiety of the indenyl ring and the metal, such as trihapto coordination, are also embraced by the scope of the present invention.

Most preferably, in a compound of formula III, n=1, m=0 and $L_1$ is defined herein, particularly unsubstituted cyclopentadienyl.

Preferably M represents a Group VIB or VIIIB metal. In other words the total electron count for the metal M is 18.

Preferably, in the compound of formula III, M represents Cr, Mo, Fe, Co or Ru, or a metal cation thereof. Even more preferably, M represents Cr, Fe, Co or Ru or a metal cation thereof. Most preferably, M is selected from a Group VIIIB metal or metal cation thereof. An especially preferred Group VIIIB metal is Fe. Although the metal M as defined herein may be in a cationic form, preferably it carries essentially no residual charge due to coordination with $L_1$ and/or $L_2$ as defined herein.

Especially preferred compounds of formula III include those wherein:

(1) $X^1$ represents $CR^1(R^2)(R^3)$, $X^2$ represents $CR^4(R^5)(R^6)$ $X^3$ represents $CR^7(R^8)(R^9)$, $X^4$ represents $CR^{10}(R^{11})(R^{12})$ wherein each of $R^1$ to $R^{12}$ independently represents unsubstituted $C_1$-$C_6$ alkyl or trifluoromethyl, particularly where each of $R^1$ to $R^{12}$ is identical, especially where each of $R^1$ to $R^{12}$ represents unsubstituted $C_1$-$C_6$ alkyl, particularly methyl;
$A_1$ and $A_2$ are the same and represent —$CH_2$—;
$K^1$, $D^1$ and $E^1$ are the same and represent hydrogen or unsubstituted $C_1$-$C_6$ alkyl, particularly hydrogen;
$Q^1$ and $Q^2$ both represent phosphorus;
M represents Fe;
n=1 and $L_1$ represents cyclopentadienyl, particularly unsubstituted cyclopentadienyl, and m=0.

(2) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$; $K^1$ represents —$CH_2$-$Q^3(X^5)X^6$ wherein $X^5$ represents $CR^{13}(R^{14})(R^{15})$ and $X^6$ represents $CR^{16}(R^{17})(R^{18})$;
each of $R^1$ to $R^{18}$ independently represent unsubstituted $C_1$-$C_6$ alkyl or trifluoromethyl, particularly where each of $R^1$ to $R^{18}$ is identical, especially where each of $R^1$ to $R^{18}$ represents unsubstituted $C_1$-$C_6$ alkyl, particularly methyl;
$A_1$ and $A_2$ are the same and represent —$CH_2$—;
$Q^1$, $Q^2$ and $Q^3$ each represent phosphorus;
$D^1$ and $E^1$ are the same and represent hydrogen or unsubstituted $C_1$-$C_6$ alkyl, particularly hydrogen;
M represents Fe;
n=1 and $L_1$ represents cyclopentadienyl, particularly unsubstituted cyclopentadienyl, and m=0.

(3) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$;
$K^1$ represents —$CH_2$-$Q^3(X^5)X^6$ wherein $X^5$ represents $CR^{13}(R^{14})(R^{15})$ and $X^6$ represents $CR^{16}(R^{17})(R^{18})$;
each of $R^1$ to $R^{18}$ independently represent unsubstituted $C_1$-$C_6$ alkyl or trifluoromethyl, particularly where each of $R^1$ to $R^{18}$ is identical, especially where each of $R^1$ to $R^{18}$ represents unsubstituted $C_1$-$C_6$ alkyl, particularly methyl;
$A_1$ and $A_2$ are the same and represent —$CH_2$—;
$Q^1$, $Q^2$ and $Q^3$ each represent phosphorus;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(4) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$ wherein each of $R^1$ to $R^{12}$ independently represent unsubstituted $C_1$-$C_6$ alkyl or trifluoromethyl, particularly where each of $R^1$ to $R^{12}$ is identical, especially where each of $R^1$ to $R^{12}$ represents unsubstituted $C_1$-$C_6$ alkyl, particularly methyl;
$A_1$ and $A_2$ are the same and represent —$CH_2$—;
$Q^1$ and $Q^2$ both represent phosphorus;
$K^1$ represents hydrogen or $C_1$-$C_6$ alkyl, particularly hydrogen;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(5) $X^1$ represents $CR^1(R^2)(R^3)$, $X^2$ represents $CR^4(R^5)(R^5)$, $X^3$ represents $CR^7(R^8)(R^9)$, $X^4$ represents $CR^{10}(R^{11})(R^{12})$;
$E^1$ represents —$CH_2$-$Q^5(X^9)X^{10}$ wherein $X^9$ represents $CR^{37}(R^{38})(R^{39})$ and $X^{10}$ represents $CR^{40}(R^{41})(R^{42})$;
each of $R^1$ to $R^{12}$ and $R^{37}$ to $R^{42}$ independently represent unsubstituted $C_1$-$C_6$ alkyl or trifluoromethyl, particularly where each of $R^1$ to $R^{12}$ and $R^{37}$ to $R^{42}$ is identical, especially where each of $R^1$ to $R^{12}$ and $R^{37}$ to $R^{42}$ represents unsubstituted $C_1$-$C_6$ alkyl, particularly methyl;
$A_1$ and $A_2$ are the same and represent —$CH_2$—;
$Q^1$, $Q^2$ and $Q^5$ each represent phosphorus;
$D^1$ and $K^1$ are the same and represent hydrogen or unsubstituted $C_1$-$C_6$ alkyl, particularly hydrogen;
M represents Fe;
n=1 and $L_1$ represents cyclopentadienyl, particularly unsubstituted cyclopentadienyl, and m=0.

(6) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$;
$K^1$ represents —$CH_2$-$Q^3(X^5)X^6$ wherein $X^5$ represents $CR^{13}(R^{14})(R^{15})$ and $X^6$ represents $CR^{16}(R^{17})(R^{18})$;
$D^1$ represents —$CH_2$-$Q^4(X^7)X^8$ wherein $X^7$ represents $CR^{31}(R^{32})(R^{33})$ and $X^8$ represents $CR^{34}(R^{35})(R^{36})$;
$E^1$ represents —$CH_2$-$Q^5(X^9)X^{10}$ wherein $X^9$ represents $CR^{37}(R^{38})(R^{39})$ and $X^{10}$ represents $CR^{40}(R^{41})(R^{42})$
each of $R^1$ to $R^{18}$ and $R^{31}$ to $R^{42}$ independently represent unsubstituted $C_1$-$C_6$ alkyl or trifluoromethyl, particularly where each of $R^1$ to $R^{18}$ and $R^{31}$ to $R^{42}$ is identical, especially where each of $R^1$ to $R^{18}$ and $R^{31}$ to $R^{42}$ represents unsubstituted $C_1$-$C_6$ alkyl, particularly methyl;
$A_1$ and $A_2$ are the same and represent —$CH_2$—;
$Q^1$, $Q^2$, $Q^3$, $Q^4$ and $Q^5$ each represent phosphorus
M represents Fe;
n=1 and $L_1$ represents cyclopentadienyl, particularly unsubstituted cyclopentadienyl, and m=0.

(7) $X^1$, $X^2$, $X^3$ and $X^4$ independently represent adamantyl, especially where $X^1$ to $X^4$ represent the same adamantyl group;
$A_1$ and $A_2$ are the same and represent —$CH_2$—;
$K^1$, $D^1$ and $E^1$ are the same and represent hydrogen or unsubstituted $C_1$-$C_6$ alkyl, particularly hydrogen;
$Q^1$ and $Q^2$ both represent phosphorus;
M represents Fe;
n=1 and $L_1$ represents cyclopentadienyl, particularly unsubstituted cyclopentadienyl, and m=0.

(8) $X^1$, $X^2$, $X^3$ and $X^4$ independently represent adamantyl, especially where $X^1$ to $X^4$ represent the same adamantyl group;
$K^1$ represents —$CH_2$-$Q^3(X^5)X^6$ wherein $X^5$ and $X^6$ independently represent adamantyl, especially where $X^1$ to $X^6$ represent the same adamantyl group;
$A_1$ and $A_2$ are the same and represent —$CH_2$—;
$Q^1$, $Q^2$ and $Q^3$ each represent phosphorus;
$D^1$ and $E^1$ are the same and represent hydrogen or unsubstituted $C_1$-$C_6$ alkyl, particularly hydrogen;
M represents Fe;
n=1 and $L_1$ represents cyclopentadienyl, particularly unsubstituted cyclopentadienyl, and m=0.

(9) $X^1$, $X^2$, $X^3$ and $X^4$ independently represent adamantyl, especially where $X^1$ to $X^4$ represent the same adamantyl group;
$K^1$ represents —$CH_2$-$Q^3(X^5)X^6$ wherein $X^5$ and $X^6$ independently represent adamantyl, especially where $X^1$ to $X^6$ represent the same adamantyl group;
$A_1$ and $A_2$ are the same and represent —$CH_2$—;
$Q^1$, $Q^2$ and $Q^3$ each represent phosphorus;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(10) $X^1$, $X^2$, $X^3$ and $X^4$ independently represent adamantyl, especially where $X^1$ to $X^4$ represent the same adamantyl group;
$A_1$ and $A_2$ are the same and represent —$CH_2$—;
$Q^1$ and $Q^2$ both represent phosphorus;
$K^1$ represents hydrogen or unsubstituted $C_1$-$C_6$ alkyl, particularly hydrogen;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(11) $X^1$, $X^2$, $X^3$ and $X^4$ independently represent adamantyl;
$K^1$ represents —$CH_2$-$Q^3(X^5)X^6$ wherein $X^5$ and $X^6$ independently represent adamantyl;
$D^1$ represents —$CH_2$-$Q^4(X^7)X^8$ wherein $X^7$ and $X^8$ independently represents adamantyl;
$E^1$ represents —$CH_2$-$Q^5(X^9)X^{10}$ wherein $X^9$ and $X^{10}$ independently represents adamantyl especially where $X^1$ to $X^{10}$ represent the same adamantyl group;
$A_1$ and $A_2$ are the same and represent —$CH_2$—;
$Q^1$, $Q^2$, $Q^3$, $Q^4$ and $Q^5$ each represent phosphorus;
M represents Fe;
n=1 and $L_1$ represents cyclopentadienyl, particularly unsubstituted cyclopentadienyl, and m=0.

(12) $X^1$ and $X^2$ together with $Q^2$ to which they are attached represents 2-phospha-adamantyl;
$X^3$ and $X^4$ together with $Q^1$ to which they are attached represents 2-phospha-adamantyl;
$A_1$ and $A_2$ are the same and represent —$CH_2$—;
$K^1$, $D^1$ and $E^1$ are the same and represent hydrogen or unsubstituted $C_1$-$C_6$ alkyl, particularly hydrogen;
$Q^1$ and $Q^2$ both represent phosphorus;
M represents Fe;
n=1 and $L_1$ represents cyclopentadienyl, particularly unsubstituted cyclopentadienyl, and m=0.

(13) $X^1$ and $X^2$ together with $Q^2$ to which they are attached represents 2-phospha-adamantyl;
$X^3$ and $X^4$ together with $Q^1$ to which they are attached represents 2-phospha-adamantyl;
$K^1$ represents —$CH_2$-$Q^3(X^5)X^6$ wherein $X^5$ and $X^6$ together with $Q^3$ to which they are attached represents 2-phospha-adamantyl;
$A_1$ and $A_2$ are the same and represent —$CH_2$—;
$Q^1$, $Q^2$ and $Q^3$ each represent phosphorus;
$D^1$ and $E^1$ are the same and represent hydrogen or unsubstituted $C_1$-$C_6$ alkyl, particularly hydrogen;
M represents Fe;
n=1 and $L_1$ represents cyclopentadienyl, particularly unsubstituted cyclopentadienyl, and m=0.

(14) $X^1$ and $X^2$ together with $Q^2$ to which they are attached represents 2-phospha-adamantyl;
$X^3$ and $X^4$ together with $Q^1$ to which they are attached represents 2-phospha-adamantyl;
$K^1$ represents —$CH_2$-$Q^3(X^5)X^6$ wherein $X^5$ and $X^6$ together with $Q^3$ to which they are attached represents 2-phospha-adamantyl;
$A_1$ and $A_2$ are the same and represent —$CH_2$—;
$Q^1$, $Q^2$ and $Q^3$ each represent phosphorus;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(15) $X^1$ and $X^2$ together with $Q^2$ to which they are attached represents 2-phospha-adamantyl;
$X^3$ and $X^4$ together with $Q^1$ to which they are attached represents 2-phospha-adamantyl;
$A_1$ and $A_2$ are the same and represent —$CH_2$—;
$Q^1$ and $Q^2$ both represent phosphorus;
$K^1$ represents hydrogen or unsubstituted $C_1$-$C_6$ alkyl, particularly hydrogen;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(16) $X^1$ and $X^2$ together with $Q^2$ to which they are attached represents 2-phospha-adamantyl;
$X^3$ and $X^4$ together with $Q^1$ to which they are attached represents 2-phospha-adamantyl;
$K^1$ represents —$CH_2$-$Q^3(X^5)X^6$ wherein $X^5$ and $X^6$ together with $Q^3$ to which they are attached represents 2-phospha-adamantyl;
$D^1$ represents —$CH_2$-$Q^4(X^7)X^8$ wherein $X^7$ and $X^8$ together with $Q^4$ to which they are attached represents 2-phospha-adamantyl;
$E^1$ represents —$CH_2$-$Q^5(X^9)X^1$ wherein $X^9$ and $X^{10}$ together with $Q^5$ to which they are attached represents 2-phospha-adamantyl;
$A_1$ and $A_2$ are the same and represent —$CH_2$—;
$Q^1$, $Q^2$, $Q^3$, $Q^4$ and $Q^5$ each represent phosphorus
M represents Fe;
n=1 and $L_1$ represents cyclopentadienyl, particularly unsubstituted cyclopentadienyl, and m=0.

(17) $X^1$ and $X^2$ together with $Q^2$ to which they are attached form a ring system of formula IIIa, $X^3$ and $X^4$ together with $Q^1$ to which they are attached form a ring system of formula IIIb, wherein $Y^1$ and $Y^2$ both represent oxygen, $R^{50}$ to $R^{53}$ are independently selected from unsubstituted $C_1$-$C_6$ alkyl or $CF_3$, and $R^{49}$ and $R^{54}$ represent hydrogen;
$A_1$ and $A_2$ are the same and represent —$CH_2$—;
$K^1$, $D^1$ and $E^1$ are the same and represent hydrogen or unsubstituted $C_1$-$C_6$ alkyl, particularly hydrogen;
$Q^1$ and $Q^2$ both represent phosphorus;
M represents Fe;
n=1 and $L_1$ represents cyclopentadienyl, particularly unsubstituted cyclopentadienyl (referred to as puc) and m=0.

(18) $X^1$ and $X^2$ together with $Q^2$ to which they are attached form a ring system of formula IIIa, $X^3$ and $X^4$ together with $Q^1$ to which they are attached form a ring system of formula IIIb, wherein $Y^1$ and $Y^2$ both represent oxygen, $R^{50}$ to $R^{53}$ are independently selected from unsubstituted $C_1$-$C_6$ alkyl or $CF_3$, and $R^{49}$ and $R^{54}$ represent hydrogen;
$K^1$ represents —$CH_2$-$Q^3(X^5)X^6$ wherein $X^5$ and $X^6$ together with $Q^3$ to which they are attached form a ring system of formula IIIc, wherein $Y^3$ represents oxygen, $R^{50}$ to $R^{53}$ are independently selected from hydrogen, unsubstituted $C_1$-$C_6$ alkyl or $CF_3$ and $R^{49}$ and $R^{54}$ represent hydrogen;

$A_1$ and $A_2$ are the same and represent —$CH_2$—;

$Q^1$, $Q^2$ and $Q^3$ each represent phosphorus;

$D^1$ and $E^1$ are the same and represent hydrogen or $C_1$-$C_6$ alkyl, particularly hydrogen;

M represents Fe;

n=1 and $L_1$ represents cyclopentadienyl, particularly unsubstituted cyclopentadienyl, and m=0.

(19) $X^1$ and $X^2$ together with $Q^2$ to which they are attached form a ring system of formula IIIa, $X^3$ and $X^4$ together with $Q^1$ to which they are attached form a ring system of formula IIIb, wherein $Y^1$ and $Y^2$ both represent oxygen, $R^{50}$ to $R^{53}$ are independently selected from unsubstituted $C_1$-$C_6$ alkyl or $CF_3$, and $R^{49}$ and $R^{54}$ represent hydrogen;

$K^1$ represents —$CH_2$-$Q^3(X^5)X^6$ wherein $X^5$ and $X^6$ together with $Q^3$ to which they are attached form a ring system of formula IIIc, wherein $Y^3$ represents oxygen, $R^{50}$ to $R^{53}$ are independently selected from unsubstituted $C_1$-$C_6$ alkyl or $CF_3$, and $R^{49}$ and $R^{54}$ represent hydrogen;

$A_1$ and $A_2$ are the same and represent —$CH_2$—;

$Q^1$, $Q^2$ and $Q^3$ each represent phosphorus;

$D^1$ and $E^1$ together with the carbon atoms of the cyclopentadienyl ring to which they are attached form an unsubstituted phenyl ring;

M represents Fe;

n=1 and $L_1$ represents cyclopentadienyl, particularly unsubstituted cyclopentadienyl, and m=0.

(20) $X^1$ and $X^2$ together with $Q^2$ to which they are attached form a ring system of formula IIIa, $X^3$ and $X^4$ together with $Q^1$ to which they are attached form a ring system of formula IIIb, wherein $Y^1$ and $Y^2$ both represent oxygen, $R^{50}$ to $R^{53}$ are independently selected from unsubstituted $C_1$-$C_6$ alkyl or $CF_3$, and $R^{49}$ and $R^{54}$ represent hydrogen;

$A_1$ and $A_2$ are the same and represent —$CH_2$—;

$Q^1$ and $Q^2$ both represent phosphorus;

$K^1$ represents hydrogen or unsubstituted $C_1$-$C_6$ alkyl, particularly hydrogen;

$D^1$ and $E^1$ together with the carbon atoms of the cyclopentadienyl ring to which they are attached form an unsubstituted phenyl ring;

M represents Fe;

n=1 and $L_1$ represents cyclopentadienyl, particularly unsubstituted cyclopentadienyl, and m=0.

(21) $X^1$ and $X^2$ together with $Q^2$ to which they are attached form a ring system of formula IIIa, $X^3$ and $X^4$ together with $Q^1$ to which they are attached form a ring system of formula IIIb, wherein $Y^1$ and $Y^2$ both represent oxygen, $R^{50}$ to $R^{53}$ are independently selected from unsubstituted $C_1$-$C_6$ alkyl or $CF_3$, and $R^{49}$ and $R^{54}$ represent hydrogen;

$K^1$ represents —$CH_2$-$Q^3(X^5)X^6$ wherein $X^5$ and $X^6$ together with $Q^3$ to which they are attached form a ring system of formula IIIc, wherein $Y^3$ represents oxygen, $R^{50}$ to $R^{53}$ are independently selected from unsubstituted $C_1$-$C_6$ alkyl or $CF_3$, and $R^{49}$ and $R^{54}$ represent hydrogen;

$D^1$ represents —$CH_2$-$Q^4(X^7)X^8$ wherein $X^7$ and $X^8$ together with $Q^4$ to which they are attached form a ring system of formula IIIc, wherein $Y^3$ represents oxygen, $R^{50}$ to $R^{53}$ are independently selected from unsubstituted $C_1$-$C_6$ alkyl or $CF_3$, and $R^{49}$ and $R^{54}$ represent hydrogen;

$E^1$ represents —$CH_2$-$Q^5(X^9)X^{10}$ wherein $X^9$ and $X^{10}$ together with $Q^5$ to which they are attached form a ring system of formula IIIe, wherein $Y^5$ represents oxygen, and $R^{50}$ to $R^{53}$ are independently selected from unsubstituted $C_1$-$C_6$ alkyl or $CF_3$, and $R^{49}$ and $R^{54}$ represent hydrogen;

$A_1$ and $A_2$ are the same and represent —$CH_2$—;

$Q^1$, $Q^2$, $Q^3$, $Q^4$ and $Q^5$ each represent phosphorus;

M represents Fe;

n=1 and $L_1$ represents cyclopentadienyl; particularly unsubstituted cyclopentadienyl, and m=0.

(22) $X^1$, $X^2$, $X^3$ and $X^4$ independently represent congressyl, especially where $X^1$ to $X^4$ represent the same congressyl group;

$A_1$ and $A_2$ are the same and represent —$CH_2$—;

$K^1$, $D^1$ and $E^1$ are the same and represent hydrogen or unsubstituted $C_1$-$C_6$ alkyl, particularly hydrogen;

$Q^1$ and $Q^2$ both represent phosphorus;

M represents Fe;

n=1 and $L_1$ represents cyclopentadienyl, particularly unsubstituted cyclopentadienyl, and m=0.

(23) $X^1$, $X^2$, $X^3$ and $X^4$ independently represent congressyl, especially where $X^1$ to $X^4$ represent the same congressyl group;

$K^1$ represents —$CH_2$-$Q^3(X^5)X^6$ wherein $X^5$ and $X^6$ independently represent congressyl, especially where $X^1$ to $X^6$ represent the same congressyl group;

$A_1$ and $A_2$ are the same and represent —$CH_2$—;

$Q^1$, $Q^2$ and $Q^3$ each represent phosphorus;

$D^1$ and $E^1$ are the same and represent hydrogen or unsubstituted $C_1$-$C_6$ alkyl, particularly hydrogen;

M represents Fe;

n=1 and $L_1$ represents cyclopentadienyl, particularly unsubstituted cyclopentadienyl, and m=0.

(24) $X^1$, $X^2$, $X^3$ and $X^4$ independently represent congressyl, especially where $X^1$ to $X^4$ represent the same congressyl group;

$K^1$ represents —$CH_2$-$Q^3(X^5)X^6$ wherein $X^5$ and $X^6$ independently represent congressyl, especially where $X^1$ to $X^6$ represent the same congressyl group;

$A_1$ and $A_2$ are the same and represent —$CH_2$—;

$Q^1$, $Q^2$ and $Q^3$ each represent phosphorus;

$D^1$ and $E^1$ together with the carbon atoms of the cyclopentadienyl ring to which they are attached form an unsubstituted phenyl ring;

M represents Fe;

n=1 and $L_1$ represents cyclopentadienyl, particularly unsubstituted cyclopentadienyl, and m=0.

(25) $X^1$, $X^2$, $X^3$ and $X^4$ independently represent congressyl, especially where $X^1$ to $X^4$ represent the same congressyl group;

$A_1$ and $A_2$ are the same and represent —$CH_2$—;

$Q^1$ and $Q^2$ both represent phosphorus;

$K^1$ represents hydrogen or unsubstituted $C_1$-$C_6$ alkyl, particularly hydrogen;

$D^1$ and $E^1$ together with the carbon atoms of the cyclopentadienyl ring to which they are attached form an unsubstituted phenyl ring;

M represents Fe;

n=1 and $L_1$ represents cyclopentadienyl, particularly unsubstituted cyclopentadienyl, and m=0.

(26) $X^1$, $X^2$, $X^3$ and $X^4$ independently represent congressyl;

$K^1$ represents —$CH_2$-$Q^3(X^5)X^6$ wherein $X^5$ and $X^6$ independently represent congressyl;

$D^1$ represents —$CH_2$-$Q^4(X^7)X^8$ wherein $X^7$ and $X^8$ independently represents congressyl;

$E^1$ represents —$CH_2$-$Q^5(X^9)X^{10}$ wherein $X^9$ and $X^{10}$ independently represents congressyl, especially where $X^1$ to $X^{10}$ represent the same congressyl group;

$A_1$ and $A_2$ are the same and represent —$CH_2$—;
$Q^1$, $Q^2$, $Q^3$, $Q^4$ and $Q^5$ each represent phosphorus;
M represents Fe;
n=1 and $L_1$ represents cyclopentadienyl, particularly unsubstituted cyclopentadienyl, and m=0.

(27) $X^1$ and $X^3$ independently represent adamantyl, especially where $X^1$ and $X^3$ represent the same adamantyl group;
$X^2$ represents $CR^4(R^5)(R^6)$ and $X^4$ represents $CR^{10}(R^{11})(R^{12})$ wherein each of $R^4$, $R^5$, $R^6$, $R^{10}$, $R^{11}$ and $R^{12}$ independently represent $C_1$-$C_6$ alkyl or trifluoromethyl, particularly where each of $R^4$ to $R^6$ and $R^{10}$ to $R^{12}$ is identical, especially where each of $R^4$ to $R^6$ and $R^{10}$ to $R^{12}$ represents unsubstituted $C_1$-$C_6$ alkyl, particularly methyl;
$A_1$ and $A_2$ are the same and represent —$CH_2$—;
$K^1$, $D^1$ and $E^1$ are the same and represent hydrogen or unsubstituted $C_1$-$C_6$ alkyl, particularly hydrogen;
$Q^1$ and $Q^2$ both represent phosphorus;
M represents Fe;
n=1 and $L_1$ represents cyclopentadienyl, particularly unsubstituted cyclopentadienyl, and m=0.

(28) $X^1$ and $X^3$ independently represent adamantyl, especially where $X^1$ and $X^3$ represent the same adamantyl group;
$K^1$ represents —$CH_2$-$Q^3(X^5)X^6$ wherein $X^5$ represents adamantyl, especially where $X^1$, $X^3$ and $X^5$ represent the same adamantyl group;
$X^2$ represents $CR^4(R^5)(R^6)$, $X^4$ represents $CR^{10}(R^{11})(R^{12})$, $X^6$ represents $CR^{16}(R^{17})(R^{18})$, wherein each of $R^4$ to $R^6$, $R^{10}$ to $R^{12}$ and $R^{16}$ to $R^{18}$ independently represent unsubstituted $C_1$-$C_6$ alkyl or trifluoromethyl, particularly where each of $R^4$ to $R^6$, $R^{10}$ to $R^{12}$, and $R^{16}$ to $R^{18}$ is identical, especially where each of $R^4$ to $R^6$, $R^{10}$ to $R^{12}$ and $R^{16}$ to $R^{18}$ represents unsubstituted $C_1$-$C_6$ alkyl, particularly methyl;
$A_1$ and $A_2$ are the same and represent —$CH_2$—;
$Q^1$, $Q^2$ and $Q^3$ each represent phosphorus;
$D^1$ and $E^1$ are the same and represent hydrogen or unsubstituted $C_1$-$C_6$ alkyl, particularly hydrogen;
M represents Fe;
n=1 and $L_1$ represents cyclopentadienyl, particularly unsubstituted cyclopentadienyl, and m=0.

(29) $X^1$ and $X^3$ independently represent adamantyl, especially where $X^1$ and $X^3$ represent the same adamantyl group;
$K^1$ represents —$CH_2$-$Q^3(X^5)X^6$ wherein $X^5$ represents adamantyl, especially where $X^1$, $X^3$ and $X^5$ represent the same adamantyl group;
$X^2$ represents $CR^4(R^5)(R^6)$, $X^4$ represents $CR^{10}(R^{11})(R^{12})$, $X^6$ represents $CR^{16}(R^{17})(R^{18})$, wherein each of $R^4$ to $R^6$, $R^{10}$ to $R^{12}$ and $R^{16}$ to $R^{18}$ independently represent unsubstituted $C_1$-$C_6$ alkyl or trifluoromethyl, particularly where each of $R^4$ to $R^6$, $R^{10}$ to $R^{12}$, and $R^{16}$ to $R^{18}$ is identical, especially where each of $R^4$ to $R^6$, $R^{10}$ to $R^{12}$ and $R^{16}$ to $R^{18}$ represents unsubstituted $C_1$-$C_6$ alkyl, particularly methyl;
$A_1$ and $A_2$ are the same and represent —$CH_2$—;
$Q^1$, $Q^2$ and $Q^3$ each represent phosphorus;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(30) $X^1$ and $X^3$ independently represent adamantyl, especially where $X^1$ and $X^3$ represent the same adamantyl group;
$X^2$ represents $CR^4(R^5)(R^6)$ and $X^4$ represents $CR^{10}(R^{11})(R^{12})$ wherein each of $R^4$, $R^5$, $R^6$, $R^{10}$, $R^{11}$ and $R^{12}$ independently represent $C_1$-$C_6$ alkyl or trifluoromethyl, particularly where each of $R^4$ to $R^6$ and $R^{10}$ to $R^{12}$ is identical, especially where each of $R^4$ to $R^6$ and $R^{10}$ to $R^{12}$ represents unsubstituted $C_1$-$C_6$ alkyl, particularly methyl;
$A_1$ and $A_2$ are the same and represent —$CH_2$—;
$Q^1$ and $Q^2$ both represent phosphorus;
$K^1$ represents hydrogen or unsubstituted $C_1$-$C_6$ alkyl, particularly hydrogen;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

Specific but non-limiting examples of bidentate ligands within this embodiment include the following: 1,2-bis-(dimethylaminomethyl)ferrocene, 1,2-bis-(ditertbutylphosphinomethyl)ferrocene, 1-hydroxymethyl-2-dimethylaminomethylferrocene, 1,2-bis-(ditertbutylphosphinomethyl)ferrocene, 1-hydroxymethyl-2,3-bis-(dimethylaminomethyl)ferrocene, 1,2,3-tris-(ditertbutylphosphinomethyl)ferrocene, 1,2-bis-(dicyclohexylphosphinomethyl)ferrocene, 1,2-bis-(di-iso-butylphosphinomethyl)ferrocene, 1,2-bis-(dicyclopentylphosphinomethyl)ferrocene, 1,2-bis-(diethylphosphinomethyl)ferrocene, 1,2-bis(di-isopropylphosphinomethyl)ferrocene, 1,2-bis-(dimethylphosphinomethyl)ferrocene, 1,2-bis-(di-(1,3,5,7-tetramethyl-6,9,10-trioxa-2-phospha-adamantylmethyl))ferrocene, 1,2-bis-(dimethylaminomethyl)ferrocene-bismethyl iodide, 1,2-bis(dihydroxymethylphosphinomethyl)ferrocene, 1,2-bis(diphosphinomethyl)ferrocene, 1,2-bis-α,α-(P-(2,2,6,6-tetramethylphosphinan-4-one))dimethylferrocene, and 1,2-bis-(di-1,3,5,7-tetramethyl-6,9,10-trioxa-2-phospha-adamantylmethyl))benzene. Nevertheless, the skilled person in the art would appreciate that other bidentate ligands can be envisaged without departing from the scope of the invention.

According to a further aspect, the present invention provides a process for the carbonylation of an ethylenically unsaturated compound comprising contacting an ethylenically unsaturated compound with carbon monoxide and a hydroxyl group containing compound in the presence of a catalyst system as defined in the present invention. Preferably, the process is a liquid phase continuous process comprising the step noted above.

Suitably, the hydroxyl group containing compound includes water or an organic molecule having a hydroxyl functional group. Preferably, the organic molecule having a hydroxyl functional group may be branched or linear, and comprises an alkanol, particularly a $C_1$-$C_{30}$ alkanol, including aryl alkanols, which may be optionally substituted with one or more substituents selected from lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{28}$ as defined herein. Highly preferred alkanols are $C_1$-$C_8$ alkanols such as methanol, ethanol, propanol, iso-propanol, iso-butanol, t-butyl alcohol, n-butanol, phenol and chlorocapryl alcohol. Although the monoalkanols are most preferred, polyalkanols, preferably, selected from di-octa ols such as diols, triols, tetra-ols and sugars may also be utilised. Typically, such polyalkanols are selected from 1,2-ethanediol, 1,3-propanediol, glycerol, 1,2,4 butanetriol, 2-(hydroxymethyl)-1,3-propanediol, 1,2,6 trihydroxyhexane, pentaerythritol, 1,1,1 tri(hydroxymethyl)ethane, nannose, sorbase, galactose and other sugars. Preferred sugars include sucrose, fructose and glucose. Especially preferred alkanols are methanol and ethanol. The most preferred alkanol is methanol.

The amount of alcohol is not critical. Generally, amounts are used in excess of the amount of ethylenically unsaturated compound to be carbonylated. Thus the alcohol may serve as the reaction solvent as well, although, if desired, separate solvents may also be used.

It will be appreciated that the end product of the reaction is determined at least in part by the source of hydroxyl group containing compound used. If water is used as the hydroxyl group containing compound then the end product is the corresponding carboxylic acid, whereas use of an alkanol produces the corresponding ester.

It will also be appreciated that the process of the present invention may start with a catalyst system having components providing molar ratios above or below those claimed but such ratios will progress to values within said ranges claimed during the course of the reaction.

It will of course also be appreciated that the levels of such components present within the catalyst system may change during the process of the invention as further amounts of some or all of the components are added to maintain the usable levels of components within the catalyst system. Some of the components of the catalyst system may drop out of the system during the reaction process and therefore levels may need to be topped-up to maintain levels within the actual catalyst system.

As stated hereinbefore, it will be appreciated by those skilled in the art that the phosphines described herein may function as ligands that coordinate with the Group VIB or Group VIIIB metal or compound, together with the present acid, to form a complex. This complex may represent part of the effective catalyst in the present invention and hence may represent part of the catalyst system defined herein.

In the process according to the present invention, the carbon monoxide may be used in pure form or diluted with an inert gas such as nitrogen, carbon dioxide or a noble gas such as argon. Small amounts of hydrogen, typically less than 5% by volume, may also be present.

The ratio (volume/volume) of ethylenically unsaturated compound to hydroxyl group containing compound may vary between wide limits and suitably lies in the range of 1:0.1 to 1:10, preferably from between 2:1 to 1:2 and up to a large excess of hydroxyl group containing compounds when the latter is also the reaction solvent such as up to a 50:1 excess of hydroxyl group containing compounds.

The molar ratio of the ethylenically unsaturated compound to carbon monoxide is preferably in the range 1:1 to 100:1 more preferably greater than 1:1, even more preferably at least 3:1, especially from 3:1 to 50:1, and most preferably in the range from 3:1 to 15:1.

The total amount of dissolved Group VIB or VIIIB metal of the invention used in the carbonylation process of the ethylenically unsaturated compound is not critical. Good results may be obtained when, preferably, the amount of Group VIB or VIIIB metal is in the range $10^{-7}$ to $10^{-1}$ moles per mole of ethylenically unsaturated compound, more preferably, $10^{-6}$ to $10^{-2}$ moles, most preferably $10^{-5}$ to $10^{-2}$ moles per mole of ethylenically unsaturated compound. Preferably, the amount of bidentate compound of formula I or formula III to unsaturated compound is in the range $10^{-7}$ to $10^{-1}$, more prefer-ably, $10^{-6}$ to $10^{-2}$, most preferably, $10^{-5}$ to $10^{-2}$ moles per mole of ethylenically unsaturated compound.

Suitably, although non-essential to the invention, the carbonylation of an ethylenically unsaturated compound as defined herein may be performed in one or more aprotic solvents. Suitable solvents include ketones, such as for example methylbutylketone; ethers, such as for example anisole(methyl phenyl ether), 2,5,8-trioxanonane (diglyme), diethyl ether, dimethyl ether, tetrahydrofuran, diphenylether, diisopropylether and the dimethylether of di-ethylene-glycol; esters, such as for example methylacetate, dimethyladipate methyl benzoate, dimethyl phthalate and butyrolactone; amides, such as for example dimethylacetamide, N-methylpyrrolidone and dimethyl formamide; sulfoxides and sulphones, such as for example dimethylsulphoxide, di-isopropylsulphone, sulfolane (tetrahydrothiophene-2,2-dioxide), 2-methylsulfolane, diethyl sulphone, tetrahydrothiophene 1,1-dioxide and 2-methyl-4-ethylsulfolane; aromatic compounds, including halo variants of such compounds eg. benzene, toluene, ethyl benzene o-xylene, m-xylene, p-xylene, chlorobenzene, o-dichlorobenzene, m-dichlorobenzene: alkanes, including halo variants of such compounds eg. hexane, heptane, 2,2,3-trimethylpentane, methylene chloride and carbon tetrachloride; nitriles eg. benzonitrile and acetonitrile. Very suitable are aprotic solvents having a dielectric constant that is below a value of 50, more preferably in the range of 3 to 8, at 298.15 K and $1 \times 10^5$ $Nm^{-2}$. In the present context, the dielectric constant for a given solvent is used in its normal meaning of representing the ratio of the capacity of a condenser with that substance as dielectric to the capacity of the same condenser with a vacuum for dielectric. Values for the dielectric constants of common organic liquids can be found in general reference books, such as the Handbook of Chemistry and Physics, $76^{th}$ edition, edited by David R. Lide et al, and published by CRC press in 1995, and are usually quoted for a temperature of about 20° C. or 25° C., i.e. about 293.15 k or 298.15 K, and atmospheric pressure, i.e. about $1 \times 10^5$ $Nm^{-2}$, or can readily be converted to that temperature and pressure using the conversion factors quoted. If no literature data for a particular compound is available, the dielectric constant may be readily measured using established physicochemical methods.

For example, the dielectric constant of anisole is 4.3 (at 294.2 K), of diethyl ether is 4.3 (at 293.2 K), of sulfolane is 43.4 (at 303.2 K), of methylpentanoate is 5.0 (at 293.2 K), of diphenylether is 3.7 (at 283.2 K), of dimethyladipate is 6.8 (at 293.2 K), of tetrahydrofuran is 7.5 (at 295.2 K), of methylnonanoate is 3.9 (at 293.2 K). A preferred solvent is anisole.

If the hydroxyl group containing compound is an alkanol, an aprotic solvent will be generated by the reaction because the ester carbonylation product of the ethylenically unsaturated compound, carbon monoxide and the alkanol is an aprotic solvent.

The process may be carried out in an excess of aprotic solvent, i.e. at a ratio (v/v) of aprotic solvent to hydroxyl group containing compound of at least 1:1. Preferably, this ratio ranges from 1:1 to 10:1 and more preferably from 1:1 to 5:1. Most preferably the ratio (v/v) ranges from 1.5:1 to 4:1.

Despite the aforegoing it is preferred that the reaction is carried out in the absence of any external added aprotic solvent ie. an aprotic solvent not generated by the reaction itself.

The catalyst compounds of the present invention act as "homogeneous" catalysts.

By the term "homogeneous" catalyst we mean a catalyst, i.e. a compound of the invention, which is not supported but is simply admixed or formed in-situ with the reactants of the carbonylation reaction (e.g. the ethylenically unsaturated compound, the hydroxyl containing compound and carbon monoxide), preferably in a suitable solvent as described herein.

Conveniently, the process of the invention may be carried out by dissolving the Group VIB or VIIIB metal or compound thereof as defined herein in a suitable solvent such as one of the hydroxyl group containing compounds or aprotic solvents previously described (a particularly preferred solvent would be the ester or acid product of the specific carbonylation reaction e.g. Methyl propionate for ethylene carbonylation) and subsequently admixing with a compound of formula I or III as defined herein and an acid.

The carbon monoxide may be used in the presence of other gases which are inert in the reaction. Examples of such gases include hydrogen, nitrogen, carbon dioxide and the noble gases such as argon.

Suitable Group VIB or VIIIB metals or a compound thereof which may be combined with a compound of formula I or III include cobalt, nickel, palladium, rhodium, platinum, chromium, molybdenum and tungsten, and preferably include cobalt, nickel, palladium, rhodium and platinum. Preferably, the component b) is a Group VIIIB metal or a compound thereof. Preferably, the metal is a Group VIIIB metal, such as palladium. Preferably, the Group VIIIB metal is palladium or a compound thereof. Thus, component b) is preferably palladium or a compound thereof. Suitable compounds of such Group VIB or VIIIB metals include salts of such metals with, or compounds comprising weakly coordinated anions derived from, nitric acid; sulphuric acid; lower alkanoic (up to $C_{12}$) acids such as acetic acid and propionic acid; sulphonic acids such as methane sulphonic acid, chlorosulphonic acid, fluorosulphonic acid, trifluoromethane sulphonic acid, benzene sulphonic acid, naphthalene sulphonic acid, toluene sulphonic acid, e.g. p-toluene sulphonic acid, t-butyl sulphonic acid, and 2-hydroxypropane sulphonic acid; sulphonated ion exchange resins; perhalic acid such as perchloric acid; halogenated carboxylic acids such as trichloroacetic acid and trifluoroacetic acid; orthophosphoric acid; phosphonic acids such as benzenephosphonic acid; and acids derived from interactions between Lewis acids and Bronsted acids. Other sources which may provide suitable anions include the optionally halogenated tetraphenyl borate derivatives e.g. perfluorotetraphenyl borate. Additionally, zero valent palladium complexes particularly those with labile ligands, e.g. triphenylphosphine or alkenes such as dibenzylideneacetone or styrene or tri(dibenzylideneacetone)dipalladium may be used.

Thus, the acid (when present) is selected from an acid having a pKa measured in aqueous solution at 18° C. of less than 6, more preferably less than 5, most preferably less than 4, especially less than 3, more especially, less than 2. Suitable acids include the acids listed supra. Preferably, the acid is either a sulphonic acid, or some other acid such as those selected from the list consisting of perchloric acid, phosphoric acid, methyl phosphonic acid, sulphuric acid, and sulphonic acids, even more preferably a sulphonic acid or other acid (selected from the list above) having a pKa measured in aqueous solution at 18° C. of less than 4, yet even more preferably a sulphonic acid having a pKa measured in aqueous solution at 18° C. of less than 2, still more preferably the acid is selected from the list consisting of the following sulphonic acids: methanesulphonic acid, trifluoromethanesulphonic acid, tert-butanesulphonic acid, p-toluenesulphonic acid, 2-hydroxypropane-2-sulphonic acid, and 2,4,6-trimethylbenzenesulphonic acid, most preferably the acid is methanesulphonic acid.

The anion may be derived from or introduced as one or more of an acid having a pKa measured in aqueous solution at 18° C. of less than 6, more preferably, less than 5, most preferably, less than 4, especially less than 3, a salt with a cation that does not interfere with the reaction, e.g. metal salts or largely organic salts such as alkyl ammonium, and a precursor, such as an ester, that can break down under reaction conditions to generate the anion in situ. Suitable acids and salts include the acids and salts, listed supra.

The quantity of anion present is not critical to the catalytic behaviour of the catalyst system. The molar ratio of anion to metal may be from 1:1 to 500:1, preferably from 2:1 to 100:1 and particularly from 3:1 to 30:1. Where the anion is provided by a combination of acid and salt, the relative proportion of the acid and salt is not critical.

As mentioned, the catalyst system of the present invention is typically used homogeneously.

The catalyst system of the present invention is preferably constituted in the liquid phase which may be formed by one or more of the reactants or by the use of a suitable solvent.

The molar ratio of the amount of ethylenically unsaturated compound used in the reaction to the amount of hydroxyl providing compound is not critical and may vary between wide limits, e.g. from 0.001:1 to 100:1 mol/mol.

The product of the carbonylation reaction using the ligand of the invention may be separated from the other components by any suitable means. However, it is an advantage of the present process that significantly fewer by-products are formed thereby reducing the need for further purification after the initial separation of the product as may be evidenced by the generally significantly higher selectivity. A further advantage is that the other components which contain the catalyst system which may be recycled and/or reused in further reactions with minimal supplementation of fresh catalyst.

Preferably, the carbonylation is carried out at a temperature of between −10 to 150° C., more preferably 0° C. to 140° C., even more preferably 15° C. to 140° C., most preferably 20° C. to 120° C. An especially preferred temperature is one chosen between 80° C. to 120° C. Advantageously, the carbonylation can be carried out at moderate temperatures.

Preferably, when operating a low temperature carbonylation, the carbonylation is carried out between −30° C. to 49° C., more preferably, 10° C. to 45° C., still more preferably 0° C. to 45° C., even more preferably 10° C. to 45° C., most preferably 15° C. to 45° C. Especially preferred is a range of 15 to 35° C.

Preferably, the carbonylation is carried out at a CO partial pressure of between $0.80 \times 10^5$ N·m$^{-2}$ to $90 \times 10^5$ N·m$^{-2}$, more preferably, $1 \times 10^5$ N·m$^{-2}$ to $65 \times 10^5$ N·m$^{-2}$ and most preferably 1 to $30 \times 10^5$ N·m$^{-2}$. Especially preferred is a CO partial pressure of 5 to $20 \times 10^5$ N·m$^{-2}$.

Preferably, a low pressure carbonylation is also envisaged. Preferably, when operating a low pressure carbonylation the carbonylation is carried out at a CO partial pressure of between 0.1 to $5 \times 10^5$ N·m$^{-2}$, more preferably 0.2 to $2 \times 10^5$ N·m$^{-2}$ and most preferably 0.5 to $1.5 \times 10^5$ N·m$^{-2}$.

The ethylenically unsaturated compounds may be substituted or non-substituted with groups as defined above for the "aryl" group above. Particularly suitable substituents include alkyl and aryl groups as well as groups containing heteroatoms such as halides, sulphur, phosphorus, oxygen and nitrogen. Examples of substituents include chloride, bromide, iodide and hydroxy, alkoxy, carboxy, amino, amido, nitro, cyano, thiol or thioalkoxy groups. Suitable ethylenically unsaturated compounds include ethene, propene, hexene, vinyl compounds such as vinyl acetates, heptene, octene, nonene, decene, undecene, dodecene, etc up to $C_{30}$, i.e. having from 2 to 30 carbon atoms, which may be linear or branched, cyclic or uncyclic or part cyclic and in which the double bond may take any suitable position in the carbon chain and which includes all stereoisomers thereof.

Moreover, the unsaturated compound may have one or more unsaturated bonds and therefore, for example, the range of ethylenically unsaturated compounds extends to dienes. The unsaturated bond(s) may be internal or terminal, the catalyst system of the invention being particularly advantageous in the conversion of internal olefins.

Particularly preferred are olefins having from 2 to 22 carbon atoms per molecule, such as ethene, propene, 1-butene, 2-butene, isobutene, pentenes, hexenes, octenes, e.g. oct-2-ene, oct-3-ene, oct-4-ene, decenes and dodecenes, triisobutylene, tripropylene, internal $C_{14}$ olefins, and internal $C_{15}$-$C_{18}$ olefins, 1,5-cyclooctadiene, cyclododecene, methyl pentenoate and pentene nitriles, e.g. pent-2-ene nitrile.

The ethylenically unsaturated compound is preferably an alkene having 1 to 3 carbon-carbon double bonds per molecule. Non-limiting examples of suitable dienes include the following: 1,3-butadiene, 2-methyl-1,3-butadiene, 1,5-cyclooctadiene, 1,3-cyclohexadiene, 2,4-heptadiene, 1,3-pentadiene, 1,3-hexadiene, particularly 1,3-butadiene.

Another preferred category of unsaturated compounds consists of unsaturated esters of carboxylic acids and esters of unsaturated carboxylic acids. For example, the starting material may be a vinyl ester of a carboxylic acid such as acetic acid or propanoic acid, or it may be an alkyl ester of an unsaturated acid, such as the methyl or ethyl ester of acrylic acid or methacrylic acid.

A further preferred category of unsaturated compounds consists of cycloalkadienes, which will ordinarily refuse carbonylation. For example, the starting material may be dicyclopentadiene or norbornadiene, to give diesters, diamides or diacids, etc., which may find subsequent use as monomers in polymerisation reactions.

The use of stabilising compounds with the catalyst system may also be beneficial in improving recovery of metal which has been lost from the catalyst system. When the catalyst system is utilized in a liquid reaction medium such stabilizing compounds may assist recovery of the Group VI or VIIIB metal.

Preferably, therefore, the catalyst system includes in a liquid reaction medium a polymeric dispersant dissolved in a liquid carrier, said polymeric dispersant being capable of stabilising a colloidal suspension of particles of the Group VI or VIIIB metal or metal compound of the catalyst system within the liquid carrier.

The liquid reaction medium may be a solvent for the reaction or may comprise one or more of the reactants or reaction products themselves. The reactants and reaction products in liquid form may be miscible with or dissolved in a solvent or liquid diluent.

The polymeric dispersant is soluble in the liquid reaction medium, but should not significantly increase the viscosity of the reaction medium in a way which would be detrimental to reaction kinetics or heat transfer. The solubility of the dispersant in the liquid medium under the reaction conditions of temperature and pressure should not be so great as to deter significantly the adsorption of the dispersant molecules onto the metal particles.

The polymeric dispersant is capable of stabilising a colloidal suspension of particles of said Group VI or VIIIB metal or metal compound within the liquid reaction medium such that the metal particles formed as a result of catalyst degradation are held in suspension in the liquid reaction medium and are discharged from the reactor along with the liquid for reclamation and optionally for re-use in making further quantities of catalyst. The metal particles are normally of colloidal dimensions, e.g. in the range 5-100 nm average particle size although larger particles may form in some cases. Portions of the polymeric dispersant are adsorbed onto the surface of the metal particles whilst the remainder of the dispersant molecules remain at least partially solvated by the liquid reaction medium and in this way the dispersed Group VI or VIIIB metal particles are stabilised against settling on the walls of the reactor or in reactor dead spaces and against forming agglomerates of metal particles which may grow by collision of particles and eventually coagulate. Some agglomeration of particles may occur even in the presence of a suitable dispersant but when the dispersant type and concentration is optimised then such agglomeration should be at a relatively low level and the agglomerates may form only loosely so that they may be broken up and the particles redispersed by agitation.

The polymeric dispersant may include homopolymers or copolymers including polymers such as graft copolymers and star polymers.

Preferably, the polymeric dispersant has sufficiently acidic or basic functionality to substantially stabilise the colloidal suspension of said Group VI or VIIIB metal or metal compound.

By substantially stabilise is meant that the precipitation of the Group VI or VIIIB metal from the solution phase is substantially avoided.

Particularly preferred dispersants for this purpose include acidic or basic polymers including carboxylic acids, sulphonic acids, amines and amides such as polyacrylates or heterocycle, particularly nitrogen heterocycle, substituted polyvinyl polymers such as polyvinyl pyrrolidone or copolymers of the aforesaid.

Examples of such polymeric dispersants may be selected from polyvinylpyrrolidone, polyacrylamide, polyacrylonitrile, polyethylenimine, polyglycine, polyacrylic acid, polymethacrylic acid, poly(3-hydroxybutyric acid), poly-L-leucine, poly-L-methionine, poly-L-proline, poly-L-serine, poly-L-tyrosine, poly(vinylbenzenesulphonic acid) and poly (vinylsulphonic acid).

Other suitable polymeric dispersants are nitrogen-containing polymers which are solubilizable in the reaction mixture and their methods of preparation are described in EP1330309 which are hereby incorporated by reference. Examples of suitable polymers described therein are polyalkylenimines, in particular polyethylenimines; polyvinylamines having aliphatic nitrogen-containing radicals on the polymer chain; polymers of ethylenically unsaturated carboxamides such as poly(meth)acrylamides; polymers of acyclic or cyclic N-vinyl amides such as polyvinylformamide or polyvinylcaprolactam. The polymers can have different nitrogen-containing monomers and, if desired, nitrogen-free monomers in one molecule. The nitrogen atoms may be present in the main chain or in side groups. In the case of such polymers containing amino groups, they bear, for example, substituents such as alkyl, aryl, acyl or polyoxyalkylene groups on some or all of the amino groups Preference is given to using polyethylenimines as solubilizable nitrogen-containing polymers. They preferably comprise the polyethylenimine units of the formula (I) or (III) or the branched isomers thereof

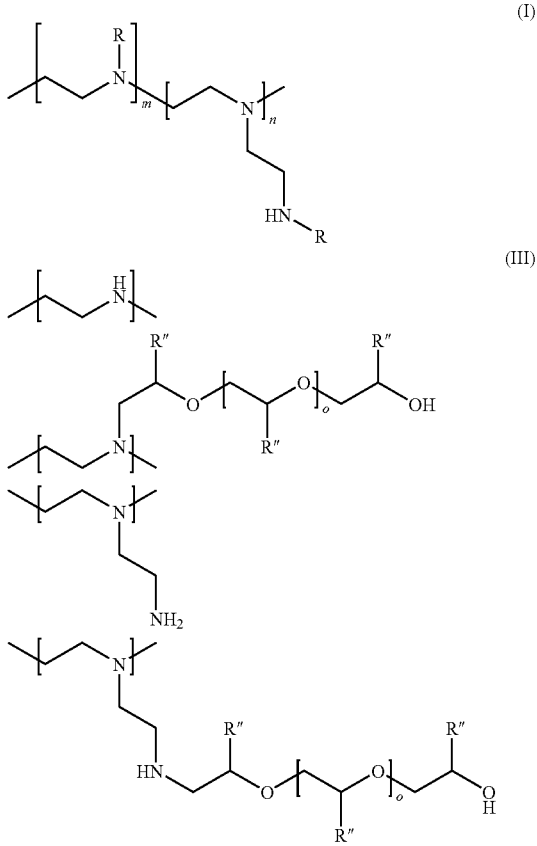

Further compounds described are derivatives of polyvinylamine which have aliphatic nitrogen-containing groups on the polymer chain and comprise, as the characteristic structural element, units of the formula (IV)

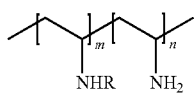

Still further compounds suitable are derivatives of polyacrylamide which comprise, as characteristic structural elements, units of the formula (V)

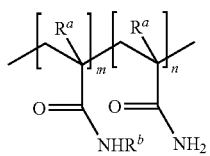

A particularly preferred polymer is amidated polyethylenimine as described in EP1330309.

Other alternatives are the solubilizable carboxamides described in US publication 2003/0069450 and all such carboxamides are incorporated herein by reference. Generally, the carboxamides disclosed therein have at least one carboxamide group of the formula —CO—N< Such carboxamides can be, for example, saturated or unsaturated, aliphatic, aromatic or araliphatic compounds. Furthermore, the carboxamide can contain one or more heteroatoms such as oxygen, nitrogen, sulfur or phosphorus, for example —O—, —S—, —NH—, —NR—, —CO—, —CO—O—, —N—, —CO—N<, —SiR2-, —PR— and/or —PR2 and/or be substituted by one or more functional groups containing, for example, oxygen, nitrogen, sulfur and/or halogen atoms.

Very particularly preferred carboxamides disclosed therein and having one carboxamide group of the formula —CO—N< in the molecule are N,N-dimethylacetamide, N,N-diethylacetamide, N,N-dipropylacetamide, N,N-diisopropylacetamide, N,N-dibutylacetamide, N,N-diisobutylacetamide, N,N-dipentylacetamide, N,N-dihexylacetamide, N,N-dioctylacetamide, N,N-dimethylpropionamide, N,N-diethylpropionamide, N,N-dipropylpropionamide, N,N-diisopropylpropionamide, N,N-dibutylpropionamide, N,N-diisobutylpropionamide, N,N-dipentylpropionamide, N,N-dihexylpropionamide and N,N-dioctylpropionamide.

Suitable examples of oligomeric and polymeric carboxamides given are acylated oligoalkylenimines and polyalkylenimines, in particular acylated oligoethylenimines and polyethylenimines; acylated oligovinylamines and polyvinylamines; oligomers and polymers of ethylenically unsaturated carboxamides, for example oligoacrylamides and polyacrylamides or oligomethacrylamides and polymethacrylamides; and oligomers and polymers of acyclic and cyclic N-vinyl amides, for example oligovinylformamides and polyvinylformamides or oligovinylcaprolactams and polyvinylcaprolactams.

Preferably, the polymeric dispersant incorporates acidic or basic moieties either pendant or within the polymer backbone. Preferably, the acidic moieties have a dissociation constant ($pK_a$) of less than 6.0, more preferably, less than 5.0, most preferably less than 4.5. Preferably, the basic moieties have a base dissociation constant ($pK_b$) being of less than 6.0, more preferably less than 5.0 and most preferably less than 4.5, $pK_a$ and $pK_b$ being measured in dilute aqueous solution at 25° C.

Suitable polymeric dispersants, in addition to being soluble in the reaction medium at reaction conditions, contain at least one acidic or basic moiety, either within the polymer backbone or as a pendant group. We have found that polymers incorporating acid and amide moieties such as polyvinylpyrollidone (PVP) and polyacrylates such as polyacrylic acid (PAA) are particularly suitable. The molecular weight of the polymer which is suitable for use in the invention depends upon the nature of the reaction medium and the solubility of the polymer therein. We have found that normally the average molecular weight is less than 100,000. Preferably, the average molecular weight is in the range 1,000-200,000, more preferably, 5,000-100,000, most preferably, 10,000-40,000 e.g. Mw is preferably in the range 10,000-80,000, more preferably 20,000-60,000 when PVP is used and of the order of 1,000-10,000 in the case of PAA.

The effective concentration of the dispersant within the reaction medium should be determined for each reaction/catalyst system which is to be used.

The dispersed Group VI or VIIIB metal may be recovered from the liquid stream removed from the reactor e.g. by filtration and then either disposed of or processed for re-use as a catalyst or other applications. In a continuous process the liquid stream may be circulated through an external heat-exchanger and in such cases it may be convenient to locate filters for the palladium particles in these circulation apparatus.

Preferably, the polymer:metal mass ratio in g/g is between 1:1 and 1000:1, more preferably, between 1:1 and 400:1, most preferably, between 1:1 and 200:1. Preferably, the polymer: metal mass ratio in g/g is up to 1000, more preferably, up to 400, most preferably, up to 200.

Preferably, said reaction medium is a liquid-phase reaction medium, more preferably a liquid-phase continuous-system reaction system.

Preferably, within said reaction medium, the amount of free acid present in the medium, that is acid which is not directly combined with the phosphine ligand, is greater than 500 ppm, more preferably greater than 1000 ppm, most preferably greater than 2000 ppm.

For the avoidance of any doubt, each and every feature described hereinbefore is equally applicable to any or all of the various aspects of the present invention as set out supra., unless such features are incompatible with the particular aspect or are mutually exclusive.

All documents mentioned herein are incorporated by reference thereto.

The following examples and figures further illustrate the present invention. These examples are to be viewed as being illustrative of specific materials falling within the broader disclosure presented above and are not to be viewed as limiting the broader disclosure in any way.

FIG. 1 shows a plot of TON vs ACCF for examples 1-5 and 7 and comparative example 6, based upon data from the series of examples shown in Table 1. Table 2 shows data from examples 8-11.

PREPARATIVE EXAMPLE 1

Preparation of 1,2-bis-(ditertbutylphosphinomethyl)benzene

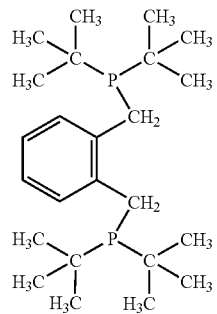

1,2-bis-(di-tert-butylphosphinomethyl)benzene

The preparation of this ligand was carried out in the manner disclosed in WO 99/47528 in accordance with Example 18.

PREPARATIVE EXAMPLE 2

Preparation of 1,2-bis-(di-(dimethyladamantyl)phosphinomethyl)ferrocene

The preparation of this ligand was carried out in the manner disclosed in WO 03/003936, in accordance with Example 1.

EXAMPLES 1-5 AND 7 AND COMPARATIVE EXAMPLE 6

Preparation of Methyl Propanoate from Ethylene, Carbon Monoxide and Methanol Catalysed According to the Present Invention The continuous process exemplified involved the reaction of purified streams of carbon monoxide, ethylene and methanol in the liquid phase, in the presence of a catalyst system, to generate the desired product, methyl propanoate.

The reaction was carried out at 100° C. and at 12 barg pressure in the reactor vessel.

The catalyst system was made up of three components, being a palladium salt, a phosphine ligand and an acid. The three catalyst components, when combined together and dissolved in the reaction mixture, constitute the reaction catalyst or catalyst system, a homogeneous catalyst, which converted dissolved reactants to the product methyl propanoate in the liquid phase.

During continuous operation, the catalyst decomposed at a slow but steady rate, and was replaced by adding fresh catalyst, or the rate of generation of the product, methyl propanoate reduces.

The reactor vessel was fitted with an agitator, and also a means of re-circulating the unreacted gas that collected in the upper headspace area of the reactor. The unreacted gas from the reactor vessel headspace, which was made up of a mixture of ethylene and carbon monoxide, was returned continuously to the reactor via an entry pipe at the base, such that the gas passed up through the reaction mixture continuously.

Upon entering into the reactor vessel the gas was dispersed by the agitator into fine bubbles. In this way the ethylene and carbon monoxide were dissolved in the reaction mix.

Fresh ethylene and carbon monoxide gases were added to the re-circulating gas to make up for the amount of the two gases that have been used up by the reaction. Fresh methanol was also added continuously to the reactor vessel, in order to replace the methanol that has been used up in the reaction.

The reactor vessel held the bulk liquid reaction mixture, along with the three components of the homogeneous catalyst, being a palladium salt, a phosphine ligand, and a sulphonic acid.

In order to recover the product methyl propanoate, a stream of reaction mixture was passed continuously out of the reactor and into the distillation column.

The distillation column, being a single stage 'flash' type distillation column, provided a means of separating a fraction of the methyl propanoate and methanol components of the reaction mixture from the non-volatile dissolved catalyst components. This was achieved by vaporising a fraction of the reaction mixture as it passed through the flash column. The part of the reaction mixture which remained as liquid after passing through the flash column, and which still contained useful catalyst components, was returned to the reactor vessel so that the catalyst components could take part in the on-going reaction.

If the methyl propanoate product was required free of methanol, a second distillation column was required. In this case, the vapour stream from the flash column, which is a mixture of methyl propanoate and methanol was passed into the second distillation column, where the pure methyl propanoate was generated as the heavier product, and taken off from the base of the column. A low boiling mixture of methanol and methyl propanoate was generated as the light product, and was removed continuously from the top of the MeP purification column. In order to utilise the methanol as efficiently as possible in the process, the low boiling mixture of methanol and methyl propanoate was returned continuously to the reactor vessel.

After start up of the continuous reactor unit, when the desired rate of generation of methyl propanoate had been achieved, a process of gradual reduction of the feed rates of the catalyst components was undertaken.

In order to sustain the rate of generation of methyl propanoate it was necessary to continuously replace the palladium catalyst component which was lost to decomposition with fresh palladium at a rate which balanced the rate of loss.

This led to the situation where the standing concentrations of catalyst components became constant for a given rate of generation of methyl propanoate, and just able to sustain flow sheet reaction rate, as indicated by constant concentrations of carbon monoxide and ethylene in the headspace area of the reactor vessel. This was called the balance point, because under these conditions the rate of palladium decomposition was balanced exactly by the rate of addition of fresh palladium.

From the rate of addition of fresh palladium catalyst component under balance point conditions, the palladium turnover number (TON) was calculated. This is defined as the number of mol of methyl propanoate generated per hour, for each mol of palladium consumed by the decomposition process per hour.

Upon reaching a steady state at a predetermined set of control conditions, the instantaneous values of all of the variables were recorded, and used as representative data to show the performance of the process under the conditions in use at the time.

To gather data on the effect of ACCF on palladium turnover number, all variables were held constant except the levels of solvent in the reaction mixture. These levels were changed to a high level, a comparative low level and 5 comparative average levels to generate a reliable control level. The additions were then followed by careful adjustment to make sure the rate of production of methyl propanoate remained constant.

In this way, comparative sets of results were drawn up which showed clearly the changes to catalyst stability that were caused by the variations in the ACCF.

The amount of palladium in the feed to the reactor is critical to calculation of turnover number results. Assurance on the rate of fresh catalyst being fed to the system was provided by analysis of each batch of catalyst prior to transfer to the catalyst feed tanks for palladium content. Further assurance was gained by determination of the actual feed rate of catalyst from timing of the fall in the level in a burette, which is part of the catalyst feed system.

Table 1 shows the effect of ACCF on palladium turnover number (TON) for results obtained for examples 1-5 and 7 and comparative example 6.

In examples 1-5 and 7 and comparative example 6, the acid used was methanesulphonic acid, the bidentate phosphine ligand was 1,2-bis-(ditertbutylphosphinomethyl)benzene, and the palladium compound was tri(dibenzylideneacetone) dipalladium.

The results from comparative example 6, examples 1-5 and example 7 are shown more clearly in FIG. 1 which shows a plot of TON vs ACCF. As can be seen, at low ACCF the TON surprisingly increases.

Table 1 shows the actual measured levels of Palladium at the different data points, as well as the calculated ACCF factors and resulting Pd turnover numbers.

Table 2 shows the effect of ACCF on palladium turnover number (TON), obtained for examples 8-11. It shows the calculated ACCF factors and resulting Pd turnover numbers.

In examples 8-11, the acid used was methanesulphonic acid, the bidentate phosphine ligand was 1,2-bis-(di(dimethyladamantyl)phosphinomethyl)ferrocene, and the palladium compound was tri(dibenzylideneacetone)dipalladium.

TABLE 2

|  | Ex. 8 | Ex. 9 | Ex. 10 | Ex. 11 |
|---|---|---|---|---|
| Volume of Liquid Phase reactor (ml, 20 C.) | 2600 | 2600 | 2600 | 3600 |
| Pure MeP rate (g/hr, by weight difference) | 1030 | 1035 | 1032 | 1030 |
| Turn Over Number (mol MeP/Mol Pd) | 10712078 | 10803755 | 11707192 | 19816656 |
| Pd (ppm) | n/m | n/m | n/m | n/m |
| 'P' (ppm) | n/m | n/m | n/m | n/m |
| Acid (ppm) | 1621 | n/m | n/m | 1137 |
| ACCF (Kg MeP hr$^{-1}$ dm$^{-3}$) | 0.38 | 0.38 | 0.38 | 0.28 |

Although some preferred embodiments have been shown and described, it will be appreciated by those skilled in the art that various changes and modifications might be made without departing from the scope of the present invention, as defined in the appended claims.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be

TABLE 1

|  | Ex. 1 | Ex. 7 | Comp. Ex. 6 | Ex. 2 | Ex. 3 | Ex. 4 | Ex. 5 |
|---|---|---|---|---|---|---|---|
| Volume of Liquid Phase reactor (ml, 20 C.) | 2600 | 3600 | 1600 | 2600 | 2600 | 2600 | 2600 |
| Pure MeP rate (g/hr, by weight difference) | 1000 | 1000 | 1000 | 1000 | 1000 | 1023 | 1024 |
| Turn Over Number (mol MeP/Mol Pd) | 5967054 | 11474335 | 4319287 | 6046196 | 6341425 | 6616618 | 6007141 |
| Pd (ppm) | 5.8 | 5.4 | 7.6 | 5.1 |  |  |  |
| 'P' (ppm) | 30 | 32 | 40 | 34 |  |  |  |
| Acid (ppm) | 1105 | 1086 | 1190 | 1177 |  |  |  |
| ACCF (Kg MeP hr$^{-1}$ dm$^{-3}$) | 0.38 | 0.28 | 0.63 | 0.38 | 0.38 | 0.39 | 0.39 | combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A continuous carbonylation process for high turnover carbonylation comprising carbonylating an ethylenically unsaturated compound selected from the group consisting of ethene, propene, 1-butene, 2-butene, isobutene, pentenes, hexenes, heptene, octenes, nonene, decenes, undecene and dodecenes, triisobutylene, tripropylene, internal $C_{14}$-$C_{18}$ olefins, cyclododecene, methyl pentenoate, pentene nitriles, vinyl esters of a carboxylic acid, and an alkyl ester of an unsaturated acid, wherein the ethylenically unsaturated compound may be linear or branched, cyclic or uncyclic or part cyclic and in which the double bond may take any suitable position in the carbon chain and which includes all stereoisomers thereof, with carbon monoxide in the presence of a source of hydroxyl groups and a catalyst system comprising:
(a) a bidentate phosphine, arsine or stibine ligand of formula I or III

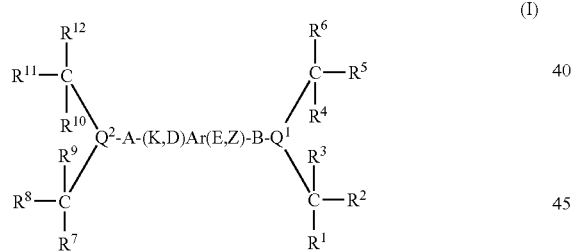

wherein:
Ar is an optionally substituted 6-membered aryl moiety;
A and B each independently represent lower alkylene;
K, D, E and Z are substituents of the aryl moiety (Ar) and each independently represent hydrogen, lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$, $C(O)SR^{27}$, or $-J-Q^3(CR^{13}(R^{14})(R^{15}))CR^{16}(R^{17})(R^{18})$ where J represents lower alkylene; or two adjacent groups selected from K, Z, D and E together with the carbon atoms of the aryl ring to which they are attached form a further phenyl ring, which is optionally substituted by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{27}$;
$R^{13}$ to $R^{18}$ each independently represent hydrogen, lower alkyl, aryl, or Het;
$R^{19}$ to $R^{27}$ each independently represent hydrogen, lower alkyl, aryl or Het;
$R^1$ to $R^{12}$ each independently represent hydrogen, lower alkyl, aryl, or Het;
$Q^1$, $Q^2$ and $Q^3$ (when present) each independently represent phosphorus, arsenic or antimony;
the $Q^1$, $Q^2$ or $Q^3$ (when present) atoms are linked on available adjacent carbon atoms to the optionally substituted aryl moiety;

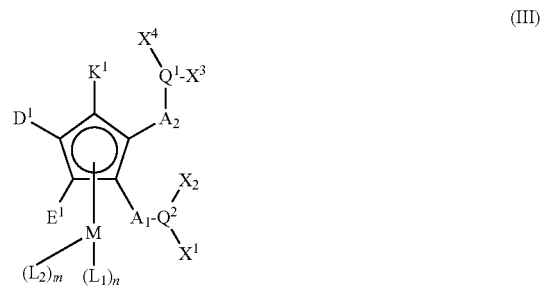

wherein:
$A_1$ and $A_2$, and $A_3$, $A_4$ and $A_5$ (when present), each independently represent lower alkylene;
$K^1$ is selected from the group consisting of hydrogen, lower alkyl, aryl, Het, halo, cyano, nitro, $-OR^{19}$, $-OC(O)R^{20}$, $-C(O)R^{21}$, $-C(O)OR^{22}$, $-N(R^{23})R^{24}$, $-C(O)N(R^{25})R^{26}$, $-C(S)(R^{27})R^{28}$, $-SR^{29}$, $-C(O)SR^{30}$, $-CF_3$ or $-A_3$-$Q^3(X^5)X^6$;
$D^1$ is selected from the group consisting of hydrogen, lower alkyl, aryl, Het, halo, cyano, nitro, $-OR^{19}$, $-OC(O)R^{20}$, $-C(O)R^{21}$, $-C(O)OR^{22}$, $-N(R^{23})R^{24}$, $-C(O)N(R^{25})R^{26}$, $-C(S)(R^{27})R^{28}$, $-SR^{29}$, $-C(O)SR^{30}$, $-CF_3$ or $-A_4$-$Q^4(X^7)X^8$;
$E^1$ is selected from the group consisting of hydrogen, lower alkyl, aryl, Het, halo, cyano, nitro, $-OR^{19}$, $-OC(O)R^{20}$, $-C(O)R^{21}$, $-C(O)OR^{22}$, $-N(R^{23})R^{24}$, $-C(O)N(R^{25})R^{26}$, $-C(S)(R^{27})R^{28}$, $-SR^{29}$, $-C(O)SR^{30}$, $-CF_3$ or $-A_5$-$Q^5(X^9)X^{10}$;
or both $D^1$ and $E^1$ together with the carbon atoms of the cyclopentadienyl ring to which they are attached form an optionally substituted phenyl ring;
$X^1$ represents $CR^1(R^2)(R^3)$, congressyl or adamantyl, $X^2$ represents $CR^4(R^5)(R^6)$, congressyl or adamantyl, or $X^1$ and $X^2$ together with $Q^2$ to which they are attached form an optionally substituted 2-phospha-tricyclo[3.3.1.1{3,7}]decyl group or derivative thereof, or $X^1$ and $X^2$ together with $Q^2$ to which they are attached form a ring system of formula IIIa

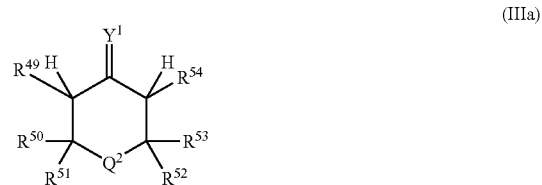

$X^3$ represents $CR^7(R^8)(R^9)$, congressyl or adamantyl, $X^4$ represents $CR^{10}(R^{11})(R^{12})$, congressyl or adamantyl, or $X^3$ and $X^4$ together with $Q^1$ to which they are attached form an optionally substituted 2-phospha-tricyclo[3.3.1.1{3,7}]decyl group or derivative thereof, or $X^3$ and $X^4$ together with $Q^1$ to which they are attached form a ring system of formula IIIb

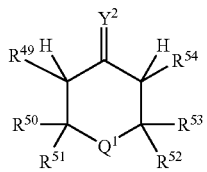

(IIIb)

$X^5$ represents $CR^{13}(R^{14})(R^{15})$, congressyl or adamantyl, $X^6$ represents $CR^{16}(R^{17})(R^{18})$, congressyl or adamantyl, or $X^5$ and $X^6$ together with $Q^3$ to which they are attached form an optionally substituted 2-phospha-tricyclo[3.3.1.1{3,7}]decyl group or derivative thereof, or $X^5$ and $X^6$ together with $Q^3$ to which they are attached form a ring system of formula IIIc

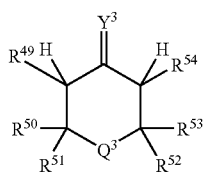

(IIIc)

$X^7$ represents $CR^{31}(R^{32})(R^{33})$, congressyl or adamantyl, $X^8$ represents $CR^{34}(R^{35})(R^{36})$, congressyl or adamantyl, or $X^7$ and $X^8$ together with $Q^4$ to which they are attached form an optionally substituted 2-phospha-tricyclo[3.3.1.1 {3,7}]decyl group or derivative thereof, or $X^7$ and $X^8$ together with $Q^4$ to which they are attached form a ring system of formula IIId

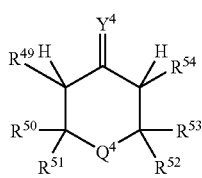

(IIId)

$X^9$ represents $CR^{37}(R^{38})(R^{39})$, congressyl or adamantyl, $X^{10}$ represents $CR^{40}(R^{41})(R^{42})$, congressyl or adamantyl, or $X^9$ and $X^{10}$ together with $Q^5$ to which they are attached form an optionally substituted 2-phospha-tricyclo[3.3.1.1.{3,7}]decyl group or derivative thereof, or $X^9$ and $X^{10}$ together with $Q^5$ to which they are attached form a ring system of formula IIIe

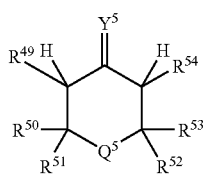

(IIIe)

and in this yet further embodiment, $Q^1$ and $Q^2$, and $Q^3$, $Q^4$ and $Q^5$ (when present), each independently represent phosphorus, arsenic or antimony;

M represents a Group VIB or VIIIB metal or metal cation thereof;

$L_1$ represents an optionally substituted cyclopentadienyl, indenyl or aryl group;

$L_2$ represents one or more ligands each of which are independently selected from hydrogen, lower alkyl, alkylaryl, halo, CO, $P(R^{43})(R^{44})R^{45}$ or $N(R^{46})(R^{47})R^{48}$;

$R^1$ to $R^{18}$ and $R^{31}$ to $R^{42}$, when present, each independently represent hydrogen, lower alkyl, aryl, halo or Het;

$R^{19}$ to $R^{30}$ and $R^{43}$ to $R^{48}$, when present, each independently represent hydrogen, lower alkyl, aryl or Het;

$R^{49}$, $R^{54}$ and $R^{55}$, when present, each independently represent hydrogen, lower alkyl or aryl;

$R^{50}$ to $R^{53}$, when present, each independently represent hydrogen, lower alkyl, aryl or Het;

$Y^1$, $Y^2$, $Y^3$, $Y^4$ and $Y^5$, when present, each independently represent oxygen, sulfur or N—$R^{55}$;

n=0 or 1;

and m=0 to 5;

provided that when n=1 then m equals 0, and when n equals 0 then m does not equal 0; and (b) palladium or a compound thereof in a continuous carbonylation process, wherein the ACCF (product kg·hr$^{-1}$·dm$^{-3}$) is held at less than 0.5.

2. A carbonylation reaction medium and product stream thereof for a continuous carbonylation process comprising in the reaction medium an ethylenically unsaturated compound selected from the group consisting of ethene, propene, 1-butene, 2-butene, isobutene, pentenes, hexenes, heptene, octenes, nonene, decenes, undecene and dodecenes, triisobutylene, tripropylene, internal $C_{14}$-$C_{18}$ olefins, cyclododecene, methyl pentenoate, pentene nitriles, vinyl esters of a carboxylic acid, and an alkyl ester of an unsaturated acid, wherein the ethylenically unsaturated compound may be linear or branched, cyclic or uncyclic or part cyclic and in which the double bond may take any suitable position in the carbon chain and which includes all stereoisomers thereof, carbon monoxide, a source of hydroxyl groups and a catalyst system comprising:

(a) a bidentate phosphine, arsine or stibene ligand of formula I or III,

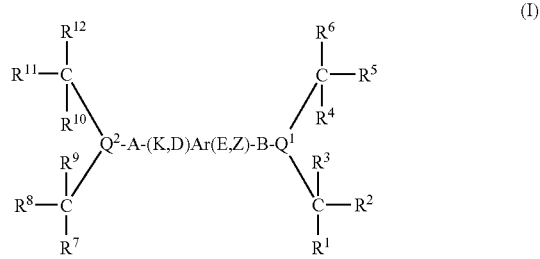

(I)

wherein:

Ar is an optionally substituted 6-membered aryl moiety;

A and B each independently represent lower alkylene;

K, D, E and Z are substituents of the aryl moiety (Ar) and each independently represent hydrogen, lower alkyl, aryl, Het, halo, cyano, nitro, $OR^{19}$, $OC(O)R^{20}$, C(O)

$R^{21}$, $C(O)OR^{22}$, $NR^{23}R^{24}$, $C(O)NR^{25}R^{26}$, $C(S)R^{25}R^{26}$, $SR^{27}$, $C(O)SR^{27}$, or $-J-Q^3(CR^{13}(R^{14})(R^{15})CR^{16}(R^{17})(R^{18})$ where J represents lower alkylene; or two adjacent groups selected from K, Z, D and E together with the carbon atoms of the aryl ring to which they are attached form a further phenyl ring, which is optionally substituted by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{27}$;

$R^{13}$ to $R^{18}$ each independently represent hydrogen, lower alkyl, aryl, or Het;

$R^{19}$ to $R^{27}$ each independently represent hydrogen, lower alkyl, aryl or Het;

$R^1$ to $R^{12}$ each independently represent hydrogen, lower alkyl, aryl, or Het;

$Q^1$, $Q^2$ and $Q^3$ (when present) each independently represent phosphorus, arsenic or antimony;

the $Q^1$, $Q^2$ or $Q^3$ (when present) atoms are linked on available adjacent carbon atoms to the optionally substituted aryl moiety;

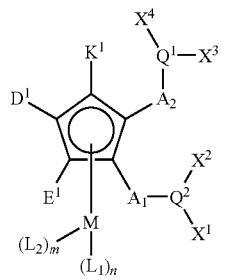

(III)

wherein:

$A_1$ and $A_2$, and $A_3$, $A_4$ and $A_5$ (when present), each independently represent lower alkylene;

$K^1$ is selected from the group consisting of hydrogen, lower alkyl, aryl, Het, halo, cyano, nitro, $-OR^{19}$, $-OC(O)R^{20}$, $-C(O)R^{21}$, $-C(O)OR^{22}$, $-N(R^{23})R^{24}$, $-C(O)N(R^{25})R^{26}$, $-C(S)(R^{27})R^{28}$, $-SR^{29}$, $-C(O)SR^{30}$, $-CF_3$ or $-A_3-Q^3(X^5)X^6$;

$D^1$ is selected from the group consisting of hydrogen, lower alkyl, aryl, Het, halo, cyano, nitro, $-OR^{19}$, $-OC(O)R^{20}$, $-C(O)R^{21}$, $-C(O)OR^{22}$, $-N(R^{23}R^{24}$, $-C(O)N(R^{25})R^{26}$, $-C(s)(R^{27})R^{28}$, $-SR^{29}$, $-C(O)SR^{30}$, $-CF_3$ or $-A_4-Q^4(X^7)X^8$;

$E^1$ is selected from the group consisting of hydrogen, lower alkyl, aryl, Het, halo, cyano, nitro, $-OR^{19}$, $-OC(O)R^{20}$, $-C(O)R^{21}$, $-C(O)OR^{22}$, $-N(R^{23})R^{24}$, $-C(O)N(R^{25})R^{26}$, $-C(S)(R^{27})R^{28}$, $-SR^{29}$, $-C(O)SR^{30}$, $-CF_3$ or $-A_5-Q^5(X^9)X^{10}$;

or both $D^1$ and $E^1$ together with the carbon atoms of the cyclopentadienyl ring to which they are attached form an optionally substituted phenyl ring:

$X^1$ represents $CR^1(R^2)(R^3)$, congressyl or adamantyl, $X^2$ represents $CR^4(R^5)(R^6)$, congressyl or adamantyl, or $X^1$ and $X^2$ together with $Q^2$ to which they are attached form an optionally substituted 2-phospha-tricyclo[3.3.1.1 {3,7}]decyl group or derivative thereof, or $X^1$ and $X^2$ together with $Q^2$ to which they are attached form a ring system of formula IIIa

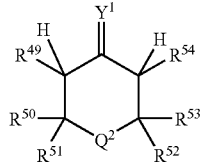

(IIIa)

$X^3$ represents $CR^7(R^8)(R^9)$, congressyl or adamantyl, $X^4$ represents $CR^{10}(R^{11})(R^{12})$, congressyl or adamantyl, or $X^3$ and $X^4$ together with $Q^1$ to which they are attached form an optionally substituted 2-phospha-tricyclo[3.3.1.1 {3,7}]decyl group or derivative thereof, or $X^3$ and $X^4$ together with $Q^1$ to which they are attached form a ring system of formula IIIb

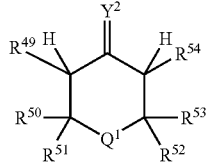

(IIIb)

$X^5$ represents $CR^{13}(R^{14})(R^{15})$, congressyl or adamantyl, $X^6$ represents $CR^{16}(R^{17})(R^{18})$, congressyl or adamantyl, or $X^5$ and $X^6$ together with $Q^3$ to which they are attached form an optionally substituted 2-phospha-tricyclo[3.3.1.1 {3,7}]decyl group or derivative thereof, or $X^5$ and $X^6$ together with $Q^3$ to which they are attached form a ring system of formula IIIc

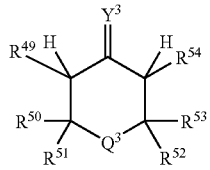

(IIIc)

$X^7$ represents $CR^{31}(R^{32})(R^{33})$, congressyl or adamantyl, $X^8$ represents $CR^{34}(R^{35})(R^{36})$, congressyl or adamantyl, or $X^7$ and $X^8$ together with $Q^4$ to which they are attached form an optionally substituted 2-phospha-tricyclo[3.3.1.1 {3,7}]decyl group or derivative thereof, or $X^7$ and $X^8$ together with $Q^4$ to which they are attached form a ring system of formula IIId

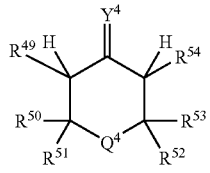

(IIId)

$X^9$ represents $CR^{37}(R^{38})(R^{39})$, congressyl or adamantyl, $X^{10}$ represents $CR^{40}(R^{41})(R^{42})$, congressyl or adamantyl, or $X^9$ and $X^{10}$ together with $Q^5$ to which they are attached form an optionally substituted 2-phospha-tricyclo[3.3.1.1.{3,7}]decyl group or derivative thereof, or $X^9$ and $X^{10}$ together with $Q^5$ to which they are attached form a ring system of formula IIIe

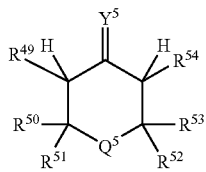

(IIIe)

and in this yet further embodiment,
$Q^1$ and $Q^2$, and $Q^3$, $Q^4$ and $Q^5$ (when present), each independently represent phosphorus, arsenic or antimony;
M represents a Group VIB or VIIIB metal or metal cation thereof;
$L_1$ represents an optionally substituted cyclopentadienyl, indenyl or aryl group;
$L_2$ represents one or more ligands each of which are independently selected from hydrogen, lower alkyl, alkylaryl, halo, CO, $P(R^{43})(R^{44})R^{45}$ or $N(R^{46})(R^{47})R^{48}$;
$R^1$ to $R^{18}$ and $R^{31}$ to $R^{42}$, when present, each independently represent hydrogen, lower alkyl, aryl, halo or Het;
$R^{19}$ to $R^{30}$ and $R^{43}$ to $R^{48}$, when present, each independently represent hydrogen, lower alkyl, aryl or Het;
$R^{49}$, $R^{54}$ and $R^{55}$, when present, each independently represent hydrogen, lower alkyl or aryl;
$R^{50}$ to $R^{53}$, when present, each independently represent hydrogen, lower alkyl, aryl or Het;
$Y^1, Y^2, Y^3, Y^4$ and $Y^5$, when present, each independently represent oxygen, sulfur or N—$R^{55}$;
n=0 or 1;
and m=0 to 5;
provided that when n=1 then m equals 0, and when n equals 0 then m does not equal 0; and
(b) palladium or a compound thereof,
wherein the ACCF (product kg·hr$^{-1}$·dm$^{-3}$) is maintained at less than 0.5 in a continuous carbonylation process.

3. A continuous carbonylation process according to claim 1, wherein each of $Q^1$, $Q^2$ and $Q^3$ (when present) represents phosphorus.

4. A continuous carbonylation process according to claim 1, wherein the low ACCF is held or maintained by suitable dilution of the carbonylation reaction medium.

5. A continuous carbonylation process according to claim 1, wherein the catalyst system also includes as a further compound (c), an acid.

6. A continuous carbonylation process according to claim 1, wherein the bidentate ligand is selected from the group consisting of 1,2-bis(diadamantylphosphinomethyl)benzene, 1,2-bis(di-3,5-dimethyladamantylphosphinomethyl)benzene, 1,2-bis(di-5-tert-butyladamantylphosphinomethyl)benzene, 1,2-bis(1-adamantyl tert-butyl-phosphinomethyl)benzene, 1-(diadamantylphosphinomethyl)-2-(di-tert-butylphosphinomethyl)benzene, 1-(di-tert-butylphosphinomethyl)-2-(dicongressylphosphinomethyl)benzene, 1-(di-tert-butylphosphinomethyl)-2-(phospha-adamantyl-P-methyl)benzene, 1-(diadamantylphosphinomethyl)-2-(phospha-adamantyl-P-methyl)benzene, 1-(tert-butyladamantylphosphinomethyl)-2-(di-adamantylphosphinomethyl)benzene and 1-[(P-(2,2,6,6-tetra-methylphosphinan-4-one)phosphinomethyl)]-2-(phospha-adamantyl-P-methyl)benzene, wherein "phospha-adamantyl" is selected from 2-phospha-1,3,5,7-tetramethyl-6,9,10-trioxadamantyl,2-phospha-1,3,5-trimethyl-6,9,10 trioxadamantyl, 2-phospha-1,3,5,7-tetra(trifluoromethyl)-6,9,10-trioxadamantyl and 2-phospha-1,3,5-tri(trifluoromethyl)-6,9,10-trioxadamantyl.

7. A continuous carbonylation process according to claim 1, wherein the hydroxyl group containing compound includes water or an organic molecule having a hydroxyl functional group.

8. A continuous carbonylation process according to claim 1, wherein the ethylenically unsaturated compounds may be non-substituted or substituted with lower alkyl (which alkyl group may itself be substituted, unsubstituted or terminated), aryl, Het, halo, cyano, nitro, thioalkoxy, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $C(S)NR^{25}R^{26}$, $SR^{27}$, $C(O)SR^{27}$, wherein $R^{19}$ to $R^{27}$ each independently represent hydrogen, aryl or lower alkyl (which alkyl group may itself be substituted, unsubstituted or terminated).

9. A continuous carbonylation process according to claim 1, wherein the Group VIB or VIIIB metal or a compound thereof is selected from Groups 6, 8, 9 and 10 of the modern periodic table.

10. A continuous carbonylation process according to claim 1, wherein the ethylenically unsaturated compound is ethylene.

* * * * *

UNITED STATES PATENT AND TRADEMARK OFFICE
CERTIFICATE OF CORRECTION

| | | |
|---|---|---|
| PATENT NO. | : 8,604,236 B2 | Page 1 of 1 |
| APPLICATION NO. | : 11/990272 | |
| DATED | : December 10, 2013 | |
| INVENTOR(S) | : Eastham et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 870 days.

Signed and Sealed this
Fourteenth Day of April, 2015

Michelle K. Lee
*Director of the United States Patent and Trademark Office*